United States Patent
Marshall et al.

(10) Patent No.: US 11,213,030 B2
(45) Date of Patent: Jan. 4, 2022

(54) 4-(3,4-DIHYDRONAPHTH-1-YL OR 2H-CHROMEN-4-YL)-5-HYDROXY-2H-PYRADIZIN-3-ONES AS HERBICIDES

(71) Applicant: FMC Corporation, Philadelphia, PA (US)

(72) Inventors: Eric Allen Marshall, Rising Sun, MD (US); John Robbins Debergh, Middletown, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 16/623,628

(22) PCT Filed: Jun. 13, 2018

(86) PCT No.: PCT/US2018/037330
§ 371 (c)(1),
(2) Date: Dec. 17, 2019

(87) PCT Pub. No.: WO2019/005484
PCT Pub. Date: Jan. 3, 2019

(65) Prior Publication Data
US 2020/0196604 A1 Jun. 25, 2020

Related U.S. Application Data

(60) Provisional application No. 62/527,523, filed on Jun. 30, 2017.

(51) Int. Cl.
C07D 237/16 (2006.01)
A01N 43/58 (2006.01)
C07D 405/04 (2006.01)

(52) U.S. Cl.
CPC .......... *A01N 43/58* (2013.01); *C07D 237/16* (2013.01); *C07D 405/04* (2013.01)

(58) Field of Classification Search
CPC .................................................. C07D 237/16
See application file for complete search history.

(56) References Cited

U.S. PATENT DOCUMENTS

| | | |
|---|---|---|
| 8,470,738 B2 | 6/2013 | Fusaka |
| 8,884,010 B2 | 11/2014 | Jachmann et al. |
| 9,040,709 B2 | 5/2015 | Jachmann et al. |
| 9,049,864 B2 | 6/2015 | Burton et al. |
| 2010/0267561 A1 | 10/2010 | Stevenson et al. |
| 2018/0312467 A1 | 11/2018 | Selby et al. |
| 2018/0332851 A1 | 11/2018 | Stevenson et al. |

FOREIGN PATENT DOCUMENTS

| | | |
|---|---|---|
| GB | 1130716 | 10/1968 |
| WO | 2005007632 | 1/2005 |
| WO | 20070119434 | 10/2007 |
| WO | 20090035145 | 3/2009 |
| WO | 20090035151 | 3/2009 |
| WO | 20130050421 | 4/2013 |
| WO | 2013160126 | 10/2013 |
| WO | 2014031971 | 2/2014 |
| WO | 20150132608 | 9/2015 |
| WO | 20150168010 | 11/2015 |
| WO | 20170074992 | 5/2017 |
| WO | 2018183432 | 10/2018 |
| WO | 2019005484 | 1/2019 |

OTHER PUBLICATIONS

Babichev et al., "6-Amino-1-aryl-4-pyridazinones and their derivatives", Ukrainskii Khimicheskii Zhurnal (Russian Edition), vol. 49, Issue 11, pp. 1197-1202, 1983.
International Search Report of corresponding PCT/2018/037330 dated Aug. 8, 2018.

*Primary Examiner* — Brian E McDowell
(74) *Attorney, Agent, or Firm* — Xiaobin Ding; FMC Corporation

(57) ABSTRACT

Disclosed are compounds of Formula 1, including all stereoisomers, N-oxides, and salts thereof, Formula (1) wherein W, $R^1$, $R^2$, $R^3$, n, $R^4$, $R^5$, $R^6$, L and G are as defined in the disclosure. Also disclosed are compositions containing the compounds of Formula 1 and methods for controlling undesired vegetation comprising contacting the undesired vegetation or its environment with an effective amount of a compound or a composition of the invention.

(1)

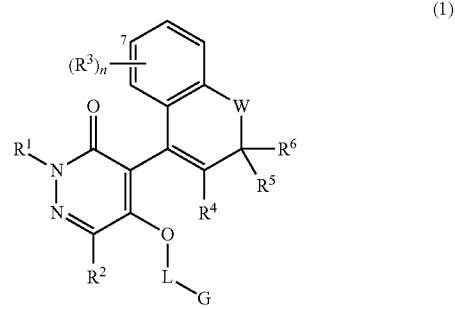

8 Claims, No Drawings

4-(3,4-DIHYDRONAPHTH-1-YL OR 2H-CHROMEN-4-YL)-5-HYDROXY-2H-PYRADIZIN-3-ONES AS HERBICIDES

FIELD OF THE INVENTION

This invention relates to certain saturated bicyclic pyridazinones, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action. Patent application publications WO 2015/168010 and WO 2017/074992, and patent application PCT/US18/24742 disclose substituted pyridazinones. The saturated bicyclic pyridazinones of the present invention are are not disclosed in these patent applications.

SUMMARY OF THE INVENTION

This invention is directed to compounds of Formula 1, including all stereoisomers, N-oxides of such compounds, and salts of such compounds, and agricultural compositions containing such compounds, and the use of such compounds as herbicides:

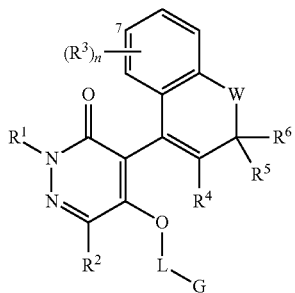

wherein
W is —C($R^7$)($R^8$)— or —O—;
$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_2$-$C_7$ alkenyl, $C_3$-$C_7$ alkynyl, $C_3$-$C_7$ cycloalkyl, $C_4$-$C_7$ cycloalkylalkyl, $C_2$-$C_5$ cyanoalkyl, $C_1$-$C_4$ nitroalkyl, $C_2$-$C_7$ haloalkoxyalkyl, $C_1$-$C_7$ haloalkyl, $C_2$-$C_7$ haloalkenyl, $C_2$-$C_7$ alkoxyalkyl, $C_3$-$C_7$ alkylthioalkyl or $C_1$-$C_7$ alkoxy;
$R^2$ is H, halogen, cyano, —CHO, $C_1$-$C_7$ alkyl, $C_3$-$C_8$ alkylcarbonylalkyl, $C_3$-$C_8$ alkoxycarbonylalkyl, $C_1$-$C_4$ alkylcarbonyl, $C_2$-$C_7$ alkylcarbonyloxy, $C_4$-$C_7$ alkylcycloalkyl, $C_2$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_5$ cyanoalkyl, $C_1$-$C_4$ nitroalkyl, $C_2$-$C_7$ haloalkoxyalkyl, $C_1$-$C_7$ haloalkyl, $C_2$-$C_7$ haloalkenyl, $C_2$-$C_7$ alkoxyalkyl, $C_1$-$C_7$ alkoxy, $C_1$-$C_5$ alkylthio or $C_2$-$C_3$ alkoxycarbonyl;
each $R^3$ is independently H, halogen, nitro, cyano, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_2$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_4$ haloalkylthio or $C_2$-$C_5$ alkoxycarbonyl;
n is 0 to 3;
each $R^4$ is independently H, halogen, nitro, cyano, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_2$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_4$ haloalkylthio or $C_2$-$C_5$ alkoxycarbonyl;
$R^5$ is H or $C_1$-$C_5$ alkyl;
$R^6$ is H or $C_1$-$C_5$ alkyl;
$R^7$ is H or $C_1$-$C_5$ alkyl;
$R^8$ is H or $C_1$-$C_5$ alkyl;
L is a direct bond, $C_1$-$C_4$ alkanediyl or $C_2$-$C_4$ alkenediyl;
G is H, C(=O)$R^9$, C(=S)$R^9$, $CO_2R^{10}$, C(=O)$SR^{10}$, S(O)$_2R^9$, C(=O)N($R^{11}$)($R^{12}$), S(=O)$_2$N($R^{11}$)($R^{12}$) or P(=O)($R^{13}$)($R^{14}$); or $C_1$-$C_7$ alkyl, $C_2$-$C_5$ alkenyl, $C_2$-$C_4$ alkynyl, $C_1$-$C_7$ haloalkyl, $C_2$-$C_5$ haloalkenyl, $C_2$-$C_4$ haloalkynyl, $C_2$-$C_4$ alkoxyalkyl, $C_3$-$C_6$ cycloalkyl or $C_4$-$C_7$ cycloalkylalkyl; or a 5- or 6-membered heterocyclic ring optionally substituted by halogen, $C_1$-$C_4$ alkyl or $C_1$-$C_4$ haloalkyl;
$R^9$ and $R^{11}$ are independently H, $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl or $C_4$-$C_7$ cycloalkylalkyl; or phenyl, benzyl, or a 5- to 6-membered heterocyclic ring, each phenyl, benzyl or heterocyclic ring optionally substituted by halogen, $C_1$-$C_4$ alkyl or $C_1$-$C_4$ haloalkyl;
$R^{10}$ is $C_1$-$C_7$ alkyl, $C_3$-$C_7$ alkenyl, $C_3$-$C_7$ alkynyl, $C_3$-$C_7$ cycloalkyl, $C_2$-$C_7$ haloalkyl, $C_3$-$C_7$ haloalkenyl, $C_2$-$C_7$ alkoxyalkyl or $C_4$-$C_7$ cycloalkylalkyl; or phenyl, benzyl or a 5- to 6-membered heterocyclic ring, each phenyl, benzyl or heterocyclic ring optionally substituted by halogen, $C_1$-$C_4$ alkyl or $C_1$-$C_4$ haloalkyl;
$R^{12}$ is H, $C_1$-$C_7$ alkyl, $C_2$-$C_7$ alkenyl, $C_2$-$C_7$ alkynyl, $C_3$-$C_7$ cycloalkyl, $C_4$-$C_7$ cycloalkylalkyl, $C_1$-$C_7$ haloalkyl or $C_2$-$C_7$ alkoxyalkyl;
$R^{13}$ is $C_1$-$C_7$ alkyl or $C_1$-$C_7$ alkoxy; and
$R^{14}$ is $C_1$-$C_7$ alkyl or $C_1$-$C_7$ alkoxy.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Cyanoalkyl" denotes an alkyl group substituted with one cyano group. Examples of "cyanoalkyl" include $NCCH_2$ and $NCCH_2CH_2$ (alternatively identified as $CH_2CH_2CN$). The term "nitroalkyl" represents a nitro group bonded through an alkyl moiety. Examples of "nitroalkyl" include $O_2NCH_2$ and $O_2NCH_2CH_2$ (alternatively identified as $CH_2CH_2NO_2$). The terms "alkylamino" and "dialkylamino" refer to mono- and di-alkyl substitution on an amine moiety, respectively. Examples of "alkylamino" include $CH_3NH-$, $(CH_3)_2CHNH-$ and $CH_3CH_2CH_2NH-$. Examples of "dialkylamino" include $(CH_3)_2N-$, $(CH_3)_2N-$ and $(CH_3)_2CH_2CH_2N-$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)-$, $CH_3CH_2S(O)-$, $CH_3CH_2CH_2S(O)-$, $(CH_3)_2CHS(O)-$ and the different butylsulfinyl, pentylsulfinyl and hexylsulfinyl isomers. "Alkylsulfonyl" indicates a sulfonyl moiety substituted with a straight-chain or branched alkyl group. Examples of "alkylsulfonyl" include $CH_3S(O)_2-$, $CH_3CH_2S(O)_2-$, $CH_3CH_2CH_2S(O)_2-$, $(CH_3)_2CHS(O)_2-$, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2-$, $CH_3SCH_2CH_2-$, $CH_3CH_2SCH_2-$, $CH_3CH_2CH_2CH_2SCH_2-$ and $CH_3CH_2SCH_2CH_2-$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", "haloalkylthio", "haloalkenyl", "haloalkynyl", "haloalkoxyalky", and the like, are is defined analogously to the term "haloalkyl". Examples of "haloalkoxy" include $CF_3O-$, $CCl_3CH_2O-$, $HCF_2CH_2CH_2O-$ and $CF_3CH_2O-$. Examples of "haloalkylthio" include CCl₃S—, CF₃S—, CCl₃CH₂S— and Cl-CH₂CH₂CH₂S—. Examples of "haloalkenyl" include (Cl)₂C=CHCH₂— and CF₃CH₂CH=CHCH₂—. Examples of "haloalkynyl" include HC≡CCHCl—, CF₃C≡C—, CCl₃C≡C— and FCH₂C≡CCH₂—. Examples of "haloalkoxyalkyl" include CF₃OCH₂CH₂—, CCl₃CH₂OCH₂—, HCF₂CH₂CH₂OCH₂— and CF₃CH₂OCH₂—.

"Alkylcarbonyl" denotes a straight-chain or branched alkyl moiety bonded to a C(=O) moiety. Examples of "alkylcarbonyl" include CH₃C(=O)—, CH₃CH₂CH₂C(=O)— and (CH₃)₂CHC(=O)—. "Alkoxycarbonyl" denotes a straight-chain or branched alkoxy moieties bonded to a C(=O) moiety. Examples of "alkoxycarbonyl" include CH₃OC(=O)—, CH₃CH₂OC(=O)—, CH₃CH₂CH₂OC(=O)—, (CH₃)₂CHOC(=O)— and the different butoxy- or pentoxycarbonyl isomers. "Alkylcarbonylalkyl" denotes a straight-chain or branched chain alkyl group bonded to the carbon atom of to a carbonylalkyl moiety. "Alkoxycarbonylalkyl" denotes a straight-chain or branched alkoxycarbonyl moieties bonded to linear or branched a alkylene moiety. Examples of "alkoxycarbonylalkyl" include CH₃OC(=O)CH₂CH₂—, CH₃CH₂OC(=O)CH₂—, CH₃CH₂CH₂OC(=O)CH₂CH(CH₃)—, (CH₃)₂CHOC(=O)CH₂— and the different butoxy- or pentoxycarbonylalkyl isomers. "Alkylcarbonyloxy" denotes a straight-chain or branched-chain alkyl group bonded to the carbon atom of to a carbonyloxy moiety. Examples of "alkylcarbonyloxy" include (CH₃)C(=O)O— and (CH₃CH₂)C(=O)O—. The term alkanediyl or alkenediyl refers to a linear or branched alkane or alkene linking chain respectively. Examples of alkanediyl include —CH₂—, —CH₂CH(CH₃)— or —CH₂CH₂CH₂—. Examples of alkenediyl include —CH=CH—, —CH₂C=CH— or —CH=C(CH₃)—. The term "adjacent" in the context of locating a substituent means "next to" or "immediately next to".

The total number of carbon atoms in a substituent group is indicated by the "$C_i$-$C_j$" prefix where i and j are numbers from 1 to 7. For example, $C_1$-$C_4$ alkylsulfonyl designates methylsulfonyl through butylsulfonyl; $C_2$ alkoxyalkyl designates CH₃OCH₂—; $C_3$ alkoxyalkyl designates, for example, CH₃CH(OCH₃)—, CH₃OCH₂CH₂— or CH₃CH₂OCH₂—; and $C_4$ alkoxyalkyl designates the various isomers of an alkyl group substituted with an alkoxy group containing a total of four carbon atoms, examples including CH₃CH₂CH₂OCH₂— and CH₃CH₂OCH₂CH₂—.

When a compound is substituted with a substituent bearing a subscript that indicates the number of said substituents can exceed 1, said substituents (when they exceed 1) are independently selected from the group of defined substituents, (e.g., $(R^3)_n$, n is 0, 1, 2 or 3). When a group contains a substituent which can be hydrogen, for example $R^3$ or $R^4$, then when this substituent is taken as hydrogen, it is recognized that this is equivalent to said group being unsubstituted. When a variable group is shown to be optionally attached to a position, for example $(R^3)_n$ wherein n may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" as a component of Formula 1 (e.g., substituent [J]) is carbocyclic or heterocyclic. The term "ring member" refers to an atom or other moiety (e.g., C(=O), C(=S), S(O) or S(O)₂) forming the backbone of a ring. The terms "carbocyclic ring", "carbocycle" or "carbocyclic ring system" denote a ring wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring" or "heterocycle" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen. "Aromatic" indicates that each of the ring atoms is essentially in the same plane and has a p-orbital perpendicular to the ring plane, and that (4n+2) π electrons, where n is a positive integer, are associated with the ring to comply with Hückel's rule.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

As noted above, G, $R^{10}$ or $R^{11}$ can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein $R^v$ is as defined in the Summary of the Invention for G and r is an integer from 0 to 5. As noted above, G, $R^{10}$ or $R^{11}$ can be (among others) 5- or 6-membered heterocyclic ring, which may be saturated or unsaturated, optionally substituted with one or more substituents selected from a group of substituents as defined in the Summary of the Invention. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary of the Invention for G, $R^{10}$ or $R^{11}$ and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1
U-1 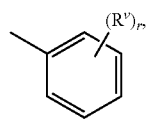
U-2 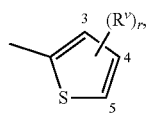
U-3 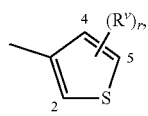
U-4 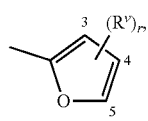
U-5 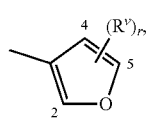
U-6 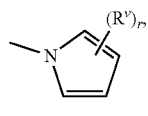
U-7 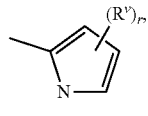
U-8 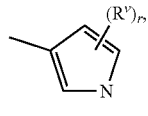
U-9 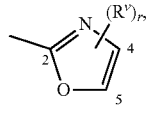
U-10 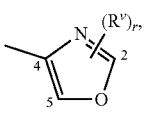
U-11 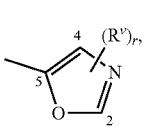
U-12 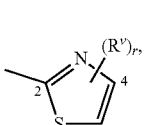
-continued
U-13 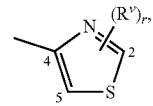
U-14 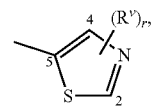
U-15 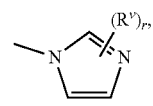
U-16 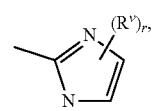
U-17 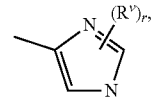
U-18 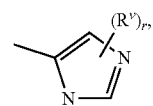
U-19 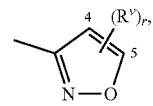
U-20
U-21
U-22
U-23
U-24
U-25

-continued
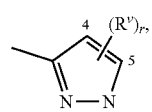 U-26
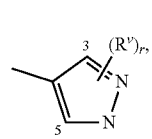 U-27
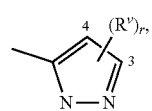 U-28
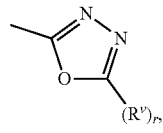 U-29
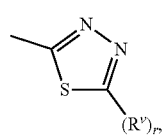 U-30
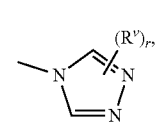 U-31
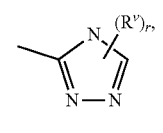 U-32
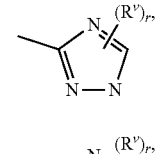 U-33
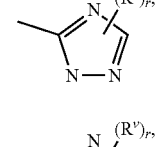 U-34
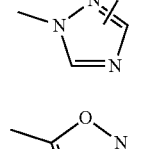 U-35
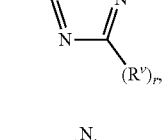 U-36
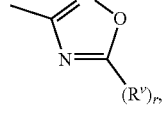 U-37
-continued
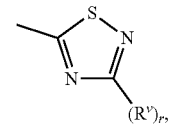 U-38
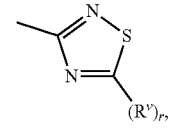 U-39
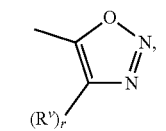 U-40
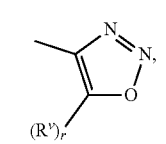 U-41
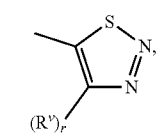 U-42
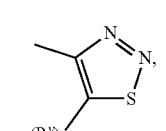 U-43
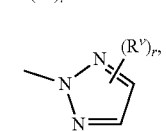 U-44
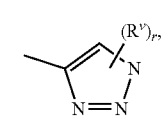 U-45
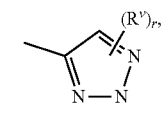 U-46
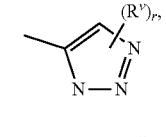 U-47
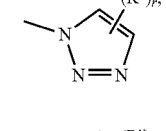 U-48
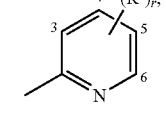 U-49

-continued

U-50 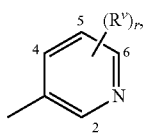

U-51 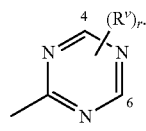

U-52 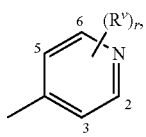

U-53 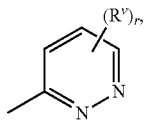

U-54 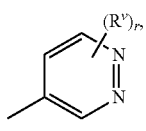

U-55 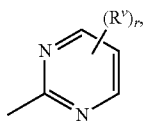

U-56 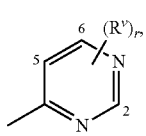

U-57 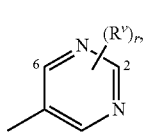

U-58 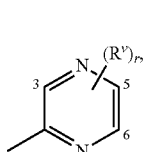

U-59 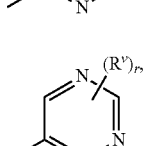

U-60 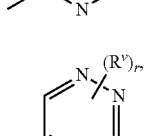

-continued

Note that when G, $R^{10}$ or $R^{11}$ is a 5- or 6-membered saturated or unsaturated non-aromatic heterocyclic ring optionally substituted with one or more substituents selected from the group of substituents as defined in the Summary of the Invention for G, $R^{10}$ or $R^{11}$, one or two carbon ring members of the heterocycle can optionally be in the oxidized form of a carbonyl moiety.

Examples of a 5- or 6-membered saturated or non-aromatic unsaturated heterocyclic ring containing ring members selected from up to two O atoms and up to two S atoms, and optionally substituted on carbon atom ring members with up to five halogen atoms includes the rings G-1 through G-35 as illustrated in Exhibit 2. Note that when the attachment point on the G group is illustrated as floating, the G group can be attached to the remainder of Formula 1 through any available carbon or nitrogen of the G group by replacement of a hydrogen atom. The optional substituents corresponding to $R^v$ can be attached to any available carbon or nitrogen by replacing a hydrogen atom. For these G rings, r is typically an integer from 0 to 4, limited by the number of available positions on each G group.

Note that when G, $R^{10}$ or $R^{11}$ comprises a ring selected from G-28 through G-35, $G^2$ is selected from O, S or N. Note that when $G^2$ is N, the nitrogen atom can complete its valence by substitution with either H or the substituents corresponding to $R^v$ as defined in the Summary of the Invention as halogen, $C_1$-$C_4$ alkyl or $C_1$-$C_4$ haloalkyl.

Exhibit 2

G-1 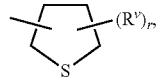

G-2 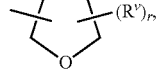

G-3 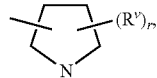

G-4 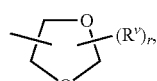

G-5 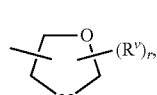

G-6 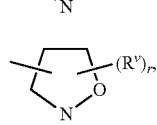

-continued
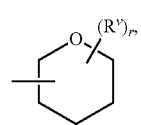 G-7
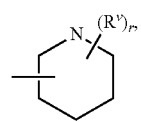 G-8
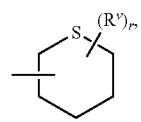 G-9
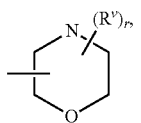 G-10
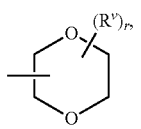 G-11
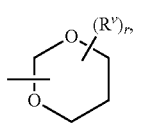 G-12
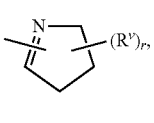 G-13
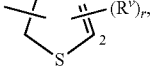 G-14
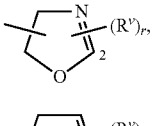 G-15
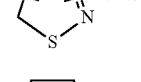 G-16
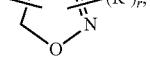 G-17
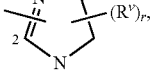 G-18
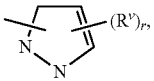 G-19
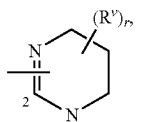 G-20
-continued
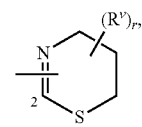 G-21
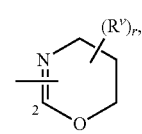 G-22
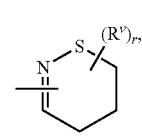 G-23
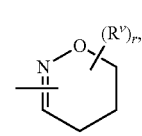 G-24
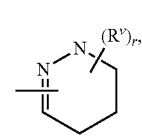 G-25
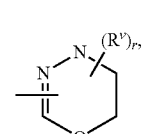 G-26
G-27
G-28
G-29
G-30
G-31
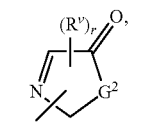 G-32

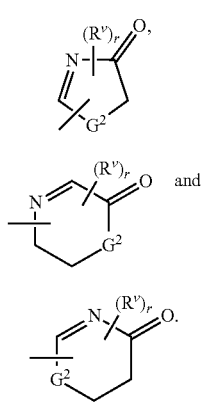

G-33

G-34 and

G-35

Although $R^v$ groups are shown in the structures U-1 through U-61, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

For example, when $R^5$ or $R^6$ are dissimilar, then Formula 1 possesses a chiral center at the carbon atom to which $R^1$ is bonded. The two enantiomers are depicted as Formula 1' and Formula 1" with the chiral center identified with an asterisk (*). For a comprehensive discussion of all aspects of stereoisomerism, see Ernest L. Eliel and Samuel H. Wilen, *Stereochemistry of Organic Compounds*, John Wiley & Sons, 1994.

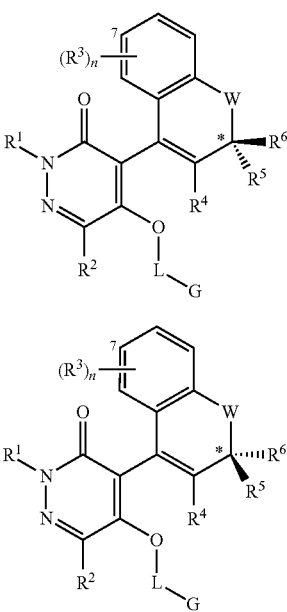

Note that when W is —C($R^7$)($R^8$)— and $R^7$ and $R^8$ are different, then the carbon atom to which they are both bonded will also possess a chiral center. In combination with $R^5$ or $R^6$ being different these two chiral centers are referred to as "diasteromers". Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the broad end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This invention comprises racemic mixtures, for example, equal amounts of the enantiomers of Formulae 1' and 1", or when $R^7$ and $R^8$ are dissimilar. In addition, this invention includes compounds that are enriched compared to the racemic mixture in an enantiomer of Formula 1. Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enantiomeric excess ("ee"), which is defined as $(2x-1) \cdot 100\%$, where x is the mole fraction of the dominant enantiomer in the mixture (e.g., an ee of 20% corresponds to a 60:40 ratio of enantiomers).

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as $R^1$ and $R^2$ may themselves contain chiral centers. This invention comprises racemic mixtures as well as enriched and essentially pure stereoconfigurations at these additional chiral centers.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include where Formula 1 including N-oxides, salts, compositions and use thereof are described as follows:

Embodiment 1. A compound of Formula 1, including all stereoisomers, N-oxides, and salts thereof, agricultural compositions containing them and their use as herbicides as described in the Summary of the Invention.

Embodiment 2. A compound of Embodiment 1 wherein W is —C($R^7$)($R^8$)—.

Embodiment 3. A compound of Embodiment 1 wherein W is —O—.

Embodiment 4. A compound of any one of Embodiments 1 through 3 wherein wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_1$-$C_7$ haloalkyl, $C_2$-$C_7$ haloalkenyl, $C_2$-$C_7$ alkoxyalkyl or $C_1$-$C_7$ alkoxy.

Embodiment 5. A compound of Embodiment 4 wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_7$ alkoxyalkyl or $C_1$-$C_7$ alkoxy.

Embodiment 6. A compound of Embodiment 5 wherein $R^1$ is H, $C_1$-$C_7$ alkyl, $C_4$-$C_7$ alkylcycloalkyl, $C_3$-$C_7$ cycloalkyl, $C_4$-$C_7$ cycloalkylalkyl or $C_2$-$C_7$ alkoxyalkyl.

Embodiment 7. A compound of Embodiment 6 wherein $R^1$ is H, $C_1$-$C_7$ alkyl, $C_3$-$C_7$ cycloalkyl, $C_4$-$C_7$ cycloalkylalkyl or $C_2$-$C_7$ alkoxyalkyl.

Embodiment 8. A compound of Embodiment 7 wherein $R^1$ is H, $C_1$-$C_7$ alkyl, $C_3$-$C_7$ cycloalkyl or $C_2$-$C_7$ alkoxyalkyl.

Embodiment 9. A compound of Embodiment 8 wherein $R^1$ is H or $C_1$-$C_7$ alkyl.

Embodiment 10. A compound of Embodiment 9 wherein $R^1$ is H.

Embodiment 11. A compound of Embodiment 9 wherein $R^1$ is $C_1$-$C_4$ alkyl.

Embodiment 12. A compound of Embodiment 11 wherein $R^1$ is $C_2$-$C_4$ alkyl.

Embodiment 13. A compound of Embodiment 11 wherein $R^1$ is methyl or ethyl.

Embodiment 14. A compound of Embodiment 13 wherein $R^1$ is methyl.

Embodiment 15. A compound of any one of Embodiments 1 through 9 wherein $R^1$ is other than methyl.

Embodiment 16. A compound of any one of Embodiments 1 through 10 wherein $R^1$ is other than H.

Embodiment 17. A compound of any one of Embodiments 1 through 16 wherein $R^2$ is H, halogen, cyano, —CHO, $C_1$-$C_7$ alkyl, $C_3$-$C_8$ alkylcarbonylalkyl, $C_3$-$C_8$ alkoxycarbonylalkyl, $C_1$-$C_4$ alkylcarbonyl, $C_2$-$C_7$ alkylcarbonyloxy, $C_4$-$C_7$ alkylcycloalkyl, $C_3$-$C_7$ cycloalkyl, $C_4$-$C_7$ cycloalkylalkyl, $C_2$-$C_7$ haloalkoxyalkyl, $C_1$-$C_7$ haloalkyl, $C_2$-$C_7$ alkoxyalkyl, $C_1$-$C_7$ alkoxy, $C_1$-$C_5$ alkylthio or $C_2$-$C_3$ alkoxycarbonyl.

Embodiment 18. A compound of Embodiment 17 wherein $R^2$ is H, halogen, cyano, —CHO, $C_1$-$C_7$ alkyl, $C_4$-$C_7$ alkylcycloalkyl, $C_3$-$C_7$ cycloalkyl, $C_4$-$C_7$ cycloalkylalkyl, $C_2$-$C_7$ haloalkoxyalkyl, $C_1$-$C_7$ haloalkyl, $C_2$-$C_7$ alkoxyalkyl, $C_1$-$C_7$ alkoxy or $C_1$-$C_5$ alkylthio.

Embodiment 19. A compound of Embodiment 18 wherein $R^2$ is H, halogen, cyano, $C_1$-$C_7$ alkyl, $C_2$-$C_7$ haloalkoxyalkyl, $C_1$-$C_7$ haloalkyl, $C_2$-$C_7$ alkoxyalkyl, $C_1$-$C_7$ alkoxy or $C_1$-$C_5$ alkylthio.

Embodiment 20. A compound of Embodiment 19 wherein $R^2$ is H, halogen, cyano, $C_1$-$C_7$ alkyl, $C_1$-$C_7$ haloalkyl or $C_1$-$C_7$ alkoxy.

Embodiment 21. A compound of Embodiment 20 wherein $R^2$ is H, Cl, Br, I, cyano, methyl, $CF_3$ or methoxy.

Embodiment 22. A compound of Embodiment 21 wherein $R^2$ is H, Cl, methyl or methoxy.

Embodiment 23. A compound of Embodiment 22 wherein $R^2$ is Cl or methyl.

Embodiment 24. A compound of Embodiment 22 wherein $R^2$ is Cl.

Embodiment 25. A compound of Embodiment 22 wherein $R^2$ is methyl.

Embodiment 26. A compound of Embodiment 22 wherein $R^2$ is methoxy.

Embodiment 27. A compound of any one of Embodiments 1 through 22 wherein $R^2$ is other than H.

Embodiment 28. A compound of any one of Embodiments 1 through 27 wherein each $R^3$ is independently H, halogen, $C_1$-$C_5$ alkyl, $C_3$-$C_5$ cycloalkyl, $C_1$-$C_5$ haloalkyl, $C_1$-$C_5$ alkoxy or $C_1$-$C_5$ haloalkoxy.

Embodiment 29. A compound of Embodiment 28 wherein each $R^3$ is independently H, halogen, $C_1$-$C_5$ alkyl, $C_1$-$C_5$ haloalkyl, $C_1$-$C_5$ alkoxy or $C_1$-$C_5$ haloalkoxy.

Embodiment 30. A compound of Embodiment 29 wherein each $R^3$ is independently H, halogen, methyl, ethyl, $CF_3$ or —$OCHF_2$.

Embodiment 31. A compound of Embodiment 30 wherein each $R^3$ is independently H, F, Cl, Br or methyl.

Embodiment 32. A compound of Embodiment 31 wherein each $R^3$ is H.

Embodiment 33. A compound of Embodiment 31 wherein each $R^3$ is independently H, Cl, Br or methyl.

Embodiment 34. A compound of Embodiment 33 wherein each $R^3$ is independently H or methyl.

Embodiment 35. A compound of any one of Embodiments 1 through 34 wherein n is 0 to 2.

Embodiment 36. A compound of Embodiment 35 wherein n is 0 or 1.

Embodiment 37. A compound of Embodiment 36 wherein n is 1.

Embodiment 38. A compound of any one of Embodiments 1 through 37 wherein $R^3$ is located at the 7-position.

Embodiment 39. A compound of any one of Embodiments 1 through 38 wherein $R^4$ is H, halogen, $C_1$-$C_3$ alkyl, $C_3$-$C_4$ cycloalkyl, $C_1$-$C_3$ haloalkyl or $C_1$-$C_3$ alkoxy.

Embodiment 40. A compound of Embodiment 39 wherein $R^4$ is H, halogen, $C_1$-$C_2$ alkyl, cyclopropyl or $C_1$-$C_2$ haloalkyl.

Embodiment 41. A compound of Embodiment 40 wherein $R^4$ is H, halogen, methyl, ethyl or $CF_3$.

Embodiment 42. A compound of Embodiment 41 wherein $R^4$ is H, F, Cl, Br or methyl.

Embodiment 43. A compound of Embodiment 42 wherein $R^4$ is methyl.

Embodiment 44. A compound of Embodiment 42 wherein $R^4$ is H.

Embodiment 45. A compound of any one of Embodiments 1 through 44 wherein $R^5$ is H or methyl.

Embodiment 46. A compound of Embodiment 45 wherein $R^5$ is H.

Embodiment 47. A compound of any one of Embodiments 1 through 46 wherein $R^6$ is H or methyl.

Embodiment 48. A compound of Embodiment 47 wherein $R^6$ is H.

Embodiment 49. A compound of any one of Embodiments 1 through 48 wherein $R^7$ is H or methyl.

Embodiment 50. A compound of Embodiment 49 wherein $R^7$ is H.

Embodiment 51. A compound of any one of Embodiments 1 through 50 wherein $R^8$ is H or methyl.

Embodiment 52. A compound of Embodiment 51 wherein $R^8$ is H.

Embodiment 53. A compound of any one of Embodiments 1 through 52 wherein L is a direct bond or $C_1$-$C_2$ alkanediyl.

Embodiment 54. A compound of Embodiment 53 wherein L is a direct bond.

Embodiment 55. A compound of any one of Embodiments 1 through 52 wherein L is $C_1$-$C_2$ alkanediyl or $C_2$-$C_3$ alkenediyl.

Embodiment 56. A compound of any one of Embodiments 1 though 53 or 55 wherein L is $C_1$-$C_2$ alkanediyl.

Embodiment 57. A compound of Embodiment 55 wherein L is —$CH_2$— or —CH=CH—.

Embodiment 58. A compound of Embodiment 57 wherein L is —$CH_2$—.

Embodiment 59. A compound of any one of Embodiments 1 through 58 wherein G is H, C(=O)$R^9$, C(=S)$R^9$, $CO_2R^{10}$, C(=O)$SR^{10}$, C(=O)N($R^{11}$)($R^{12}$) or P(=O)($R^{13}$)($R^{14}$) or $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_3$-$C_6$ cycloalkyl or $C_4$-$C_7$ cycloalkylalkyl.

Embodiment 60. A compound of Embodiment 59 wherein G is H, C(=O)$R^9$, $CO_2R^{10}$, C(=O)N($R^{11}$)($R^{12}$) or P(=O)($R^{13}$)($R^{14}$); or $C_1$-$C_4$ alkyl, $C_2$-$C_4$ alkenyl, $C_1$-$C_4$ haloalkyl, $C_2$-$C_4$ haloalkenyl, $C_2$-$C_4$ alkoxyalkyl, $C_3$-$C_6$ cycloalkyl or $C_4$-$C_7$ cycloalkylalkyl.

Embodiment 61. A compound of Embodiment 60 wherein G is H, C(=O)$R^9$, $CO_2R^{10}$ or P(=O)($R^{13}$)($R^{14}$); or $C_1$-$C_4$ alkyl, $C_1$-$C_4$ haloalkyl, $C_2$-$C_4$ alkoxyalkyl or $C_3$-$C_6$ cycloalkyl.

Embodiment 62. A compound of Embodiment 61 wherein G is H, C(=O)$R^9$ or $CO_2R^{10}$; or $C_2$-$C_4$ alkoxyalkyl or $C_3$-$C_6$ cycloalkyl.

Embodiment 63. A compound of Embodiment 62 wherein G is H.

Embodiment 64. A compound of Embodiment 62 wherein G is C(=O)$R^9$.

Embodiment 65. A compound of Embodiment 62 wherein G is $CO_2R^{10}$.

Embodiment 66. A compound of Embodiment 62 wherein G is $C_2$-$C_4$ alkoxyalkyl.

Embodiment 67. A compound of Embodiment 62 wherein G is $C_3$-$C_6$ cycloalkyl.

Embodiment 68. A compound of any one of Embodiments 1 through 62 or 64 wherein $R^9$ and $R^{11}$ are independently H, $C_1$-$C_7$ alkyl, $C_3$-$C_7$ alkenyl, $C_3$-$C_7$ alkynyl, $C_3$-$C_7$ cycloalkyl or $C_1$-$C_7$ haloalkyl; or phenyl, benzyl, or a 6-membered heterocyclic ring, each phenyl, benzyl or heterocyclic ring optionally substituted by halogen, $C_1$-$C_4$ alkyl or $C_1$-$C_4$ haloalkyl.

Embodiment 69. A compound of Embodiment 68 wherein $R^9$ and $R^{11}$ are independently H, $C_1$-$C_7$ alkyl or $C_3$-$C_7$ alkenyl; or phenyl, benzyl, each phenyl or benzyl optionally substituted by halogen, $C_1$-$C_4$ alkyl or $C_1$-$C_4$ haloalkyl.

Embodiment 70. A compound of Embodiment 69 wherein $R^9$ is H or $C_1$-$C_7$ alkyl; or benzyl optionally substituted by halogen, $C_1$-$C_4$ alkyl or $C_1$-$C_4$ haloalkyl.

Embodiment 71. A compound of Embodiment 70 wherein $R^9$ is $C_1$-$C_7$ alkyl; or benzyl optionally substituted by halogen, $C_1$-$C_4$ alkyl or $C_1$-$C_4$ haloalkyl.

Embodiment 72. A compound of any one of Embodiments 1 through 62 or 65 wherein $R^{10}$ is $C_1$-$C_7$ alkyl, $C_3$-$C_7$ alkenyl, $C_3$-$C_7$ cycloalkyl, $C_2$-$C_7$ haloalkyl or $C_3$-$C_7$ haloalkenyl; or phenyl, benzyl or a 6-membered heterocyclic ring, each phenyl, benzyl or heterocyclic ring optionally substituted by halogen, $C_1$-$C_4$ alkyl or $C_1$-$C_4$ haloalkyl.

Embodiment 73. A compound of Embodiment 72 wherein $R^{10}$ is $C_1$-$C_7$ alkyl or $C_3$-$C_7$ cycloalkyl; or phenyl or benzyl, each phenyl or benzyl optionally substituted by halogen, $C_1$-$C_4$ alkyl or $C_1$-$C_4$ haloalkyl.

Embodiment 74. A compound of Embodiment 73 wherein $R^{10}$ is $C_1$-$C_7$ alkyl; or phenyl optionally substituted by halogen, $C_1$-$C_4$ alkyl or $C_1$-$C_4$ haloalkyl.

Embodiment 75. A compound of Embodiment 74 wherein $R^{10}$ is $CH_3$, $CH_2CH_3$, $CH_2CH_2CH_3$, Ph, Ph(4-Cl), Ph(3-$CF_3$) or Ph(4-$CF_3$).

Embodiment 76. A compound of any one of Embodiments 1 through 75 wherein $R^{12}$ is H, $C_1$-$C_7$ alkyl, $C_2$-$C_7$ alkenyl, $C_2$-$C_7$ alkynyl or $C_3$-$C_7$ cycloalkyl.

Embodiment 77. A compound of Embodiment 76 wherein $R^{12}$ is H, $C_1$-$C_7$ alkyl or $C_3$-$C_7$ cycloalkyl.

Embodiment 78. A compound of any one of Embodiments 1 through 77 wherein $R^{13}$ is $C_1$-$C_4$ alkyl or $C_1$-$C_4$ alkoxy.

Embodiment 79. A compound of Embodiment 78 wherein $R^{13}$ is $C_1$-$C_2$ alkyl or $C_1$-$C_2$ alkoxy.

Embodiment 80. A compound of any one of Embodiments 1 through 79 wherein $R^{14}$ is $C_1$-$C_4$ alkyl or $C_1$-$C_4$ alkoxy.

Embodiment 81. A compound of Embodiment 80 wherein $R^{14}$ is $C_1$-$C_2$ alkyl or $C_1$-$C_2$ alkoxy.

Embodiments of this invention, including Embodiments 1-81 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-81 above as well as any other embodiments described herein, and any combination thereof, pertain to the compositions and methods of the present invention.

Embodiment A. A compound of Formula 1 wherein
$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_1$-$C_7$ haloalkyl, $C_2$-$C_7$ haloalkenyl, $C_2$-$C_7$ alkoxyalkyl or $C_1$-$C_7$ alkoxy;

$R^2$ is H, halogen, cyano, —CHO, $C_1$-$C_7$ alkyl, $C_3$-$C_8$ alkylcarbonylalkyl, $C_3$-$C_8$ alkoxycarbonylalkyl, $C_1$-$C_4$ alkylcarbonyl, $C_2$-$C_7$ alkylcarbonyloxy, $C_4$-$C_7$ alkylcycloalkyl, $C_3$-$C_7$ cycloalkyl, $C_4$-$C_7$ cycloalkylalkyl, $C_2$-$C_7$ haloalkoxyalkyl, $C_1$-$C_7$ haloalkyl, $C_2$-$C_7$ alkoxyalkyl, $C_1$-$C_7$ alkoxy, $C_1$-$C_5$ alkylthio or $C_2$-$C_3$ alkoxycarbonyl;

each $R^3$ is independently H, halogen, $C_1$-$C_5$ alkyl, $C_3$-$C_5$ cycloalkyl, $C_1$-$C_5$ haloalkyl, $C_1$-$C_5$ alkoxy or $C_1$-$C_5$ haloalkoxy;

n is 0 to 2;

$R^4$ is H, halogen, $C_1$-$C_3$ alkyl, $C_3$-$C_4$ cycloalkyl, $C_1$-$C_3$ haloalkyl or $C_1$-$C_3$ alkoxy;

L is a direct bond or $C_1$-$C_2$ alkanediyl;

G is H, C(=O)$R^9$, C(=S)$R^9$, $CO_2R^{10}$, C(=O)$SR^{10}$, CON($R^{11}$)($R^{12}$) or P(=O)($R^{13}$)($R^{14}$); or $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_3$-$C_6$ cycloalkyl or $C_4$-$C_7$ cycloalkylalkyl;

$R^9$ and $R^{11}$ are independently H, $C_1$-$C_7$ alkyl, $C_3$-$C_7$ alkenyl, $C_3$-$C_7$ alkynyl, $C_3$-$C_7$ cycloalkyl or $C_1$-$C_7$ haloalkyl; or phenyl, benzyl, or a 6-membered heterocyclic ring, each phenyl, benzyl or heterocyclic ring optionally substituted by halogen, $C_1$-$C_4$ alkyl or $C_1$-$C_4$ haloalkyl;

$R^{10}$ is $C_1$-$C_7$ alkyl, $C_3$-$C_7$ alkenyl, $C_3$-$C_7$ cycloalkyl, $C_2$-$C_7$ haloalkyl or $C_3$-$C_7$ haloalkenyl; or phenyl, benzyl or a 6-membered heterocyclic ring, each phenyl, benzyl or heterocyclic ring optionally substituted by halogen, $C_1$-$C_4$ alkyl or $C_1$-$C_4$ haloalkyl;

$R^{12}$ is H, $C_1$-$C_7$ alkyl, $C_2$-$C_7$ alkenyl, $C_2$-$C_7$ alkynyl or $C_3$-$C_7$ cycloalkyl;

$R^{13}$ is $C_1$-$C_4$ alkyl or $C_1$-$C_4$ alkoxy; and $R^{14}$ is $C_1$-$C_4$ alkyl or $C_1$-$C_4$ alkoxy.

Embodiment B. A compound of Embodiment A wherein
$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_7$ alkoxyalkyl or $C_1$-$C_7$ alkoxy;

$R^2$ is H, halogen, cyano, —CHO, $C_1$-$C_7$ alkyl, $C_4$-$C_7$ alkylcycloalkyl, $C_3$-$C_7$ cycloalkyl, $C_4$-$C_7$ cycloalkylalkyl, $C_2$-$C_7$ haloalkoxyalkyl, $C_1$-$C_7$ haloalkyl, $C_2$-$C_7$ alkoxyalkyl, $C_1$-$C_7$ alkoxy or $C_1$-$C_5$ alkylthio;

each $R^3$ is independently H, halogen, $C_1$-$C_5$ alkyl, $C_1$-$C_5$ haloalkyl, $C_1$-$C_5$ alkoxy or $C_1$-$C_5$ haloalkoxy;

n is 0 or 1;

$R^4$ is H, halogen, $C_1$-$C_2$ alkyl, cyclopropyl or $C_1$-$C_2$ haloalkyl;

L is a direct bond;

G is H, C(=O)$R^9$, $CO_2R^{10}$, CON($R^{11}$)($R^{12}$) or P(=O)($R^{13}$)($R^{14}$); or $C_1$-$C_4$ alkyl, $C_2$-$C_4$ alkenyl, $C_1$-$C_4$ haloalkyl, $C_2$-$C_4$ haloalkenyl, $C_2$-$C_4$ alkoxyalkyl, $C_3$-$C_6$ cycloalkyl or $C_4$-$C_7$ cycloalkylalkyl;

$R^9$ and $R^{11}$ are independently H, $C_1$-$C_7$ alkyl or $C_3$-$C_7$ alkenyl; or phenyl, benzyl, each phenyl or benzyl optionally substituted by halogen, $C_1$-$C_4$ alkyl or $C_1$-$C_4$ haloalkyl;

$R^{10}$ is $C_1$-$C_7$ alkyl or $C_3$-$C_7$ cycloalkyl; or phenyl or benzyl, each phenyl or benzyl optionally substituted by halogen, $C_1$-$C_4$ alkyl or $C_1$-$C_4$ haloalkyl;

$R^{12}$ is H, $C_1$-$C_7$ alkyl or $C_3$-$C_7$ cycloalkyl;
$R^{13}$ is $C_1$-$C_2$ alkyl or $C_1$-$C_2$ alkoxy; and
$R^{14}$ is $C_1$-$C_2$ alkyl or $C_1$-$C_2$ alkoxy.

Embodiment C. A compound of Embodiment B wherein
$R^1$ is H, $C_1$-$C_7$ alkyl, $C_4$-$C_7$ alkylcycloalkyl, $C_3$-$C_7$ cycloalkyl, $C_4$-$C_7$ cycloalkylalkyl or $C_2$-$C_7$ alkoxyalkyl;
$R^2$ is H, halogen, cyano, $C_1$-$C_7$ alkyl, $C_2$-$C_7$ haloalkoxyalkyl, $C_1$-$C_7$ haloalkyl, $C_2$-$C_7$ alkoxyalkyl, $C_1$-$C_7$ alkoxy or $C_1$-$C_5$ alkylthio;
each $R^3$ is independently H, halogen, methyl, ethyl, $CF_3$ or —$OCHF_2$;
$R^4$ is H, halogen, methyl, ethyl or $CF_3$;
G is H, C(=O)$R^9$, $CO_2R^{10}$ or P(=O)($R^{13}$)($R^{14}$); or $C_1$-$C_4$ alkyl, $C_1$-$C_4$ haloalkyl, $C_2$-$C_4$ alkoxyalkyl or $C_3$-$C_6$ cycloalkyl;
$R^9$ is H or $C_1$-$C_7$ alkyl; or benzyl optionally substituted by halogen, $C_1$-$C_4$ alkyl or $C_1$-$C_4$ haloalkyl; and
$R^{10}$ is $C_1$-$C_7$ alkyl; or phenyl optionally substituted by halogen, $C_1$-$C_4$ alkyl or $C_1$-$C_4$ haloalkyl.

Embodiment D. A compound of Embodiment C wherein
$R^1$ is H, $C_1$-$C_7$ alkyl, $C_3$-$C_7$ cycloalkyl, $C_4$-$C_7$ cycloalkylalkyl or $C_2$-$C_7$ alkoxyalkyl;
$R^2$ is H, halogen, cyano, $C_1$-$C_7$ alkyl, $C_1$-$C_7$ haloalkyl or $C_1$-$C_7$ alkoxy;
each $R^3$ is independently H, F, Cl, Br or methyl;
$R^4$ is H, F, Cl, Br or methyl;
$R^5$ is H or methyl;
$R^6$ is H or methyl;
$R^7$ is H or methyl;
$R^8$ is H or methyl;
G is H, C(=O)$R^9$ or $CO_2R^{10}$; or $C_2$-$C_4$ alkoxyalkyl or $C_3$-$C_6$ cycloalkyl;
$R^9$ is $C_1$-$C_7$ alkyl; or benzyl optionally substituted by halogen, $C_1$-$C_4$ alkyl or $C_1$-$C_4$ haloalkyl; and
$R^{10}$ is $CH_3$, $CH_2CH_3$, $CH_2CH_2CH_3$, Ph, Ph(4-Cl), Ph(3-$CF_3$) or Ph(4-$CF_3$).

Embodiment E. A compound of Embodiment D wherein
W is —C($R^7$)($R^8$)—;
$R^1$ is H, $C_1$-$C_7$ alkyl, $C_3$-$C_7$ cycloalkyl or $C_2$-$C_7$ alkoxyalkyl;
$R^2$ is H, Cl, Br, I, cyano, methyl, $CF_3$ or methoxy;
n is 0;
$R^4$ is methyl;
$R^5$ is H;
$R^6$ is H;
$R^7$ is H;
$R^8$ is H; and
G is H.

Embodiment F. A compound of Embodiment D wherein
W is —O—;
$R^1$ is H or $C_1$-$C_7$ alkyl;
$R^2$ is H, Cl, methyl or methoxy;
n is 0;
$R^4$ is methyl;
$R^5$ is H;
$R^6$ is H; and
G is H.

Specific Embodiments of the Invention are the following compounds of the Summary of the Invention:
4-(3,4-dihydro-2-methyl-1-naphthalenyl)-5-hydroxy-2,6-dimethyl-3-(2H)-pyridazinone; and
5-hydroxy-2,6-dimethyl-4-(3-methyl-2H-1-benzopyran-4-yl)-3-(2H)-pyridazinone.

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, 2-[(2, 4-dichlorophenyl)methyl]-4,4-dimethyl-3-isoxazolidinone, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenz-methyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, cyclopyranil, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimethyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, S-beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy] ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2(1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3 (2H)-pyridazinone.

HST inhibitors also include compounds of Formulae A and B.

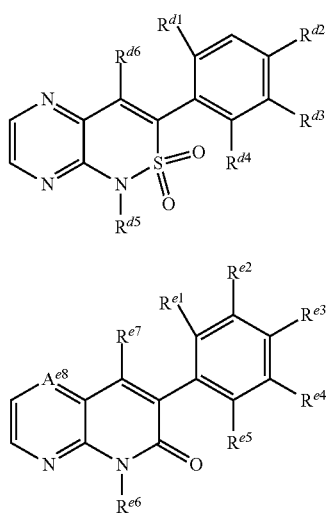

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben, [3-(3,5-dichlorophenyl)-1H-pyrazol-4-yl]phenyl-methanone and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, daimuron, 2-[(2,4-dichlorophenyl) methyl]-4,4-dimethyl-3-isoxazolidinone, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl) methoxy]methyl]-4,5-dihydro-5-methyl-3-(3-methyl-2-thienyl)isoxazole.

"Other herbicides" (b15) also include a compound of Formula (b15A)

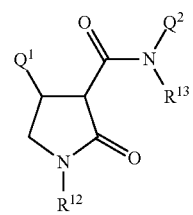

wherein $R^{12}$ is H, $C_1$-$C_6$ alkyl, $C_1$-$C_6$ haloalkyl or $C_4$-$C_8$ cycloalkyl;

$R^{13}$ is H, $C_1$-$C_6$ alkyl or $C_1$-$C_6$ alkoxy;

$Q^1$ is an optionally substituted ring system selected from the group consisting of phenyl, thienyl, pyridinyl, benzodioxolyl, naphthyl, naphthalenyl, benzofuranyl, furanyl, benzothiophenyl and pyrazolyl, wherein when substituted said ring system is substituted by 1 to 3 $R^{14}$;

$Q^2$ is an optionally substituted ring system selected from the group consisting of phenyl, pyridinyl, benzodioxolyl, pyridinonyl, thiadiazolyl, thiazolyl, and oxazolyl, wherein when substituted said ring system is substituted by 1 to 3 $R^{15}$;

each $R^{14}$ is independently halogen, $C_1$-$C_6$ alkyl, $C_1$-$C_6$ haloalkyl, $C_1$-$C_6$ alkoxy, $C_1$-$C_6$ haloalkoxy, $C_3$-$C_8$ cyaloalkyl, cyano, $C_1$-$C_6$ alkylthio, $C_1$-$C_6$ alkylsulfinyl, $C_1$-$C_6$ alkylsulfonyl, $SF_5$, $NHR^{17}$; or phenyl optionally substituted by 1 to 3 $R^{16}$; or pyrazolyl optionally substituted by 1 to 3 $R^{16}$;

each $R^{15}$ is independently halogen, $C_1$-$C_6$ alkyl, $C_1$-$C_6$ haloalkyl, $C_1$-$C_6$ alkoxy, $C_1$-$C_6$ haloalkoxy, cyano, nitro, $C_1$-$C_6$ alkylthio, $C_1$-$C_6$ alkylsulfinyl, $C_1$-$C_6$ alkylsulfonyl;

each $R^{16}$ is independently halogen, $C_1$-$C_6$ alkyl or $C_1$-$C_6$ haloalkyl;

$R^{17}$ is $C_1$-$C_4$ alkoxycarbonyl.

In one Embodiment wherein "other herbicides" (b15) also include a compound of Formula (b15A), it is preferred that $R^{12}$ is H or $C_1$-$C_6$ alkyl; more preferably $R^{12}$ is H or methyl. Preferably $R^{13}$ is H. Preferably $Q^1$ is either a phenyl ring or a pyridinyl ring, each ring substituted by 1 to 3 $R^{14}$; more preferably $Q^1$ is a phenyl ring substituted by 1 to 2 $R^{14}$. Preferably $Q^2$ is a phenyl ring substituted by 1 to 3 $R^{15}$; more preferably $Q^2$ is a phenyl ring substituted by 1 to 2 $R^{15}$. Preferably each $R^{14}$ is independently halogen, $C_1$-$C_4$ alkyl, $C_1$-$C_3$ haloalkyl, $C_1$-$C_3$ alkoxy or $C_1$-$C_3$ haloalkoxy; more preferably each $R^{14}$ is independently chloro, fluoro, bromo, $C_1$-$C_2$ haloalkyl, $C_1$-$C_2$ haloalkoxy or $C_1$-$C_2$ alkoxy. Preferably each $R^{15}$ is independently halogen, $C_1$-$C_4$ alkyl, $C_1$-$C_3$ haloalkoxy; more preferably each $R^{15}$ is independently chloro, fluoro, bromo, $C_1$-$C_2$ haloalkyl, $C_1$-$C_2$ haloalkoxy or $C_1$-$C_2$ alkoxy. Specifically preferred as "other herbicides" (b15) include any one of the following (b15A-1) through (b15A-15) wherein the stereochemistry at the 3- and 4-positions of the pyrrolidinone ring are preferably in the trans configuration relative to each other:

(b15A-1)
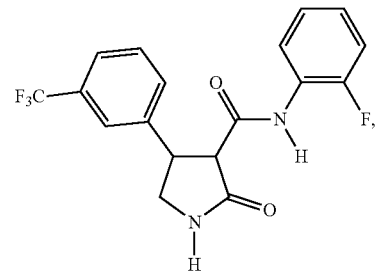

(b15A-2)
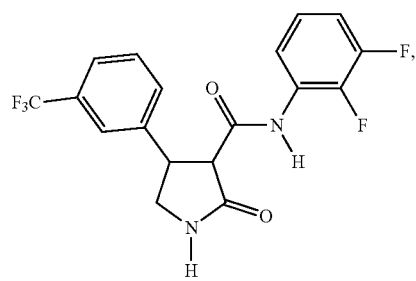

(b15A-3)
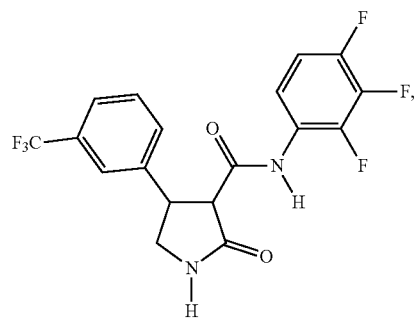

(b15A-4)
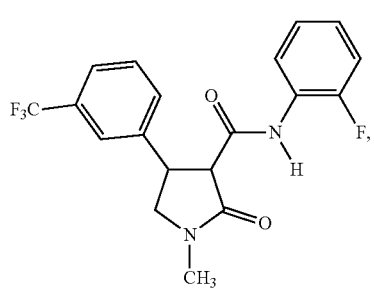

(b15A-5)
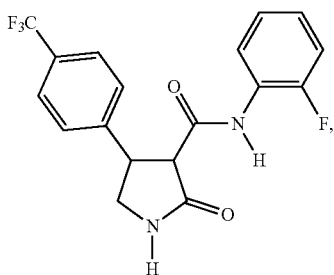

(b15A-6)
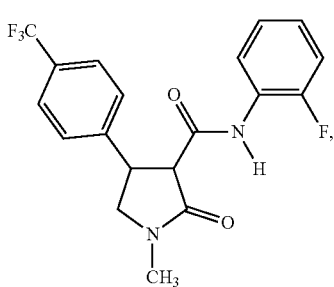

(b15A-7)
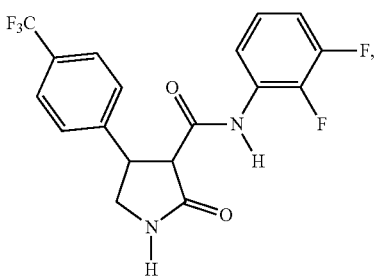

-continued

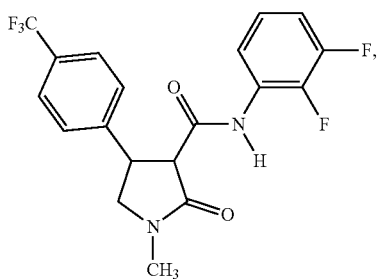
(b15A-8)

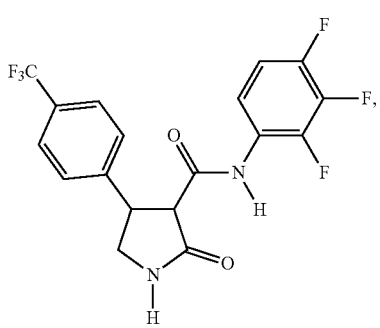
(b15A-9)

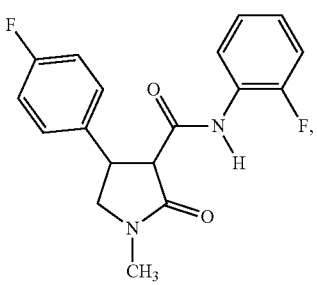
(b15A-10)

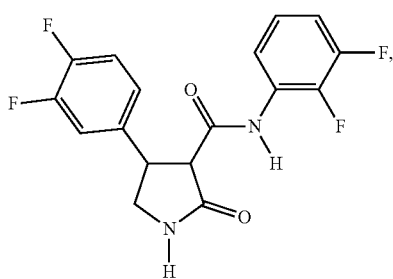
(b15A-11)

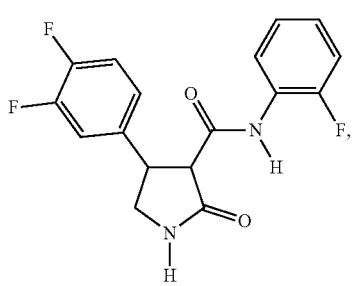
(b15A-12)

-continued

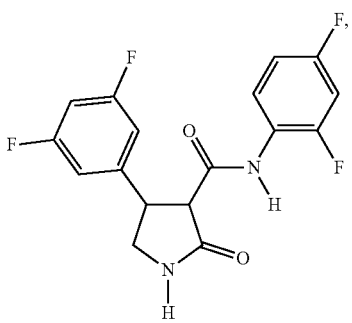
(b15A-13)

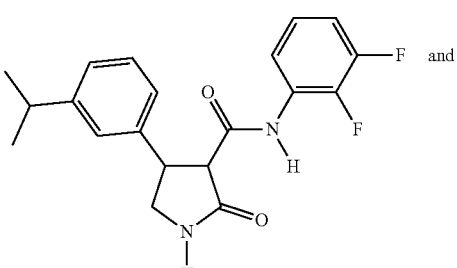
(b15A-14)

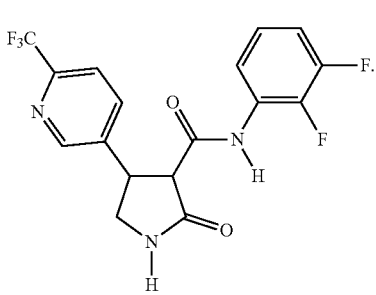
(b15A-15)

"Other herbicides" (b15) also include a compound of Formula (b15B)

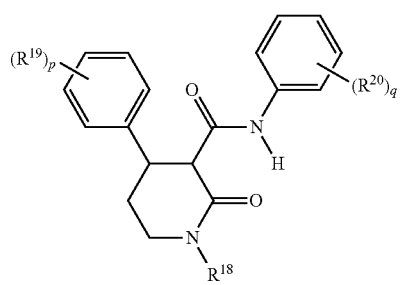
(b15B)

wherein
$R^{18}$ is H, $C_1$-$C_6$ alkyl, $C_1$-$C_6$ haloalkyl or $C_4$-$C_8$ cycloalkyl;
each $R^{19}$ is independently halogen, $C_1$-$C_6$ haloalkyl or $C_1$-$C_6$ haloalkoxy;
p is an integer of 0, 1, 2 or 3;
each $R^{20}$ is independently halogen, $C_1$-$C_6$ haloalkyl or $C_1$-$C_6$ haloalkoxy; and
q is an integer of 0, 1, 2 or 3.

In one Embodiment wherein "other herbicides" (b15) also include a compound of Formula (b15B), it is preferred that $R^{18}$ is H, methyl, ethyl or propyl; more preferably $R^{18}$ is H or methyl; most preferably $R^{18}$ is H. Preferably each $R^{19}$ is independently chloro, fluoro, $C_1$-$C_3$ haloalkyl or $C_1$-$C_3$ haloalkoxy; more preferably each $R^{19}$ is independently chloro, fluoro, $C_1$ fluoroalkyl (i.e. fluoromethyl, difluoromethyl or trifluoromethyl) or $C_1$ fluoroalkoxy (i.e. trifluoromethoxy, difluoromethoxy or fluoromethoxy). Preferably each $R^{20}$ is independently chloro, fluoro, $C_1$ haloalkyl or $C_1$ haloalkoxy; more preferably each $R^{20}$ is independently chloro, fluoro, $C_1$ fluoroalkyl (i.e. fluoromethyl, difluorormethyl or trifluromethyl) or $C_1$ fluoroalkoxy (i.e. trifluoromethoxy, difluoromethoxy or fluoromethoxy). Specifically preferred as "other herbicides" (b15) include any one of the following (b15B-1) through (b15B-19):

(b15B-1) 2-oxo-N-[2-(trifluoromethyl)phenyl]-4-(3,4-difluorophenyl)-3-piperidinecarboxamide,
(b15B-2) N-(2,3-difluorophenyl)-2-oxo-4-[3-(trifluoromethyl)phenyl]-3-piperidinecarboxamide,
(b15B-3) 2-oxo-N-[2-(trifluoromethyl)phenyl)]-4-[3-(trifluoromethyl)phenyl]-3-piperidinecarboxamide,
(b15B-4) N-(2-chlorophenyl)-2-oxo-4-[4-(trifluoromethyl)phenyl]-3-piperidinecarboxamide,
(b15B-5) N-(2-fluorophenyl)-2-oxo-4-[4-(trifluoromethyl)phenyl]-3-piperidinecarboxamide,
(b15B-6) (3R,4S)—N-(2,3-difluorophenyl)-2-oxo-4-[3-(trifluoromethyl)phenyl]-3-piperidinecarboxamide,
(b15B-7) (3R,4S)—N-(2,3-difluorophenyl)-2-oxo-4-[4-(trifluoromethyl)phenyl]-3-piperidinecarboxamide,
(b15B-8) (3R,4S)—N-(3-chloro-2-fluorophenyl)-2-oxo-4-[3-(trifluoromethyl)phenyl]-3-piperidinecarboxamide,
(b15B-9) (3R,4S)-2-oxo-4-[3-(trifluoromethyl)phenyl]-N-[2,3,4-trifluorophenyl]-3-piperidinecarboxamide,

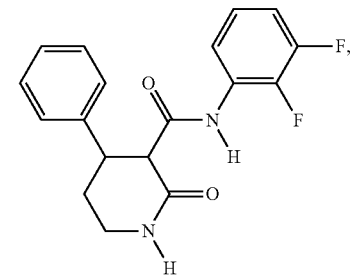
(b15B-10)

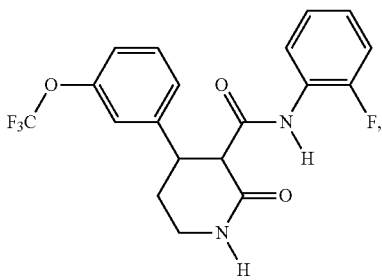
(b15B-11)

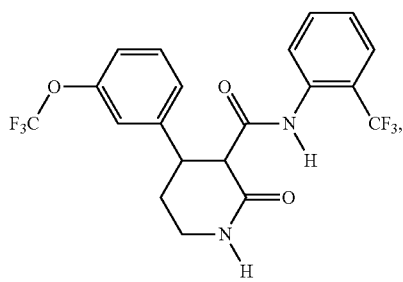
(b15B-12)

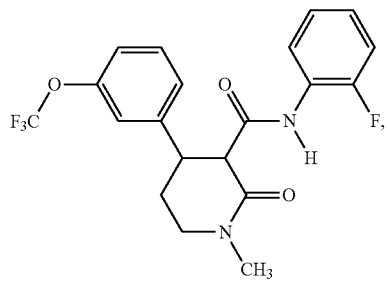
(b15B-13)

(b15B-14) (3R,4S)-4-(3-chlorophenyl)-N-(2,3-difluorophenyl)-2-oxo-3-piperidinecarboxamide,
(b15B-15) 4-[3-(difluoromethyl)phenyl]-N-(2,3,4-trifluorophenyl)-2-oxo-piperidinecarboxamide,
(b15B-16) 4-[3-(difluoromethyl)phenyl]-N-(2-fluorophenyl)-2-oxo-piperidinecarboxamide,
(b15B-17) 4-[3-(difluoromethyl)phenyl]-N-(2,3-difluorophenyl)-2-oxo-3-piperidinecarboxamide,
(b15B-18) (3S,4S)—N-(2,3-difluorophenyl)-4-(4-fluorophenyl)-1-methyl-2-oxo-3-piperidinecarboxamide and
(b15B-19) (3R,4S)-2-oxo-N-[2-(trifluoromethyl)phenyl]-4-(4-fluorophenyl)-3-piperidinecarboxamide.

"Other herbicides" (b15) also include a compound of Formula (b15C),

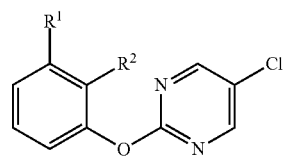
(b15C)

wherein $R^1$ is Cl, Br or CN; and $R^2$ is C(=O)$CH_2CH_2CF_3$, $CH_2CH_2CH_2CF_3$ or 3-$CHF_2$-isoxazol-5-yl.

"Other herbicides" (b15) also include a compound of Formula (b15D)

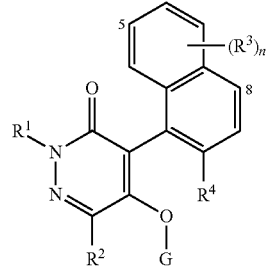
(b15D)

wherein $R^1$ is $CH_3$, $R^2$ is Me, $R^4$ is $OCHF_2$, G is H, and n is 0; $R^1$ is $CH_3$, $R^2$ is Me, $R^3$ is 5-F, $R^4$ is Cl, G is H, and n is 1; $R^1$ is $CH_3$, $R^2$ is Cl, $R^4$ is Me, G is H, and n is 0; $R^1$ is $CH_3$, $R^2$ is Me, $R^4$ is Cl, G is H, and n is 0; $R^1$ is $CH_3$, $R^2$ is Me, $R^3$ is 5-Me, $R^4$ is $OCHF_2$, G is H, and n is 1; $R^1$ is $CH_3$, $R^2$ is Me, $R^3$ is 5-Br, $R^4$ is $OCHF_2$, G is H, and n is 1; $R^1$ is $CH_3$, $R^2$ is Me, $R^3$ is 5-Cl, $R^4$ is Cl, G is H, and n is 1; and $R^1$ is $CH_3$, $R^2$ is $CH_3$, $R^4$ is $OCHF_2$, G is C(O)Me, and n is 0.

"Other herbicides" (b15) also include a compound of Formula (b15E)

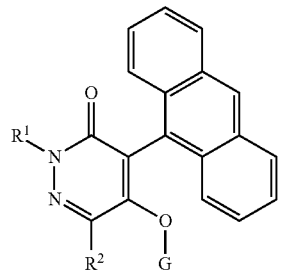

(b15E)

wherein

R$^1$ is CH$_3$, R$^2$ is Cl, and G is H; and

R$^1$ is CH$_3$, R$^2$ is Cl, and G is C(O)Me.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide.

The compounds of Formula 1 can be prepared by general methods known in the art of synthetic organic chemistry. One or more of the following methods and variations as described in Schemes 1-6 can be used to prepare a compound of Formula 1. The definitions of W, R$^1$, R$^2$, R$^3$, n, R$^4$, R$^5$, R$^6$, L and G in the compounds of Formulae 1-8 below are as defined above in the Summary of the Invention unless otherwise noted. Compounds of Formulae 1a and 1b are various subsets of the compounds of Formula 1, and all substituents for Formulae 1a and 1b are as defined above for Formula 1 unless otherwise noted.

As shown in Scheme 1, pyridazinones of Formula 1a can be made by reacting substituted 5-hydroxy-3(2H)-pyridazinones of Formula 1b with a suitable electrophilic reagent of Formula 2 in the presence of base in an appropriate solvent. Some examples of reagent classes representing Formula 2 wherein Z$^1$ is Cl and L is a direct bond include acid chlorides (G is —(C═O)R$^5$), carboxylates (G is —CO$_2$R$^6$), carbamoyl chlorides (G is —CONR$^7$R$^8$), sulfonyl chlorides (G is —S(O)$_2$R$^5$) and chlorosulfonamides (G is —S(O)$_2$NR$^7$R$^8$).

Examples of suitable bases for this reaction include, but are not limited to, potassium carbonate, sodium hydroxide, potassium hydroxide, sodium hydride or potassium tert-butoxide and, depending on the specific base used, appropriate solvents can be protic or aprotic and used anhydrous or as aqueous mixtures. Preferred solvents for this reaction include acetonitrile, methanol, ethanol, tetrahydrofuran, diethyl ether, 1,2-dimethoxyethane, dioxane, dichloromethane or N,N-dimethylformamide. The reaction can be performed at a range of temperatures, typically ranging from 0° C. to the reflux temperature of the solvent.

Scheme 1

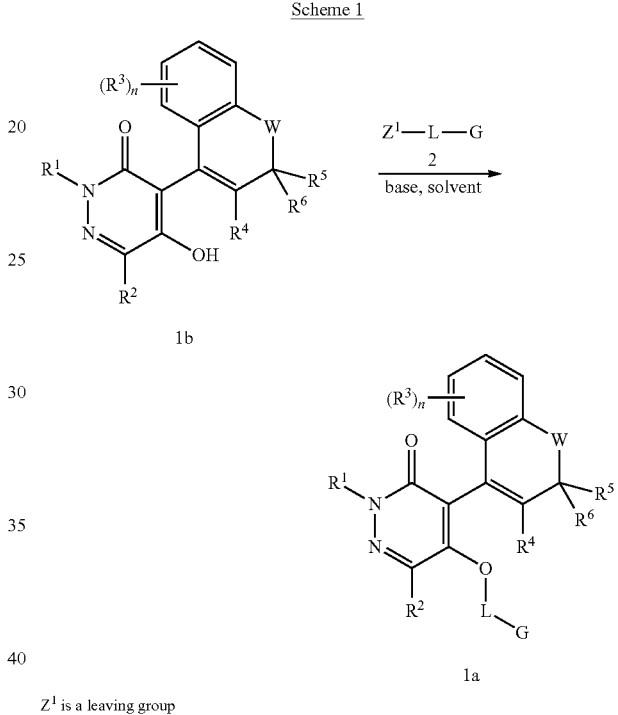

Z$^1$ is a leaving group

As shown in Scheme 2 compounds of the Formula 1b can be prepared via dealkylation of a compound of Formula 2, where R is a lower alkyl group. Dealkylation reagents such as boron tribromide, lithium chloride, or morpholine are suitable for this transformation (see, for example, WO 2009/086041, WO 2013/160126 and WO 2013/050421).

Scheme 2

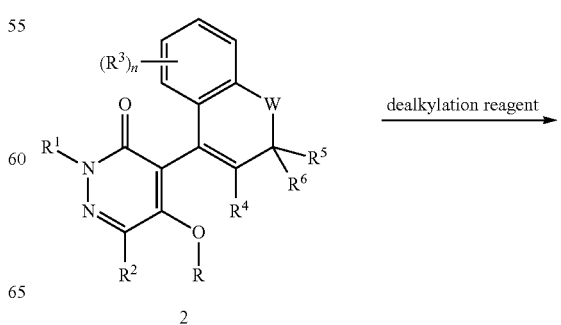

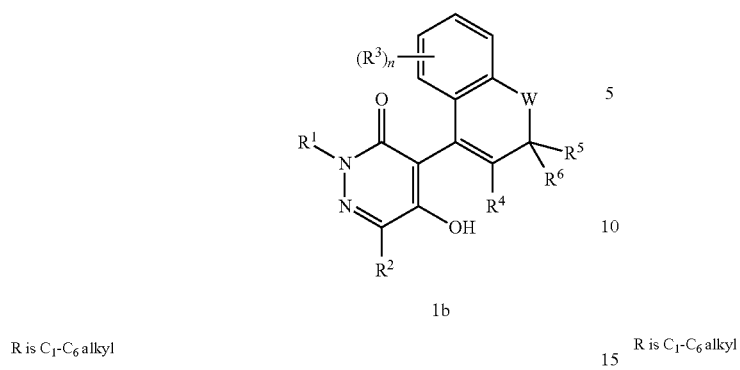

1b

R is $C_1$-$C_6$ alkyl

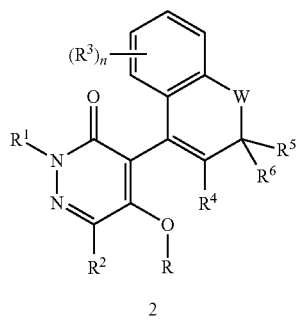

2

R is $C_1$-$C_6$ alkyl

A compound of Formula 2 can be prepared by coupling reactions of organometallic pyridazinone coupling partners of Formula 3 with a saturated bicyclic halide and sulfonate of Formula 4 as is shown in Scheme 3. The organometallic coupling partner can be, for example, an organozinc, organomagnesium, organotin, or organoboron reagent. Palladium catalysts such as palladium tetrakis (triphenylphosphine) and those generated from other palladium sources, such as $Pd_2dba_3$ and $Pd(OAc)_2$, and a phosphine or N-heterocyclic carbene ligand can be used in the coupling procedures (Maes et al. *J. Org. Chem.* 2011, 76, 9648-9659). Palladium precatalysts based on dialkyl biarylphosphine ligands, such as X-Phos, S-Phos and Ru-Phos (Buchwald et al. *Angew. Chem. Int. Ed.* 2013, 52(2), 615-619), or precatalysts derived from N-heterocyclic carbene ligands such as PEPPSI-i-Pr and PEPPSI-i-Pent (Organ et al. *Eur. J. Org. Chem.* 2010, 4343-4354) can affect this coupling as well. The reaction can be carried out in solvents such as tetrahydrofuran, dimethoxyethane, N-methyl-2-pyrrolidone and dioxane. Coupling partners may be either heterocyclic halides or sulfonates. A particularly useful class of coupling partners for the reaction are those based on nonaflates ($-OSO_2C_4F_9$) of saturated bicyclic compounds.

As seen in Scheme 4 a compound of Formula 3 can be prepared by metalation at the 4-position of a pyridazinone of Formula 5. Zincation can be accomplished with reagents such as 2,2,6,6-bis(tetramethylpiperidine)zinc, magnesium chloride, lithium chloride complex in toluene/tetrahydrofuran (i.e. Zn(TMP)-LiCl or $Zn(TMP)_2$—$MgCl_2$—LiCl). Magnesiation of this position can also be accomplished by treatment with Mg(TMP)-LiCl. See Verhelst, T., Ph.D. thesis, University of Antwerp, 2012 for conditions for pyridazinone metallation and for palladium catalyzed cross-coupling of 4-zincated and 4-magnesiated pyridazinones. The synthesis and cross-coupling conditions for 4-stannylpyridazinones are known from Stevenson et. al. *J. Het. Chem.* 2005, 42, 427.

Scheme 4

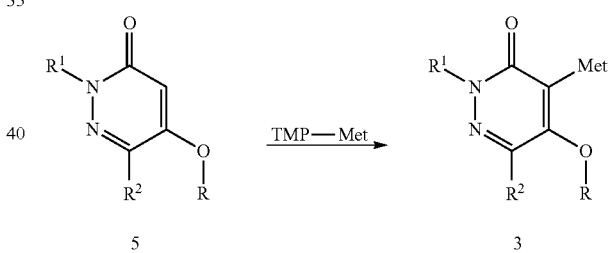

Compounds of Formula 4 where X is a halide or sulfonate can be prepared from ketones of Formula 6 as shown in Scheme 5. Dehydration/halogenation can be accomplished with such reagents as phosphorous oxychloride, phosphorous oxybromide, phosphorous pentachloride, or phosphorous tribromide. These reactions can be performed neat or in a variety of solvents such as dichloromethane, dichloroethane or chlorobenzene at temperatures ranging from 0 to 120° C. See *Organic Letters* 2003, 5(19), 3387-3390 where the sulfonylation can be accomplished with such reagents as methanesulfonyl chloride, trifluoromethanesulfonic anhydride, or perflouro-1-butanesulfonyl fluoride. The reaction can be performed in the presence of a suitable base which includes but is not limited to, lithium diisopropylamide, lithium hexamethyldisilizide, sodium hydride, pyridine or triethylamine in an appropriate solvent such as N,N-dimethylformamide, tetrahydrofuran, dioxane, or dichloromethane. These reactions are performed at temperatures ranging from −78° C. to room temperature. See *J. Org. Chem.* 2015, 80(22), 11618-11623.

Scheme 3

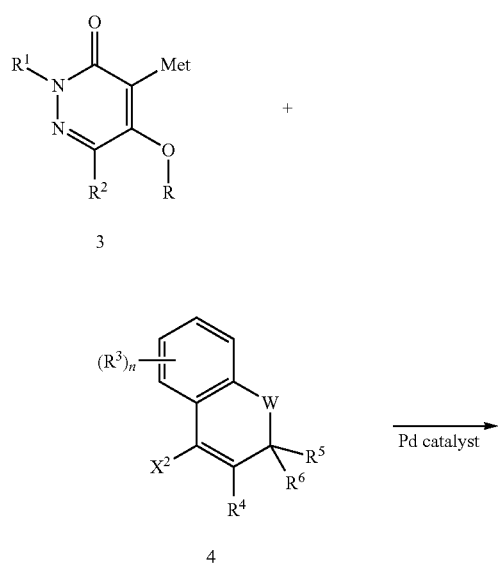

Scheme 5

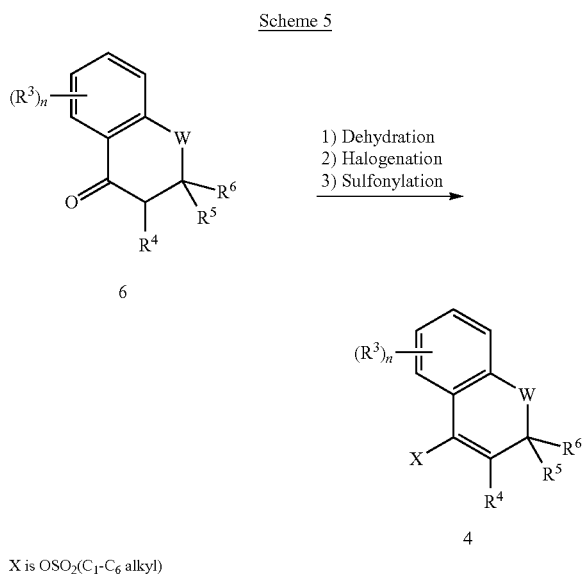

X is OSO$_2$(C$_1$-C$_6$ alkyl)

The R$^2$ substitutent of compounds of Formula 5, wherein R$^2$ is alkyl, cycloalkyl or substituted alkyl can be prepared by transition metal catalyzed reactions with a compound of Formula 7 as shown in Scheme 6. For reviews of these types of reactions, see: E. Negishi, *Handbook of Organopalladium Chemistry for Organic Synthesis*, John Wiley and Sons, Inc., New York, 2002, N. Miyaura, *Cross-Coupling Reactions: A Practical Guide*, Springer, New York, 2002, H. C. Brown et al., Organic Synthesis via Boranes, Aldrich Chemical Co., Milwaukee, Vol. 3, 2002, Suzuki et al., *Chemical Reviews* 1995, 95, 2457-2483 and Molander et al., *Accounts of Chemical Research* 2007, 40, 275-286. Also see *Tetrahedron Organic Chemistry Series Vol. 26: Palladium in Heterocyclic Chemistry*, 2$^{nd}$ Ed., Gribble and Li, editors, Elsevier, Amsterdam, 2007. For a review of Buchwald-Hartwig chemistry see Yudin and Hartwig, *Catalyzed Carbon-Heteroatom Bond Formation*, 2010, Wiley, New York. Related synthetic methods for the introduction of other functional groups at the R$^2$ position of Formula 5 are known in the art. Copper catalyzed reactions are useful for introducing the CF$_3$ group. For a comprehensive recent review of reagents for this reaction see Wu, Neumann and Beller in *Chemistry: An Asian Journal* 2012, ASAP, and references cited therein. For the introduction of a sulfur-containing substitutent at this position, see methods disclosed in WO 2013/160126. For the introduction of a cyano group at this position, see WO 2014/031971. For the introduction of a nitro group, see *J. Am. Chem. Soc.* 2009, 12898. For introduction of a fluoro substituent, see *J. Am. Chem. Soc.* 2014, 3792.

Scheme 6

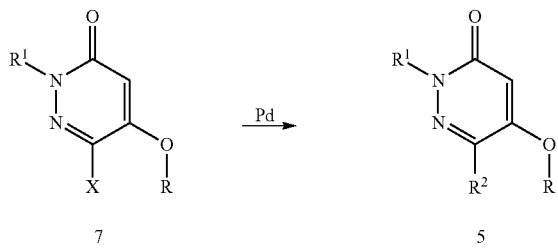

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. $^1$H NMR spectra are reported in ppm downfield from tetramethylsilane in CDCl$_3$; "s" means singlet, "d" means doublet, and "m" means multiplet.

EXAMPLE 1

Synthesis of 4-(3,4-dihydro-2-methyl-1-naphthalenyl)-5-methoxy-2,6-dimethyl-3(2H)-pyridazinone (Compound 1)

Step A: Preparation of 3,4-dihydro-2-methyl-1-naphthalenyl-1,1,2,2,3,3,4,4,4-nonafluoro-1-butanesulfonate To a solution of 2-methyl-1-tetralone (0.5 g, 3.1 mmol) in tetrahydrofuran (15 mL) at −78° C. was added lithium bis(trimethylsilyl)amide (1 M in tetrahydrofuran 3.7 mL, 3.7 mmol). The reaction mixture was stirred for 30 min. then perflouro-1-butanesulfonyl fluoride (1.2 g, 4.0 mmol) was added, and the resulting solution was allowed to warm to ambient temperature. After 30 min. the mixture was concentrated onto Celite® diatomaceaous earth filter aid and purified via silica gel chromatography using a gradient of ethyl acetate in hexanes as eluent to provide 0.97 g of the title compound.

$^1$H NMR δ 7.30-7.34 (m, 1H), 7.17-7.29 (m, 2H), 7.12-7.17 (m, 1H), 2.85 (m, 2H), 2.44 (m, 2H), 2.00 (s, 3H).

Step B: Preparation of 4-(3,4-dihydro-2-methyl-1-naphthalenyl)-5-methoxy-2,6-dimethyl-3(2H)-pyridazinone A reaction vessel was purged with nitrogen and charged with 5-methoxy-2,6-dimethyl-3(2H)-pyridazinone (0.2 g, 1.3 mmol), 3,4-dihydro-2-methyl-1-naphthalenyl-1,1,2,2,3,3,4,4,4-nonafluoro-1-butanesulfonate (i.e. the compound from Step A) (0.57 g, 1.3 mmol), SPhos pre-catalyst-G2 (chloro(2-dicyclohexylphosphino-2',6'-dimethoxy-1,1'-biphenyl) [2-(2'-amino-1,1'-biphenyl)]palladium(II), (0.05 g, 0.07 mmol), and tetrahydrofuran (5 mL). Bis(2,2,6,6-tetramethylpiperidinyl)zinc, lithium chloride, magnesium chloride complex (1.6 mL, 1.6 mmol) was added and the solution was heated at 50° C. overnight. The resulting mixture was concentrated onto Celite® diatomaceaous earth filter aid and purified via silica gel chromatography eluting with a gradient of ethyl acetate in hexanes to provide 0.32 g of the title compound, a compound of the invention.

$^1$H NMR δ 7.11-7.15 (m, 1H), 7.06-7.11 (m, 2H), 6.71-6.76 (m, 1H), 3.71 (d, 6H), 2.99-3.04 (m, 1H), 2.78-2.83 (m, 1H), 2.34-2.48 (m, 2H), 2.28 (s, 3H), 1.77 (s, 3H).

EXAMPLE 2

Synthesis of 4-(3,4-dihydro-2-methyl-1-naphthalenyl)-5-hydroxy-2,6-dimethyl-3(2H)-pyridazinone (Compound 2)

Step A: Preparation of 4-(3,4-dihydro-2-methyl-1-naphthalenyl)-5-hydroxy-2,6-dimethyl-3(2H)-pyridazinone A solution of the 4-(3,4-dihydro-2-methyl-1-naphthalenyl)-5-methoxy-2,6-dimethyl-3(2H)-pyridazinone (i.e. the product from Step B above) (0.2 g, 0.68 mmol) and morpholine (2 mL) were heated at 120° C. for 40 min. The resulting solution was cooled to ambient temperature and 1 N aqueous hydrochloric acid (50 mL) and isopropanol (0.5 mL) were added. The resulting mixture was stirred for 10 min and the resulting solid that formed was filtered and washed with water. The solid was dried under vacuum to give 0.16 g of the title compound, a compound of the invention.

$^1$H NMR δ 7.03-7.17 (m, 3H), 6.66-6.75 (m, 1H), 5.50 (s, 1H), 3.75 (s, 3H), 2.94-3.05 (m, 1H), 2.79-2.90 (m, 1H), 2.39-2.56 (m, 2H), 2.33 (s, 3H), 1.80 (s, 3H).

EXAMPLE 3

Synthesis of 5-hydroxy-2,6-dimethyl-4-(3-methyl-2H-1-benzopyran-4-yl)-3(2H)-pyridazinone (Compound 3)

Step A: Preparation of 3-methyl-2H-1-benzopyran-4-yl 1,1,2,2,3,3,4,4,4-nonafluoro-1-butanesulfonate To a solution of 3-methyl-4-chromanone (1.0 g, 6.2 mmol) in tetrahydrofuran (12 mL) at −78° C. was added lithium bis(trimethylsilyl)amide (1 M in tetrahydrofuran, 3.7 mL, 3.7 mmol). The reaction was stirred for 10 min then perflouro-1-butanesulfonyl fluoride (2.6 g, 8.7 mmol) was added, and the resulting mixture was allowed to warm to ambient temperature. After 30 min the mixture was concentrated onto Celite® diatomaceaous earth filter aid, and purified via silica gel chromatography with ethyl acetate in hexanes as eluent to provide 1.2 g of the title compound.

$^1$H NMR δ 7.16-7.24 (m, 2H), 6.93-7.00 (m, 1H), 6.81-6.86 (m, 1H), 4.81 (s, 2H), 1.86-1.92 (m, 3H).

Step B: Preparation of 5-methoxy-2,6-dimethyl-4-(3-methyl-2H-1-benzopyran-4-yl)-3(2H)-pyridazinone A reaction vessel was purged with nitrogen and charged with 5-methoxy-2,6-dimethyl-3(2H)-pyridazinone (0.2 g, 1.3 mmol), 3-methyl-2H-1-benzopyran-4-yl 1,1,2,2,3,3,4,4,4-nonafluoro-1-butanesulfonate (i.e. the product from Step A) (0.58 g, 1.3 mmol), SPhos pre-catalyst-G2 (chloro(2-dicyclohexylphosphino-2',6'-dimethoxy-1,1'-biphenyl)[2-(2'-amino-1,1'-biphenyl)]palladium(II), 0.05 g, 0.07 mmol), and tetrahydrofuran (5 mL). Bis(2,2,6,6-tetramethylpiperidinyl)zinc, lithium chloride, magnesium chloride complex (1.6 mL, 1.6 mmol) was added and the solution was heated at 50° C. overnight. The resulting mixture was concentrated onto Celite® diatomaceaous earth filter aid and purified via silica gel chromatography eluting with ethyl acetate in hexanes to provide 0.40 g of the title compound.

$^1$H NMR δ 7.04-7.11 (m, 1H), 6.80-6.86 (m, 2H), 6.67-6.72 (m, 1H), 4.87 (d, 1H), 4.71 (d, 1H), 3.71-3.78 (m, 6H), 2.28 (s, 3H), 1.67 (s, 3H).

Step C: Preparation of 5-hydroxy-2,6-dimethyl-4-(3-methyl-2H-1-benzopyran-4-yl)-3(2H)-pyridazinone A solution of 5-methoxy-2,6-dimethyl-4-(3-methyl-2H-1-benzopyran-4-yl)-3(2H)-pyridazinone (i.e. the product from Step B) (0.25 g, 0.88 mmol) and morpholine (2 mL) were heated at 120° C. for 30 min. The solution was concentrated to dryness in vacuo and 1 N aqueous hydrochloric acid (50 mL) and isopropanol (0.5 mL) were added. The resulting mixture was stirred for 10 min and the solid was filtered and washed with water. The solid was dried under vacuum to give 0.20 g of the title compound, a compound of the invention.

$^1$H NMR δ 7.03-7.11 (m, 1H), 6.76-6.83 (m, 2H), 6.63-6.68 (m, 1H), 4.82 (d, 1H), 4.64 (d, 1H), 3.70 (s, 3H), 2.31 (s, 3H), 1.60 (s, 3H).

By the procedures described herein together with methods known in the art, the following compounds of Tables 1 to 959 can be prepared. The following abbreviations are used in the Tables which follow: Me means methyl, Et means ethyl, Pr means propyl, i-Pr means isopropyl, t-Bu means tertiarybutyl, OMe means methoxy, OEt means ethoxy, SMe means methylthio, SEt means ethylthio, —CN means cyano, and SO$_2$Me means methylsulfonyl. A "-" in the (R$^3$)$_n$ column means n=0.

TABLE 1

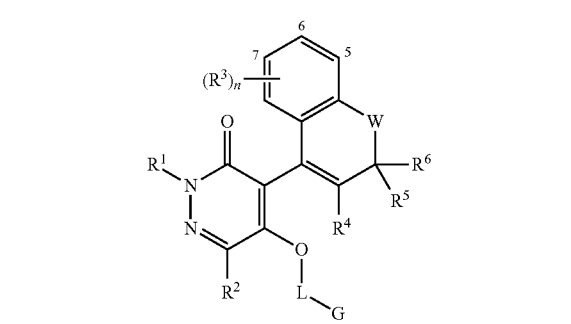

W is —CH$_2$—, R$^1$ is Me, R$^2$ is Me, R$^5$ is H, R$^6$ is H, L—G is H and

| (R$^3$)$_n$ | R$^4$ | (R$^3$)$_n$ | R$^4$ | (R$^3$)$_n$ | R$^4$ |
|---|---|---|---|---|---|
| — | H | 5-Pr | H | 6-CN | H |
| 5-Me | H | 6-Pr | H | 7-CN | H |
| 6-Me | H | 7-Pr | H | 5-CF$_3$ | H |
| 7-Me | H | 5-OMe | H | 6-CF$_3$ | H |
| 5-Et | H | 6-OMe | H | 7-CF$_3$ | H |
| 6-Et | H | 7-OMe | H | 5-F | H |
| 7-Et | H | 5-CN | H | 6-F | H |
| 7-F | H | 7-CN | Pr | 7-Pr | Br |
| 5-Cl | H | 5-CF$_3$ | Pr | 5-OMe | Br |
| 6-Cl | H | 6-CF$_3$ | Pr | 6-OMe | Br |
| 7-Cl | H | 7-CF$_3$ | Pr | 7-OMe | Br |
| 5-Br | H | 5-F | Pr | 5-CN | Br |
| 6-Br | H | 6-F | Pr | 6-CN | Br |
| 7-Br | H | 7-F | Pr | 7-CN | Br |
| 5-OCHF$_2$ | H | 5-Cl | Pr | 5-CF$_3$ | Br |
| 6-OCHF$_2$ | H | 6-Cl | Pr | 6-CF$_3$ | Br |
| 7-OCHF$_2$ | H | 7-Cl | Pr | 7-CF$_3$ | Br |
| 6,7-di-Me | H | 5-Br | Pr | 5-F | Br |
| 5,7-di-Me | H | 6-Br | Pr | 6-F | Br |
| 5-Cl, 7-Me | H | 7-Br | Pr | 7-F | Br |
| 5-Cl, 7-OMe | H | 5-OCHF$_2$ | Pr | 5-Cl | Br |
| 5-F, 7-Me | H | 6-OCHF$_2$ | Pr | 6-Cl | Br |
| 5-Me, 7-F | H | 7-OCHF$_2$ | Pr | 7-Cl | Br |
| 5-Me, 7-Cl | H | 6,7-di-Me | Pr | 5-Br | Br |
| 5-Me, 7-CN | H | 5,7-di-Me | Pr | 6-Br | Br |
| 5-Me, 7-OMe | H | 5-Cl, 7-Me | Pr | 7-Br | Br |
| 5,7-di-F | H | 5-Cl, 7-OMe | Pr | 5-OCHF$_2$ | Br |
| 5,7-di-Cl | H | 5-F, 7-Me | Pr | 6-OCHF$_2$ | Br |
| 5,7-di-Br | H | 5-Me, 7-F | Pr | 7-OCHF$_2$ | Br |
| — | Pr | 5-Me, 7-Cl | Pr | 6,7-di-Me | Br |
| 5-Me | Pr | 5-Me, 7-CN | Pr | 5,7-di-Me | Br |
| 6-Me | Pr | 5-Me, 7-OMe | Pr | 5-Cl, 7-Me | Br |
| 7-Me | Pr | 5,7-di-F | Pr | 5-Cl, 7-OMe | Br |
| 5-Et | Pr | 5,7-di-Cl | Pr | 5-F, 7-Me | Br |
| 6-Et | Pr | 5,7-di-Br | Pr | 5-Me, 7-F | Br |
| 7-Et | Pr | — | Br | 5-Me, 7-Cl | Br |
| 5-Pr | Pr | 5-Me | Br | 5-Me, 7-CN | Br |
| 6-Pr | Pr | 6-Me | Br | 5-Me, 7-OMe | Br |
| 7-Pr | Pr | 7-Me | Br | 5,7-di-F | Br |
| 5-OMe | Pr | 5-Et | Br | 5,7-di-Cl | Br |
| 6-OMe | Pr | 6-Et | Br | 5,7-di-Br | Br |
| 7-OMe | Pr | 7-Et | Br | — | OMe |
| 5-CN | Pr | 5-Pr | Br | 5-Me | OMe |
| 6-CN | Pr | 6-Pr | Br | 6-Me | OMe |
| 7-Me | OMe | 5,7-di-F | OMe | 5-Cl, 7-OMe | SCHF$_2$ |
| 5-Et | OMe | 5,7-di-Cl | OMe | 5-F, 7-Me | SCHF$_2$ |
| 6-Et | OMe | 5,7-di-Br | OMe | 5-Me, 7-F | SCHF$_2$ |
| 7-Et | OMe | — | SCHF$_2$ | 5-Me, 7-Cl | SCHF$_2$ |
| 5-Pr | OMe | 5-Me | SCHF$_2$ | 5-Me, 7-CN | SCHF$_2$ |
| 6-Pr | OMe | 6-Me | SCHF$_2$ | 5-Me, 7-OMe | SCHF$_2$ |
| 7-Pr | OMe | 7-Me | SCHF$_2$ | 5,7-di-F | SCHF$_2$ |
| 5-OMe | OMe | 5-Et | SCHF$_2$ | 5,7-di-Cl | SCHF$_2$ |
| 6-OMe | OMe | 6-Et | SCHF$_2$ | 5,7-di-Br | SCHF$_2$ |
| 7-OMe | OMe | 7-Et | SCHF$_2$ | — | Me |
| 5-CN | OMe | 5-Pr | SCHF$_2$ | 5-Me | Me |
| 6-CN | OMe | 6-Pr | SCHF$_2$ | 6-Me | Me |
| 7-CN | OMe | 7-Pr | SCHF$_2$ | 7-Me | Me |
| 5-CF$_3$ | OMe | 5-OMe | SCHF$_2$ | 5-Et | Me |
| 6-CF$_3$ | OMe | 6-OMe | SCHF$_2$ | 6-Et | Me |
| 7-CF$_3$ | OMe | 7-OMe | SCHF$_2$ | 7-Et | Me |

TABLE 1-continued

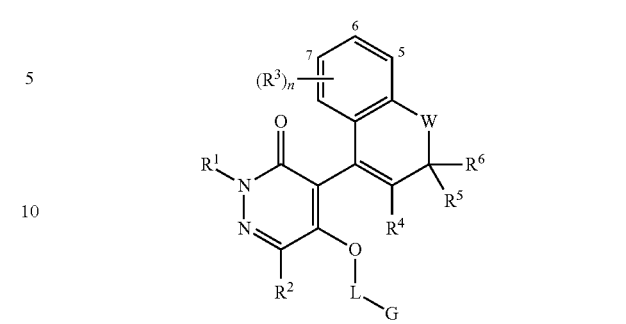

W is —CH$_2$—, R$^1$ is Me, R$^2$ is Me, R$^5$ is H, R$^6$ is H, L—G is H and

| (R$^3$)$_n$ | R$^4$ | (R$^3$)$_n$ | R$^4$ | (R$^3$)$_n$ | R$^4$ |
|---|---|---|---|---|---|
| 5-F | OMe | 5-CN | SCHF$_2$ | 5-Pr | Me |
| 6-F | OMe | 6-CN | SCHF$_2$ | 6-Pr | Me |
| 7-F | OMe | 7-CN | SCHF$_2$ | 7-Pr | Me |
| 5-Cl | OMe | 5-CF$_3$ | SCHF$_2$ | 5-OMe | Me |
| 6-Cl | OMe | 6-CF$_3$ | SCHF$_2$ | 6-OMe | Me |
| 7-Cl | OMe | 7-CF$_3$ | SCHF$_2$ | 7-OMe | Me |
| 5-Br | OMe | 5-F | SCHF$_2$ | 5-CN | Me |
| 6-Br | OMe | 6-F | SCHF$_2$ | 6-CN | Me |
| 7-Br | OMe | 7-F | SCHF$_2$ | 7-CN | Me |
| 5-OCHF$_2$ | OMe | 5-Cl | SCHF$_2$ | 5-CF$_3$ | Me |
| 6-OCHF$_2$ | OMe | 6-Cl | SCHF$_2$ | 6-CF$_3$ | Me |
| 7-OCHF$_2$ | OMe | 7-Cl | SCHF$_2$ | 7-CF$_3$ | Me |
| 6,7-di-Me | OMe | 5-Br | SCHF$_2$ | 5-F | Me |
| 5,7-di-Me | OMe | 6-Br | SCHF$_2$ | 6-F | Me |
| 5-Cl, 7-Me | OMe | 7-Br | SCHF$_2$ | 7-F | Me |
| 5-Cl, 7-OMe | OMe | 5-OCHF$_2$ | SCHF$_2$ | 5-Cl | Me |
| 5-F, 7-Me | OMe | 6-OCHF$_2$ | SCHF$_2$ | 6-Cl | Me |
| 5-Me, 7-F | OMe | 7-OCHF$_2$ | SCHF$_2$ | 7-Cl | Me |
| 5-Me, 7-Cl | OMe | 6,7-di-Me | SCHF$_2$ | 5-Br | Me |
| 5-Me, 7-CN | OMe | 5,7-di-Me | SCHF$_2$ | 6-Br | Me |
| 5-Me, 7-OMe | OMe | 5-Cl, 7-Me | SCHF$_2$ | 7-Br | Me |
| 5-OCHF$_2$ | Me | 5-CF$_3$ | F | 5-CF$_3$ | CN |
| 6-OCHF$_2$ | Me | 6-CF$_3$ | F | 6-CF$_3$ | CN |
| 7-OCHF$_2$ | Me | 7-CF$_3$ | F | 7-CF$_3$ | CN |
| 6,7-di-Me | Me | 5-F | F | 5-F | CN |
| 5,7-di-Me | Me | 6-F | F | 6-F | CN |
| 5-Cl, 7-Me | Me | 7-F | F | 7-F | CN |
| 5-Cl, 7-OMe | Me | 5-Cl | F | 5-Cl | CN |
| 5-F, 7-Me | Me | 6-Cl | F | 6-Cl | CN |
| 5-Me, 7-F | Me | 7-Cl | F | 7-Cl | CN |
| 5-Me, 7-Cl | Me | 5-Br | F | 5-Br | CN |
| 5-Me, 7-CN | Me | 6-Br | F | 6-Br | CN |
| 5-Me, 7-OMe | Me | 7-Br | F | 7-Br | CN |
| 5-Cl, 7-Me | Me | 5-OCHF$_2$ | F | 5-OCHF$_2$ | CN |
| 5-Cl, 7-OMe | Me | 6-OCHF$_2$ | F | 6-OCHF$_2$ | CN |
| 5-F, 7-Me | Me | 7-OCHF$_2$ | F | 7-OCHF$_2$ | CN |
| 5-Me, 7-F | Me | 6,7-di-Me | F | 6,7-di-Me | CN |
| 5-Me, 7-Cl | Me | 5,7-di-Me | F | 5,7-di-Me | CN |
| 5-Me, 7-CN | Me | 5-Cl, 7-Me | F | 5-Cl, 7-Me | CN |
| 5-Me, 7-OMe | Me | 5-Cl, 7-OMe | F | 5-Cl, 7-OMe | CN |
| 5,7-di-Cl | Me | 5-F, 7-Me | F | 5-F, 7-Me | CN |
| 5,7-di-Br | Me | 5-Me, 7-F | F | 5-Me, 7-F | CN |
| — | F | 5-Me, 7-Cl | F | 5-Me, 7-Cl | CN |
| 5-Me | F | 5-Me, 7-CN | F | 5-Me, 7-CN | CN |
| 6-Me | F | 5-Me, 7-OMe | F | 5-Me, 7-OMe | CN |
| 7-Me | F | 5,7-di-F | F | 5,7-di-F | CN |
| 5-Et | F | 5,7-di-Cl | F | 5,7-di-Cl | CN |
| 6-Et | F | 5,7-di-Br | F | 5,7-di-Br | CN |
| 7-Et | F | — | CN | — | OCHF$_2$ |
| 5-Pr | F | 5-Me | CN | 5-Me | OCHF$_2$ |
| 6-Pr | F | 6-Me | CN | 6-Me | OCHF$_2$ |
| 7-Pr | F | 7-Me | CN | 7-Me | OCHF$_2$ |
| 5-OMe | F | 5-Et | CN | 5-Et | OCHF$_2$ |
| 6-OMe | F | 6-Et | CN | 6-Et | OCHF$_2$ |
| 7-OMe | F | 7-Et | CN | 7-Et | OCHF$_2$ |
| 5-CN | F | 5-Pr | CN | 5-Pr | OCHF$_2$ |
| 6-CN | F | 6-Pr | CN | 6-Pr | OCHF$_2$ |
| 7-CN | F | 7-Pr | CN | 7-Pr | OCHF$_2$ |
| 5-OMe | OCHF$_2$ | 5-Et | SCF$_3$ | 5,7-di-Cl | SCF$_3$ |
| 6-OMe | OCHF$_2$ | 6-Et | SCF$_3$ | 5,7-di-Br | SCF$_3$ |

TABLE 1-continued

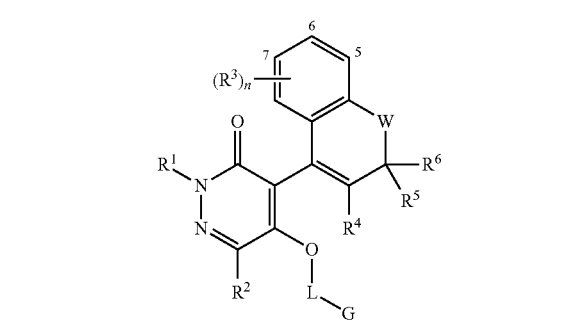

W is —CH$_2$—, R$^1$ is Me, R$^2$ is Me, R$^5$ is H, R$^6$ is H, L—G is H and

| (R$^3$)$_n$ | R$^4$ | (R$^3$)$_n$ | R$^4$ | (R$^3$)$_n$ | R$^4$ |
|---|---|---|---|---|---|
| 7-OMe | OCHF$_2$ | 7-Et | SCF$_3$ | — | Et |
| 5-CN | OCHF$_2$ | 5-Pr | SCF$_3$ | 5-Me | Et |
| 6-CN | OCHF$_2$ | 6-Pr | SCF$_3$ | 6-Me | Et |
| 7-CN | OCHF$_2$ | 7-Pr | SCF$_3$ | 7-Me | Et |
| 5-CF$_3$ | OCHF$_2$ | 5-OMe | SCF$_3$ | 5-Et | Et |
| 6-CF$_3$ | OCHF$_2$ | 6-OMe | SCF$_3$ | 6-Et | Et |
| 7-CF$_3$ | OCHF$_2$ | 7-OMe | SCF$_3$ | 7-Et | Et |
| 5-F | OCHF$_2$ | 5-CN | SCF$_3$ | 5-Pr | Et |
| 6-F | OCHF$_2$ | 6-CN | SCF$_3$ | 6-Pr | Et |
| 7-F | OCHF$_2$ | 7-CN | SCF$_3$ | 7-Pr | Et |
| 5-Cl | OCHF$_2$ | 5-CF$_3$ | SCF$_3$ | 5-OMe | Et |
| 6-Cl | OCHF$_2$ | 6-CF$_3$ | SCF$_3$ | 6-OMe | Et |
| 7-Cl | OCHF$_2$ | 7-CF$_3$ | SCF$_3$ | 7-OMe | Et |
| 5-Br | OCHF$_2$ | 5-F | SCF$_3$ | 5-CN | Et |
| 6-Br | OCHF$_2$ | 6-F | SCF$_3$ | 6-CN | Et |
| 7-Br | OCHF$_2$ | 7-F | SCF$_3$ | 7-CN | Et |
| 5-OCHF$_2$ | OCHF$_2$ | 5-Cl | SCF$_3$ | 5-CF$_3$ | Et |
| 6-OCHF$_2$ | OCHF$_2$ | 6-Cl | SCF$_3$ | 6-CF$_3$ | Et |
| 7-OCHF$_2$ | OCHF$_2$ | 7-Cl | SCF$_3$ | 7-CF$_3$ | Et |
| 6,7-di-Me | OCHF$_2$ | 5-Br | SCF$_3$ | 5-F | Et |
| 5,7-di-Me | OCHF$_2$ | 6-Br | SCF$_3$ | 6-F | Et |
| 5-Cl, 7-Me | OCHF$_2$ | 7-Br | SCF$_3$ | 7-F | Et |
| 5-Cl, 7-OMe | OCHF$_2$ | 5-OOCHF$_2$ | SCF$_3$ | 5-Cl | Et |
| 5-F, 7-Me | OCHF$_2$ | 6-OCHF$_2$ | SCF$_3$ | 6-Cl | Et |
| 5-Me, 7-F | OCHF$_2$ | 7-OCHF$_2$ | SCF$_3$ | 7-Cl | Et |
| 5-Me, 7-Cl | OCHF$_2$ | 6,7-di-Me | SCF$_3$ | 5-Br | Et |
| 5-Me, 7-CN | OCHF$_2$ | 5,7-di-Me | SCF$_3$ | 6-Br | Et |
| 5-Me, 7-OMe | OCHF$_2$ | 5-Cl, 7-Me | SCF$_3$ | 7-Br | Et |
| 5,7-di-F | OCHF$_2$ | 5-Cl, 7-OMe | SCF$_3$ | 5-OCHF$_2$ | Et |
| 5,7-di-Cl | OCHF$_2$ | 5-F, 7-Me | SCF$_3$ | 6-OCHF$_2$ | Et |
| 5,7-di-Br | OCHF$_2$ | 5-Me, 7-F | SCF$_3$ | 7-OCHF$_2$ | Et |
| — | SCF$_3$ | 5-Me, 7-Cl | SCF$_3$ | 6,7-di-Me | Et |
| 5-Me | SCF$_3$ | 5-Me, 7-CN | SCF$_3$ | 5,7-di-Me | Et |
| 6-Me | SCF$_3$ | 5-Me, 7-OMe | SCF$_3$ | 5-Cl, 7-Me | Et |
| 7-Me | SCF$_3$ | 5,7-di-F | SCF$_3$ | 5-Cl, 7-OMe | Et |
| 5-F, 7-Me | Et | 6-OCHF$_2$ | Cl | 6-Cl | C≡CH |
| 5-Me, 7-F | Et | 7-OCHF$_2$ | Cl | 7-Cl | C≡CH |
| 5-Me, 7-Cl | Et | 6,7-di-Me | Cl | 5-Br | C≡CH |
| 5-Me, 7-CN | Et | 5,7-di-Me | Cl | 6-Br | C≡CH |
| 5-Me, 7-OMe | Et | 5-Cl, 7-Me | Cl | 7-Br | C≡CH |
| 5,7-di-F | Et | 5-Cl, 7-OMe | Cl | 5-OCHF$_2$ | C≡CH |
| 5,7-di-Cl | Et | 5-F, 7-Me | Cl | 6-OCHF$_2$ | C≡CH |
| 5,7-di-Br | Et | 5-Me, 7-F | Cl | 7-OCHF$_2$ | C≡CH |
| — | Cl | 5-Me, 7-Cl | Cl | 6,7-di-Me | C≡CH |
| 5-Me | Cl | 5-Me, 7-CN | Cl | 5,7-di-Me | C≡CH |
| 6-Me | Cl | 5-Me, 7-OMe | Cl | 5-Cl, 7-Me | C≡CH |

TABLE 1-continued

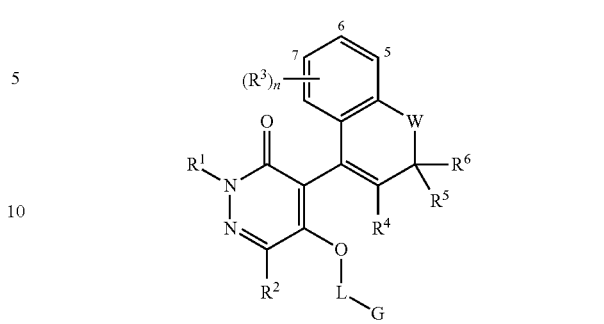

W is —CH$_2$—, R$^1$ is Me, R$^2$ is Me, R$^5$ is H, R$^6$ is H, L—G is H and

| (R$^3$)$_n$ | R$^4$ | (R$^3$)$_n$ | R$^4$ | (R$^3$)$_n$ | R$^4$ |
|---|---|---|---|---|---|
| 7-Me | Cl | 5,7-di-F | Cl | 5-Cl, 7-OMe | C≡CH |
| 5-Et | Cl | 5,7-di-Cl | Cl | 5-F, 7-Me | C≡CH |
| 6-Et | Cl | 5,7-di-Br | Cl | 5-Me, 7-F | C≡CH |
| 7-Et | Cl | — | C≡CH | 5-Me, 7-Cl | C≡CH |
| 5-Pr | Cl | 5-Me | C≡CH | 5-Me, 7-CN | C≡CH |
| 6-Pr | Cl | 6-Me | C≡CH | 5-Me, 7-OMe | C≡CH |
| 7-Pr | Cl | 7-Me | C≡CH | 5,7-di-F | C≡CH |
| 5-OMe | Cl | 5-Et | C≡CH | 5,7-di-Cl | C≡CH |
| 6-OMe | Cl | 6-Et | C≡CH | 5,7-di-Br | C≡CH |
| 7-OMe | Cl | 7-Et | C≡CH | — | SMe |
| 5-CN | Cl | 5-Pr | C≡CH | 5-Me | SMe |
| 6-CN | Cl | 6-Pr | C≡CH | 6-Me | SMe |
| 7-CN | Cl | 7-Pr | C≡CH | 7-Me | SMe |
| 5-CF$_3$ | Cl | 5-OMe | C≡CH | 5-Et | SMe |
| 6-CF$_3$ | Cl | 6-OMe | C≡CH | 6-Et | SMe |
| 7-CF$_3$ | Cl | 7-OMe | C≡CH | 7-Et | SMe |
| 5-F | Cl | 5-CN | C≡CH | 5-Pr | SMe |
| 6-F | Cl | 6-CN | C≡CH | 6-Pr | SMe |
| 7-F | Cl | 7-CN | C≡CH | 7-Pr | SMe |
| 5-Cl | Cl | 5-CF$_3$ | C≡CH | 5-OMe | SMe |
| 6-Cl | Cl | 6-CF$_3$ | C≡CH | 6-OMe | SMe |
| 7-Cl | Cl | 7-CF$_3$ | C≡CH | 7-OMe | SMe |
| 5-Br | Cl | 5-F | C≡CH | 5-CN | SMe |
| 6-Br | Cl | 6-F | C≡CH | 6-CN | SMe |
| 7-Br | Cl | 7-F | C≡CH | 7-CN | SMe |
| 5OCHF$_2$ | Cl | 5-Cl | C≡CH | 5-CF$_3$ | SMe |
| 6-CF$_3$ | SMe | 6-Br | SMe | 5-F, 7-Me | SMe |
| 7-CF$_3$ | SMe | 7-Br | SMe | 5-Me, 7-F | SMe |
| 5-F | SMe | 5-OCHF$_2$ | SMe | 5-Me, 7-Cl | SMe |
| 6-F | SMe | 6-OCHF$_2$ | SMe | 5-Me, 7-CN | SMe |
| 7-F | SMe | 7-OCHF$_2$ | SMe | 5-Me, 7-OMe | SMe |
| 5-Cl | SMe | 6,7-di-Me | SMe | 5,7-di-F | SMe |
| 6-Cl | SMe | 5,7-di-Me | SMe | 5,7-di-Cl | SMe |
| 7-Cl | SMe | 5-Cl, 7-Me | SMe | 5,7-di-Br | SMe |
| 5-Br | SMe | 5-Cl, 7-OMe | SMe | | |

Table 2 is constructed in the same manner as Table 1 except that the Row Heading "W is —CH$_2$—, R$^1$ is Me, R$^2$ is Me, R$^5$ is H, R$^6$ is H, L-G is H and" is replaced with the Row Heading listed for Table 2 below (i.e. "W is —CH$_2$—, R$^1$ is Me, R$^2$ is Me, R$^5$ is H, R$^6$ is H, and L-G is C(O)Et."). Therefore the first entry in Table 2 is a compound of Formula 1 wherein W is —CH$_2$—, R$^1$ is Me, R$^2$ is Me, (R$^3$)$_n$ is "-" (i.e. n is 0; no substitution with R$^3$), R$^5$ is H, R$^6$ is H, and L-G is C(O)Et. Tables 3 through 959 are constructed similarly.

| Table | Row Heading |
|---|---|
| 2 | W is —CH$_2$—, R$^1$ is Me, R$^2$ is Me, R$^5$ is H, R$^6$ is H, L—G is C(O)Et, and |
| 3 | W is —CH$_2$—, R$^1$ is Me, R$^2$ is Me, R$^5$ is H, R$^6$ is H, L—G is C(O)—i-Pr, and |
| 4 | W is —CH$_2$—, R$^1$ is Me, R$^2$ is Me, R$^5$ is H, R$^6$ is H, L—G is C(O)—t-Bu, and |
| 5 | W is —CH$_2$—, R$^1$ is Me, R$^2$ is Me, R$^5$ is H, R$^6$ is H, L—G is CO$_2$Me, and |
| 6 | W is —CH$_2$—, R$^1$ is Me, R$^2$ is Me, R$^5$ is H, R$^6$ is H, L—G is CO$_2$Et, and |
| 7 | W is —CH$_2$—, R$^1$ is Me, R$^2$ is Me, R$^5$ is H, R$^6$ is H, L—G is CO$_2$—i-Pr, and |
| 8 | W is —CH$_2$—, R$^1$ is Me, R$^2$ is Me, R$^5$ is H, R$^6$ is H, L—G is CO$_2$—t-Bu, and |
| 9 | W is —CH$_2$—, R$^1$ is Me, R$^2$ is Me, R$^5$ is H, R$^6$ is H, L—G is SO$_2$Me, and |

-continued

| Table Row Heading |
|---|
| 10  W is —CH$_2$—, R$^1$ is Me, R$^2$ is H, R$^5$ is H, R$^6$ is H, L—G is H, and |
| 11  W is —CH$_2$—, R$^1$ is Me, R$^2$ is H, R$^5$ is H, R$^6$ is H, L—G is C(O)Me, and |
| 12  W is —CH$_2$—, R$^1$ is Me, R$^2$ is H, R$^5$ is H, R$^6$ is H, L—G is C(O)Et, and |
| 13  W is —CH$_2$—, R$^1$ is Me, R$^2$ is H, R$^5$ is H, R$^6$ is H, L—G is C(O)—i-Pr, and |
| 14  W is —CH$_2$—, R$^1$ is Me, R$^2$ is H, R$^5$ is H, R$^6$ is H, L—G is C(O)—t-Bu, and |
| 15  W is —CH$_2$—, R$^1$ is Me, R$^2$ is H, R$^5$ is H, R$^6$ is H, L—G is CO$_2$Me, and |
| 16  W is —CH$_2$—, R$^1$ is Me, R$^2$ is H, R$^5$ is H, R$^6$ is H, L—G is CO$_2$Et, and |
| 17  W is —CH$_2$—, R$^1$ is Me, R$^2$ is H, R$^5$ is H, R$^6$ is H, L—G is CO$_2$—i-Pr, and |
| 18  W is —CH$_2$—, R$^1$ is Me, R$^2$ is H, R$^5$ is H, R$^6$ is H, L—G is CO$_2$—t-Bu, and |
| 19  W is —CH$_2$—, R$^1$ is Me, R$^2$ is H, R$^5$ is H, R$^6$ is H, L—G is SO$_2$Me, and |
| 20  W is —CH$_2$—, R$^1$ is Me, R$^2$ is CF$_3$, R$^5$ is H, R$^6$ is H, L—G is H, and |
| 21  W is —CH$_2$—, R$^1$ is Me, R$^2$ is CF$_3$, R$^5$ is H, R$^6$ is H, L—G is C(O)Me, and |
| 22  W is —CH$_2$—, R$^1$ is Me, R$^2$ is CF$_3$, R$^5$ is H, R$^6$ is H, L—G is C(O)Et, and |
| 23  W is —CH$_2$—, R$^1$ is Me, R$^2$ is CF$_3$, R$^5$ is H, R$^6$ is H, L—G is C(O)—i-Pr, and |
| 24  W is —CH$_2$—, R$^1$ is Me, R$^2$ is CF$_3$, R$^5$ is H, R$^6$ is H, L—G is C(O)—t-Bu, and |
| 25  W is —CH$_2$—, R$^1$ is Me, R$^2$ is CF$_3$, R$^5$ is H, R$^6$ is H, L—G is CO$_2$Me, and |
| 26  W is —CH$_2$—, R$^1$ is Me, R$^2$ is CF$_3$, R$^5$ is H, R$^6$ is H, L—G is CO$_2$Et, and |
| 27  W is —CH$_2$—, R$^1$ is Me, R$^2$ is CF$_3$, R$^5$ is H, R$^6$ is H, L—G is CO$_2$—i-Pr, and |
| 28  W is —CH$_2$—, R$^1$ is Me, R$^2$ is CF$_3$, R$^5$ is H, R$^6$ is H, L—G is CO$_2$—t-Bu, and |
| 29  W is —CH$_2$—, R$^1$ is Me, R$^2$ is CF$_3$, R$^5$ is H, R$^6$ is H, L—G is SO$_2$Me, and |
| 30  W is —CH$_2$—, R$^1$ is Me, R$^2$ is Cl, R$^5$ is H, R$^6$ is H, L—G is H, and |
| 31  W is —CH$_2$—, R$^1$ is Me, R$^2$ is Cl, R$^5$ is H, R$^6$ is H, L—G is C(O)Me, and |
| 32  W is —CH$_2$—, R$^1$ is Me, R$^2$ is Cl, R$^5$ is H, R$^6$ is H, L—G is C(O)Et, and |
| 33  W is —CH$_2$—, R$^1$ is Me, R$^2$ is Cl, R$^5$ is H, R$^6$ is H, L—G is C(O)—i-Pr, and |
| 34  W is —CH$_2$—, R$^1$ is Me, R$^2$ is Cl, R$^5$ is H, R$^6$ is H, L—G is C(O)—t-Bu, and |
| 35  W is —CH$_2$—, R$^1$ is Me, R$^2$ is Cl, R$^5$ is H, R$^6$ is H, L—G is CO$_2$Me, and |
| 36  W is —CH$_2$—, R$^1$ is Me, R$^2$ is Cl, R$^5$ is H, R$^6$ is H, L—G is CO$_2$Et, and |
| 37  W is —CH$_2$—, R$^1$ is Me, R$^2$ is Cl, R$^5$ is H, R$^6$ is H, L—G is CO$_2$—i-Pr, and |
| 38  W is —CH$_2$—, R$^1$ is Me, R$^2$ is Cl, R$^5$ is H, R$^6$ is H, L—G is CO$_2$—t-Bu, and |
| 39  W is —CH$_2$—, R$^1$ is Me, R$^2$ is Cl, R$^5$ is H, R$^6$ is H, L—G is SO$_2$Me, and |
| 40  W is —CH$_2$—, R$^1$ is Me, R$^2$ is Br, R$^5$ is H, R$^6$ is H, L—G is H, and |
| 41  W is —CH$_2$—, R$^1$ is Me, R$^2$ is Br, R$^5$ is H, R$^6$ is H, L—G is C(O)Me, and |
| 42  W is —CH$_2$—, R$^1$ is Me, R$^2$ is Br, R$^5$ is H, R$^6$ is H, L—G is C(O)Et, and |
| 43  W is —CH$_2$—, R$^1$ is Me, R$^2$ is Br, R$^5$ is H, R$^6$ is H, L—G is C(O)—i-Pr, and |
| 44  W is —CH$_2$—, R$^1$ is Me, R$^2$ is Br, R$^5$ is H, R$^6$ is H, L—G is C(O)—t-Bu, and |
| 45  W is —CH$_2$—, R$^1$ is Me, R$^2$ is Br, R$^5$ is H, R$^6$ is H, L—G is CO$_2$Me, and |
| 46  W is —CH$_2$—, R$^1$ is Me, R$^2$ is Br, R$^5$ is H, R$^6$ is H, L—G is CO$_2$Et, and |
| 47  W is —CH$_2$—, R$^1$ is Me, R$^2$ is Br, R$^5$ is H, R$^6$ is H, L—G is CO$_2$—i-Pr, and |
| 48  W is —CH$_2$—, R$^1$ is Me, R$^2$ is Br, R$^5$ is H, R$^6$ is H, L—G is CO$_2$—t-Bu, and |
| 49  W is —CH$_2$—, R$^1$ is Me, R$^2$ is Br, R$^5$ is H, R$^6$ is H, L—G is SO$_2$Me, and |
| 50  W is —CH$_2$—, R$^1$ is Me, R$^2$ is I, R$^5$ is H, R$^6$ is H, L—G is H, and |
| 51  W is —CH$_2$—, R$^1$ is Me, R$^2$ is I, R$^5$ is H, R$^6$ is H, L—G is C(O)Me, and |
| 52  W is —CH$_2$—, R$^1$ is Me, R$^2$ is I, R$^5$ is H, R$^6$ is H, L—G is C(O)Et, and |
| 53  W is —CH$_2$—, R$^1$ is Me, R$^2$ is I, R$^5$ is H, R$^6$ is H, L—G is C(O)—i-Pr, and |
| 54  W is —CH$_2$—, R$^1$ is Me, R$^2$ is I, R$^5$ is H, R$^6$ is H, L—G is C(O)—t-Bu, and |
| 55  W is —CH$_2$—, R$^1$ is Me, R$^2$ is I, R$^5$ is H, R$^6$ is H, L—G is CO$_2$Me, and |
| 56  W is —CH$_2$—, R$^1$ is Me, R$^2$ is I, R$^5$ is H, R$^6$ is H, L—G is CO$_2$Et, and |
| 57  W is —CH$_2$—, R$^1$ is Me, R$^2$ is I, R$^5$ is H, R$^6$ is H, L—G is CO$_2$—i-Pr, and |
| 58  W is —CH$_2$—, R$^1$ is Me, R$^2$ is I, R$^5$ is H, R$^6$ is H, L—G is CO$_2$—t-Bu, and |
| 59  W is —CH$_2$—, R$^1$ is Me, R$^2$ is I, R$^5$ is H, R$^6$ is H, L—G is SO$_2$Me, and |
| 60  W is —CH$_2$—, R$^1$ is Me, R$^2$ is OMe, R$^5$ is H, R$^6$ is H, L—G is H, and |
| 61  W is —CH$_2$—, R$^1$ is Me, R$^2$ is OMe, R$^5$ is H, R$^6$ is H, L—G is C(O)Me, and |
| 62  W is —CH$_2$—, R$^1$ is Me, R$^2$ is OMe, R$^5$ is H, R$^6$ is H, L—G is C(O)Et, and |
| 63  W is —CH$_2$—, R$^1$ is Me, R$^2$ is OMe, R$^5$ is H, R$^6$ is H, L—G is C(O)—i-Pr, and |
| 64  W is —CH$_2$—, R$^1$ is Me, R$^2$ is OMe, R$^5$ is H, R$^6$ is H, L—G is C(O)—t-Bu, and |
| 65  W is —CH$_2$—, R$^1$ is Me, R$^2$ is OMe, R$^5$ is H, R$^6$ is H, L—G is CO$_2$Me, and |
| 66  W is —CH$_2$—, R$^1$ is Me, R$^2$ is OMe, R$^5$ is H, R$^6$ is H, L—G is CO$_2$Et, and |
| 67  W is —CH$_2$—, R$^1$ is Me, R$^2$ is OMe, R$^5$ is H, R$^6$ is H, L—G is CO$_2$—i-Pr, and |
| 68  W is —CH$_2$—, R$^1$ is Me, R$^2$ is OMe, R$^5$ is H, R$^6$ is H, L—G is CO$_2$—t-Bu, and |
| 69  W is —CH$_2$—, R$^1$ is Me, R$^2$ is OMe, R$^5$ is H, R$^6$ is H, L—G is SO$_2$Me, and |
| 70  W is —CH$_2$—, R$^1$ is Me, R$^2$ is CN, R$^5$ is H, R$^6$ is H, L—G is H, and |
| 71  W is —CH$_2$—, R$^1$ is Me, R$^2$ is CN, R$^5$ is H, R$^6$ is H, L—G is C(O)Me, and |
| 72  W is —CH$_2$—, R$^1$ is Me, R$^2$ is CN, R$^5$ is H, R$^6$ is H, L—G is C(O)Et, and |
| 73  W is —CH$_2$—, R$^1$ is Me, R$^2$ is CN, R$^5$ is H, R$^6$ is H, L—G is C(O)—i-Pr, and |
| 74  W is —CH$_2$—, R$^1$ is Me, R$^2$ is CN, R$^5$ is H, R$^6$ is H, L—G is C(O)—t-Bu, and |
| 75  W is —CH$_2$—, R$^1$ is Me, R$^2$ is CN, R$^5$ is H, R$^6$ is H, L—G is CO$_2$Me, and |
| 76  W is —CH$_2$—, R$^1$ is Me, R$^2$ is CN, R$^5$ is H, R$^6$ is H, L—G is CO$_2$Et, and |
| 77  W is —CH$_2$—, R$^1$ is Me, R$^2$ is CN, R$^5$ is H, R$^6$ is H, L—G is CO$_2$—i-Pr, and |
| 78  W is —CH$_2$—, R$^1$ is Me, R$^2$ is CN, R$^5$ is H, R$^6$ is H, L—G is CO$_2$—t-Bu, and |
| 79  W is —CH$_2$—, R$^1$ is Me, R$^2$ is CN, R$^5$ is H, R$^6$ is H, L—G is SO$_2$Me, and |
| 80  W is —CH$_2$—, R$^1$ is Et, R$^2$ is Me, R$^5$ is H, R$^6$ is H, L—G is H, and |
| 81  W is —CH$_2$—, R$^1$ is Et, R$^2$ is Me, R$^5$ is H, R$^6$ is H, L—G is C(O)Me, and |
| 82  W is —CH$_2$—, R$^1$ is Et, R$^2$ is Me, R$^5$ is H, R$^6$ is H, L—G is C(O)Et, and |
| 83  W is —CH$_2$—, R$^1$ is Et, R$^2$ is Me, R$^5$ is H, R$^6$ is H, L—G is C(O)—i-Pr, and |
| 84  W is —CH$_2$—, R$^1$ is Et, R$^2$ is Me, R$^5$ is H, R$^6$ is H, L—G is C(O)—t-Bu, and |
| 85  W is —CH$_2$—, R$^1$ is Et, R$^2$ is Me, R$^5$ is H, R$^6$ is H, L—G is CO$_2$Me, and |
| 86  W is —CH$_2$—, R$^1$ is Et, R$^2$ is Me, R$^5$ is H, R$^6$ is H, L—G is CO$_2$Et, and |

-continued

| Table Row Heading | |
|---|---|
| 87 | W is —$CH_2$—, $R^1$ is Et, $R^2$ is Me, $R^5$ is H, $R^6$ is H, L—G is $CO_2$—i-Pr, and |
| 88 | W is —$CH_2$—, $R^1$ is Et, $R^2$ is Me, $R^5$ is H, $R^6$ is H, L—G is $CO_2$—t-Bu, and |
| 89 | W is —$CH_2$—, $R^1$ is Et, $R^2$ is Me, $R^5$ is H, $R^6$ is H, L—G is $SO_2$Me, and |
| 90 | W is —$CH_2$—, $R^1$ is Et, $R^2$ is H, $R^5$ is H, $R^6$ is H, L—G is H, and |
| 91 | W is —$CH_2$—, $R^1$ is Et, $R^2$ is H, $R^5$ is H, $R^6$ is H, L—G is C(O)Me, and |
| 92 | W is —$CH_2$—, $R^1$ is Et, $R^2$ is H, $R^5$ is H, $R^6$ is H, L—G is C(O)Et, and |
| 93 | W is —$CH_2$—, $R^1$ is Et, $R^2$ is H, $R^5$ is H, $R^6$ is H, L—G is C(O)—i-Pr, and |
| 94 | W is —$CH_2$—, $R^1$ is Et, $R^2$ is H, $R^5$ is H, $R^6$ is H, L—G is C(O)—t-Bu, and |
| 95 | W is —$CH_2$—, $R^1$ is Et, $R^2$ is H, $R^5$ is H, $R^6$ is H, L—G is $CO_2$Me, and |
| 96 | W is —$CH_2$—, $R^1$ is Et, $R^2$ is H, $R^5$ is H, $R^6$ is H, L—G is $CO_2$Et, and |
| 97 | W is —$CH_2$—, $R^1$ is Et, $R^2$ is H, $R^5$ is H, $R^6$ is H, L—G is $CO_2$—i-Pr, and |
| 98 | W is —$CH_2$—, $R^1$ is Et, $R^2$ is H, $R^5$ is H, $R^6$ is H, L—G is $CO_2$—t-Bu, and |
| 99 | W is —$CH_2$—, $R^1$ is Et, $R^2$ is H, $R^5$ is H, $R^6$ is H, L—G is $SO_2$Me, and |
| 100 | W is —$CH_2$—, $R^1$ is Et, $R^2$ is $CF_3$, $R^5$ is H, $R^6$ is H, L—G is H, and |
| 101 | W is —$CH_2$—, $R^1$ is Et, $R^2$ is $CF_3$, $R^5$ is H, $R^6$ is H, L—G is C(O)Me, and |
| 102 | W is —$CH_2$—, $R^1$ is Et, $R^2$ is $CF_3$, $R^5$ is H, $R^6$ is H, L—G is C(O)Et, and |
| 103 | W is —$CH_2$—, $R^1$ is Et, $R^2$ is $CF_3$, $R^5$ is H, $R^6$ is H, L—G is C(O)—i-Pr, and |
| 104 | W is —$CH_2$—, $R^1$ is Et, $R^2$ is $CF_3$, $R^5$ is H, $R^6$ is H, L—G is C(O)—t-Bu, and |
| 105 | W is —$CH_2$—, $R^1$ is Et, $R^2$ is $CF_3$, $R^5$ is H, $R^6$ is H, L—G is $CO_2$Me, and |
| 106 | W is —$CH_2$—, $R^1$ is Et, $R^2$ is $CF_3$, $R^5$ is H, $R^6$ is H, L—G is $CO_2$Et, and |
| 107 | W is —$CH_2$—, $R^1$ is Et, $R^2$ is $CF_3$, $R^5$ is H, $R^6$ is H, L—G is $CO_2$—i-Pr, and |
| 108 | W is —$CH_2$—, $R^1$ is Et, $R^2$ is $CF_3$, $R^5$ is H, $R^6$ is H, L—G is $CO_2$—t-Bu, and |
| 109 | W is —$CH_2$—, $R^1$ is Et, $R^2$ is $CF_3$, $R^5$ is H, $R^6$ is H, L—G is $SO_2$Me, and |
| 110 | W is —$CH_2$—, $R^1$ is Et, $R^2$ is Cl, $R^5$ is H, $R^6$ is H, L—G is H, and |
| 111 | W is —$CH_2$—, $R^1$ is Et, $R^2$ is Cl, $R^5$ is H, $R^6$ is H, L—G is C(O)Me, and |
| 112 | W is —$CH_2$—, $R^1$ is Et, $R^2$ is Cl, $R^5$ is H, $R^6$ is H, L—G is C(O)Et, and |
| 113 | W is —$CH_2$—, $R^1$ is Et, $R^2$ is Cl, $R^5$ is H, $R^6$ is H, L—G is C(O)—i-Pr, and |
| 114 | W is —$CH_2$—, $R^1$ is Et, $R^2$ is Cl, $R^5$ is H, $R^6$ is H, L—G is C(O)—t-Bu, and |
| 115 | W is —$CH_2$—, $R^1$ is Et, $R^2$ is Cl, $R^5$ is H, $R^6$ is H, L—G is $CO_2$Me, and |
| 116 | W is —$CH_2$—, $R^1$ is Et, $R^2$ is Cl, $R^5$ is H, $R^6$ is H, L—G is $CO_2$Et, and |
| 117 | W is —$CH_2$—, $R^1$ is Et, $R^2$ is Cl, $R^5$ is H, $R^6$ is H, L—G is $CO_2$—i-Pr, and |
| 118 | W is —$CH_2$—, $R^1$ is Et, $R^2$ is Cl, $R^5$ is H, $R^6$ is H, L—G is $CO_2$—t-Bu, and |
| 119 | W is —$CH_2$—, $R^1$ is Et, $R^2$ is Cl, $R^5$ is H, $R^6$ is H, L—G is $SO_2$Me, and |
| 120 | W is —$CH_2$—, $R^1$ is Et, $R^2$ is Br, $R^5$ is H, $R^6$ is H, L—G is H, and |
| 121 | W is —$CH_2$—, $R^1$ is Et, $R^2$ is Br, $R^5$ is H, $R^6$ is H, L—G is C(O)Me, and |
| 122 | W is —$CH_2$—, $R^1$ is Et, $R^2$ is Br, $R^5$ is H, $R^6$ is H, L—G is C(O)Et, and |
| 123 | W is —$CH_2$—, $R^1$ is Et, $R^2$ is Br, $R^5$ is H, $R^6$ is H, L—G is C(O)—i-Pr, and |
| 124 | W is —$CH_2$—, $R^1$ is Et, $R^2$ is Br, $R^5$ is H, $R^6$ is H, L—G is C(O)—t-Bu, and |
| 125 | W is —$CH_2$—, $R^1$ is Et, $R^2$ is Br, $R^5$ is H, $R^6$ is H, L—G is $CO_2$Me, and |
| 126 | W is —$CH_2$—, $R^1$ is Et, $R^2$ is Br, $R^5$ is H, $R^6$ is H, L—G is $CO_2$Et, and |
| 127 | W is —$CH_2$—, $R^1$ is Et, $R^2$ is Br, $R^5$ is H, $R^6$ is H, L—G is $CO_2$—i-Pr, and |
| 128 | W is —$CH_2$—, $R^1$ is Et, $R^2$ is Br, $R^5$ is H, $R^6$ is H, L—G is $CO_2$—t-Bu, and |
| 129 | W is —$CH_2$—, $R^1$ is Et, $R^2$ is Br, $R^5$ is H, $R^6$ is H, L—G is $SO_2$Me, and |
| 130 | W is —$CH_2$—, $R^1$ is Et, $R^2$ is I, $R^5$ is H, $R^6$ is H, L—G is H, and |
| 131 | W is —$CH_2$—, $R^1$ is Et, $R^2$ is I, $R^5$ is H, $R^6$ is H, L—G is C(O)Me, and |
| 132 | W is —$CH_2$—, $R^1$ is Et, $R^2$ is I, $R^5$ is H, $R^6$ is H, L—G is C(O)Et, and |
| 133 | W is —$CH_2$—, $R^1$ is Et, $R^2$ is I, $R^5$ is H, $R^6$ is H, L—G is C(O)—i-Pr, and |
| 134 | W is —$CH_2$—, $R^1$ is Et, $R^2$ is I, $R^5$ is H, $R^6$ is H, L—G is C(O)—t-Bu, and |
| 135 | W is —$CH_2$—, $R^1$ is Et, $R^2$ is I, $R^5$ is H, $R^6$ is H, L—G is $CO_2$Me, and |
| 136 | W is —$CH_2$—, $R^1$ is Et, $R^2$ is I, $R^5$ is H, $R^6$ is H, L—G is $CO_2$Et, and |
| 137 | W is —$CH_2$—, $R^1$ is Et, $R^2$ is I, $R^5$ is H, $R^6$ is H, L—G is $CO_2$—i-Pr, and |
| 138 | W is —$CH_2$—, $R^1$ is Et, $R^2$ is I, $R^5$ is H, $R^6$ is H, L—G is $CO_2$—t-Bu, and |
| 139 | W is —$CH_2$—, $R^1$ is Et, $R^2$ is I, $R^5$ is H, $R^6$ is H, L—G is $SO_2$Me, and |
| 140 | W is —$CH_2$—, $R^1$ is Et, $R^2$ is OMe, $R^5$ is H, $R^6$ is H, L—G is H, and |
| 141 | W is —$CH_2$—, $R^1$ is Et, $R^2$ is OMe, $R^5$ is H, $R^6$ is H, L—G is C(O)Me, and |
| 142 | W is —$CH_2$—, $R^1$ is Et, $R^2$ is OMe, $R^5$ is H, $R^6$ is H, L—G is C(O)Et, and |
| 143 | W is —$CH_2$—, $R^1$ is Et, $R^2$ is OMe, $R^5$ is H, $R^6$ is H, L—G is C(O)—i-Pr, and |
| 144 | W is —$CH_2$—, $R^1$ is Et, $R^2$ is OMe, $R^5$ is H, $R^6$ is H, L—G is C(O)—t-Bu, and |
| 145 | W is —$CH_2$—, $R^1$ is Et, $R^2$ is OMe, $R^5$ is H, $R^6$ is H, L—G is $CO_2$Me, and |
| 146 | W is —$CH_2$—, $R^1$ is Et, $R^2$ is OMe, $R^5$ is H, $R^6$ is H, L—G is $CO_2$Et, and |
| 147 | W is —$CH_2$—, $R^1$ is Et, $R^2$ is OMe, $R^5$ is H, $R^6$ is H, L—G is $CO_2$—i-Pr, and |
| 148 | W is —$CH_2$—, $R^1$ is Et, $R^2$ is OMe, $R^5$ is H, $R^6$ is H, L—G is $CO_2$—t-Bu, and |
| 149 | W is —$CH_2$—, $R^1$ is Et, $R^2$ is OMe, $R^5$ is H, $R^6$ is H, L—G is $SO_2$Me, and |
| 150 | W is —$CH_2$—, $R^1$ is Et, $R^2$ is CN, $R^5$ is H, $R^6$ is H, L—G is H, and |
| 151 | W is —$CH_2$—, $R^1$ is Et, $R^2$ is CN, $R^5$ is H, $R^6$ is H, L—G is C(O)Me, and |
| 152 | W is —$CH_2$—, $R^1$ is Et, $R^2$ is CN, $R^5$ is H, $R^6$ is H, L—G is C(O)Et, and |
| 153 | W is —$CH_2$—, $R^1$ is Et, $R^2$ is CN, $R^5$ is H, $R^6$ is H, L—G is C(O)—i-Pr, and |
| 154 | W is —$CH_2$—, $R^1$ is Et, $R^2$ is CN, $R^5$ is H, $R^6$ is H, L—G is C(O)—t-Bu, and |
| 155 | W is —$CH_2$—, $R^1$ is Et, $R^2$ is CN, $R^5$ is H, $R^6$ is H, L—G is $CO_2$Me, and |
| 156 | W is —$CH_2$—, $R^1$ is Et, $R^2$ is CN, $R^5$ is H, $R^6$ is H, L—G is $CO_2$Et, and |
| 157 | W is —$CH_2$—, $R^1$ is Et, $R^2$ is CN, $R^5$ is H, $R^6$ is H, L—G is $CO_2$—i-Pr, and |
| 158 | W is —$CH_2$—, $R^1$ is Et, $R^2$ is CN, $R^5$ is H, $R^6$ is H, L—G is $CO_2$—t-Bu, and |
| 159 | W is —$CH_2$—, $R^1$ is Et, $R^2$ is CN, $R^5$ is H, $R^6$ is H, L—G is $SO_2$Me, and |
| 160 | W is —$C(CH_3)_2$—, $R^1$ is Me, $R^2$ is Me, $R^5$ is H, $R^6$ is H, L—G is H, and |
| 161 | W is —$C(CH_3)_2$—, $R^1$ is Me, $R^2$ is Me, $R^5$ is H, $R^6$ is H, L—G is C(O)Me, and |
| 162 | W is —$C(CH_3)_2$—, $R^1$ is Me, $R^2$ is Me, $R^5$ is H, $R^6$ is H, L—G is C(O)Et, and |
| 163 | W is —$C(CH_3)_2$—, $R^1$ is Me, $R^2$ is Me, $R^5$ is H, $R^6$ is H, L—G is C(O)—i-Pr, and |

-continued

| Table Row Heading |
|---|
| 164 W is —C(CH$_3$)$_2$—, R$^1$ is Me, R$^2$ is Me, R$^5$ is H, R$^6$ is H, L—G is C(O)—t-Bu, and |
| 165 W is —C(CH$_3$)$_2$—, R$^1$ is Me, R$^2$ is Me, R$^5$ is H, R$^6$ is H, L—G is CO$_2$Me, and |
| 166 W is —C(CH$_3$)$_2$—, R$^1$ is Me, R$^2$ is Me, R$^5$ is H, R$^6$ is H, L—G is CO$_2$Et, and |
| 167 W is —C(CH$_3$)$_2$—, R$^1$ is Me, R$^2$ is Me, R$^5$ is H, R$^6$ is H, L—G is CO$_2$—i-Pr, and |
| 168 W is —C(CH$_3$)$_2$—, R$^1$ is Me, R$^2$ is Me, R$^5$ is H, R$^6$ is H, L—G is CO$_2$—t-Bu, and |
| 169 W is —C(CH$_3$)$_2$—, R$^1$ is Me, R$^2$ is Me, R$^5$ is H, R$^6$ is H, L—G is SO$_2$Me, and |
| 170 W is —C(CH$_3$)$_2$—, R$^1$ is Me, R$^2$ is H, R$^5$ is H, R$^6$ is H, L—G is H, and |
| 171 W is —C(CH$_3$)$_2$—, R$^1$ is Me, R$^2$ is H, R$^5$ is H, R$^6$ is H, L—G is C(O)Me, and |
| 172 W is —C(CH$_3$)$_2$—, R$^1$ is Me, R$^2$ is H, R$^5$ is H, R$^6$ is H, L—G is C(O)Et, and |
| 173 W is —C(CH$_3$)$_2$—, R$^1$ is Me, R$^2$ is H, R$^5$ is H, R$^6$ is H, L—G is C(O)—i-Pr, and |
| 174 W is —C(CH$_3$)$_2$—, R$^1$ is Me, R$^2$ is H, R$^5$ is H, R$^6$ is H, L—G is C(O)—t-Bu, and |
| 175 W is —C(CH$_3$)$_2$—, R$^1$ is Me, R$^2$ is H, R$^5$ is H, R$^6$ is H, L—G is CO$_2$Me, and |
| 176 W is —C(CH$_3$)$_2$—, R$^1$ is Me, R$^2$ is H, R$^5$ is H, R$^6$ is H, L—G is CO$_2$Et, and |
| 177 W is —C(CH$_3$)$_2$—, R$^1$ is Me, R$^2$ is H, R$^5$ is H, R$^6$ is H, L—G is CO$_2$—i-Pr, and |
| 178 W is —C(CH$_3$)$_2$—, R$^1$ is Me, R$^2$ is H, R$^5$ is H, R$^6$ is H, L—G is CO$_2$—t-Bu, and |
| 179 W is —C(CH$_3$)$_2$—, R$^1$ is Me, R$^2$ is H, R$^5$ is H, R$^6$ is H, L—G is SO$_2$Me, and |
| 180 W is —C(CH$_3$)$_2$—, R$^1$ is Me, R$^2$ is CF$_3$, R$^5$ is H, R$^6$ is H, L—G is H, and |
| 181 W is —C(CH$_3$)$_2$—, R$^1$ is Me, R$^2$ is CF$_3$, R$^5$ is H, R$^6$ is H, L—G is C(O)Me, and |
| 182 W is —C(CH$_3$)$_2$—, R$^1$ is Me, R$^2$ is CF$_3$, R$^5$ is H, R$^6$ is H, L—G is C(O)Et, and |
| 183 W is —C(CH$_3$)$_2$—, R$^1$ is Me, R$^2$ is CF$_3$, R$^5$ is H, R$^6$ is H, L—G is C(O)—i-Pr, and |
| 184 W is —C(CH$_3$)$_2$—, R$^1$ is Me, R$^2$ is CF$_3$, R$^5$ is H, R$^6$ is H, L—G is C(O)—t-Bu, and |
| 185 W is —C(CH$_3$)$_2$—, R$^1$ is Me, R$^2$ is CF$_3$, R$^5$ is H, R$^6$ is H, L—G is CO$_2$Me, and |
| 186 W is —C(CH$_3$)$_2$—, R$^1$ is Me, R$^2$ is CF$_3$, R$^5$ is H, R$^6$ is H, L—G is CO$_2$Et, and |
| 187 W is —C(CH$_3$)$_2$—, R$^1$ is Me, R$^2$ is CF$_3$, R$^5$ is H, R$^6$ is H, L—G is CO$_2$—i-Pr, and |
| 188 W is —C(CH$_3$)$_2$—, R$^1$ is Me, R$^2$ is CF$_3$, R$^5$ is H, R$^6$ is H, L—G is CO$_2$—t-Bu, and |
| 189 W is —C(CH$_3$)$_2$—, R$^1$ is Me, R$^2$ is CF$_3$, R$^5$ is H, R$^6$ is H, L—G is SO$_2$Me, and |
| 190 W is —C(CH$_3$)$_2$—, R$^1$ is Me, R$^2$ is Cl, R$^5$ is H, R$^6$ is H, L—G is H, and |
| 191 W is —C(CH$_3$)$_2$—, R$^1$ is Me, R$^2$ is Cl, R$^5$ is H, R$^6$ is H, L—G is C(O)Me, and |
| 192 W is —C(CH$_3$)$_2$—, R$^1$ is Me, R$^2$ is Cl, R$^5$ is H, R$^6$ is H, L—G is C(O)Et, and |
| 193 W is —C(CH$_3$)$_2$—, R$^1$ is Me, R$^2$ is Cl, R$^5$ is H, R$^6$ is H, L—G is C(O)—i-Pr, and |
| 194 W is —C(CH$_3$)$_2$—, R$^1$ is Me, R$^2$ is Cl, R$^5$ is H, R$^6$ is H, L—G is C(O)—t-Bu, and |
| 195 W is —C(CH$_3$)$_2$—, R$^1$ is Me, R$^2$ is Cl, R$^5$ is H, R$^6$ is H, L—G is CO$_2$Me, and |
| 196 W is —C(CH$_3$)$_2$—, R$^1$ is Me, R$^2$ is Cl, R$^5$ is H, R$^6$ is H, L—G is CO$_2$Et, and |
| 197 W is —C(CH$_3$)$_2$—, R$^1$ is Me, R$^2$ is Cl, R$^5$ is H, R$^6$ is H, L—G is CO$_2$—i-Pr, and |
| 198 W is —C(CH$_3$)$_2$—, R$^1$ is Me, R$^2$ is Cl, R$^5$ is H, R$^6$ is H, L—G is CO$_2$—t-Bu, and |
| 199 W is —C(CH$_3$)$_2$—, R$^1$ is Me, R$^2$ is Cl, R$^5$ is H, R$^6$ is H, L—G is SO$_2$Me, and |
| 200 W is —C(CH$_3$)$_2$—, R$^1$ is Me, R$^2$ is Br, R$^5$ is H, R$^6$ is H, L—G is H, and |
| 201 W is —C(CH$_3$)$_2$—, R$^1$ is Me, R$^2$ is Br, R$^5$ is H, R$^6$ is H, L—G is C(O)Me, and |
| 202 W is —C(CH$_3$)$_2$—, R$^1$ is Me, R$^2$ is Br, R$^5$ is H, R$^6$ is H, L—G is C(O)Et, and |
| 203 W is —C(CH$_3$)$_2$—, R$^1$ is Me, R$^2$ is Br, R$^5$ is H, R$^6$ is H, L—G is C(O)—i-Pr, and |
| 204 W is —C(CH$_3$)$_2$—, R$^1$ is Me, R$^2$ is Br, R$^5$ is H, R$^6$ is H, L—G is C(O)—t-Bu, and |
| 205 W is —C(CH$_3$)$_2$—, R$^1$ is Me, R$^2$ is Br, R$^5$ is H, R$^6$ is H, L—G is CO$_2$Me, and |
| 206 W is —C(CH$_3$)$_2$—, R$^1$ is Me, R$^2$ is Br, R$^5$ is H, R$^6$ is H, L—G is CO$_2$Et, and |
| 207 W is —C(CH$_3$)$_2$—, R$^1$ is Me, R$^2$ is Br, R$^5$ is H, R$^6$ is H, L—G is CO$_2$—i-Pr, and |
| 208 W is —C(CH$_3$)$_2$—, R$^1$ is Me, R$^2$ is Br, R$^5$ is H, R$^6$ is H, L—G is CO$_2$—t-Bu, and |
| 209 W is —C(CH$_3$)$_2$—, R$^1$ is Me, R$^2$ is Br, R$^5$ is H, R$^6$ is H, L—G is SO$_2$Me, and |
| 210 W is —C(CH$_3$)$_2$—, R$^1$ is Me, R$^2$ is I, R$^5$ is H, R$^6$ is H, L—G is H, and |
| 211 W is —C(CH$_3$)$_2$—, R$^1$ is Me, R$^2$ is I, R$^5$ is H, R$^6$ is H, L—G is C(O)Me, and |
| 212 W is —C(CH$_3$)$_2$—, R$^1$ is Me, R$^2$ is I, R$^5$ is H, R$^6$ is H, L—G is C(O)Et, and |
| 213 W is —C(CH$_3$)$_2$—, R$^1$ is Me, R$^2$ is I, R$^5$ is H, R$^6$ is H, L—G is C(O)—i-Pr, and |
| 214 W is —C(CH$_3$)$_2$—, R$^1$ is Me, R$^2$ is I, R$^5$ is H, R$^6$ is H, L—G is C(O)—t-Bu, and |
| 215 W is —C(CH$_3$)$_2$—, R$^1$ is Me, R$^2$ is I, R$^5$ is H, R$^6$ is H, L—G is CO$_2$Me, and |
| 216 W is —C(CH$_3$)$_2$—, R$^1$ is Me, R$^2$ is I, R$^5$ is H, R$^6$ is H, L—G is CO$_2$Et, and |
| 217 W is —C(CH$_3$)$_2$—, R$^1$ is Me, R$^2$ is I, R$^5$ is H, R$^6$ is H, L—G is CO$_2$—i-Pr, and |
| 218 W is —C(CH$_3$)$_2$—, R$^1$ is Me, R$^2$ is I, R$^5$ is H, R$^6$ is H, L—G is CO$_2$—t-Bu, and |
| 219 W is —C(CH$_3$)$_2$—, R$^1$ is Me, R$^2$ is I, R$^5$ is H, R$^6$ is H, L—G is SO$_2$Me, and |
| 220 W is —C(CH$_3$)$_2$—, R$^1$ is Me, R$^2$ is OMe, R$^5$ is H, R$^6$ is H, L—G is H, and |
| 221 W is —C(CH$_3$)$_2$—, R$^1$ is Me, R$^2$ is OMe, R$^5$ is H, R$^6$ is H, L—G is C(O)Me, and |
| 222 W is —C(CH$_3$)$_2$—, R$^1$ is Me, R$^2$ is OMe, R$^5$ is H, R$^6$ is H, L—G is C(O)Et, and |
| 223 W is —C(CH$_3$)$_2$—, R$^1$ is Me, R$^2$ is OMe, R$^5$ is H, R$^6$ is H, L—G is C(O)—i-Pr, and |
| 224 W is —C(CH$_3$)$_2$—, R$^1$ is Me, R$^2$ is OMe, R$^5$ is H, R$^6$ is H, L—G is C(O)—t-Bu, and |
| 225 W is —C(CH$_3$)$_2$—, R$^1$ is Me, R$^2$ is OMe, R$^5$ is H, R$^6$ is H, L—G is CO$_2$Me, and |
| 226 W is —C(CH$_3$)$_2$—, R$^1$ is Me, R$^2$ is OMe, R$^5$ is H, R$^6$ is H, L—G is CO$_2$Et, and |
| 227 W is —C(CH$_3$)$_2$—, R$^1$ is Me, R$^2$ is OMe, R$^5$ is H, R$^6$ is H, L—G is CO$_2$—i-Pr, and |
| 228 W is —C(CH$_3$)$_2$—, R$^1$ is Me, R$^2$ is OMe, R$^5$ is H, R$^6$ is H, L—G is CO$_2$—t-Bu, and |
| 229 W is —C(CH$_3$)$_2$—, R$^1$ is Me, R$^2$ is OMe, R$^5$ is H, R$^6$ is H, L—G is SO$_2$Me, and |
| 230 W is —C(CH$_3$)$_2$—, R$^1$ is Me, R$^2$ is CN, R$^5$ is H, R$^6$ is H, L—G is H, and |
| 231 W is —C(CH$_3$)$_2$—, R$^1$ is Me, R$^2$ is CN, R$^5$ is H, R$^6$ is H, L—G is C(O)Me, and |
| 232 W is —C(CH$_3$)$_2$—, R$^1$ is Me, R$^2$ is CN, R$^5$ is H, R$^6$ is H, L—G is C(O)Et, and |
| 233 W is —C(CH$_3$)$_2$—, R$^1$ is Me, R$^2$ is CN, R$^5$ is H, R$^6$ is H, L—G is C(O)—i-Pr, and |
| 234 W is —C(CH$_3$)$_2$—, R$^1$ is Me, R$^2$ is CN, R$^5$ is H, R$^6$ is H, L—G is C(O)—t-Bu, and |
| 235 W is —C(CH$_3$)$_2$—, R$^1$ is Me, R$^2$ is CN, R$^5$ is H, R$^6$ is H, L—G is CO$_2$Me, and |
| 236 W is —C(CH$_3$)$_2$—, R$^1$ is Me, R$^2$ is CN, R$^5$ is H, R$^6$ is H, L—G is CO$_2$Et, and |
| 237 W is —C(CH$_3$)$_2$—, R$^1$ is Me, R$^2$ is CN, R$^5$ is H, R$^6$ is H, L—G is CO$_2$—i-Pr, and |
| 238 W is —C(CH$_3$)$_2$—, R$^1$ is Me, R$^2$ is CN, R$^5$ is H, R$^6$ is H, L—G is CO$_2$—t-Bu, and |
| 239 W is —C(CH$_3$)$_2$—, R$^1$ is Me, R$^2$ is CN, R$^5$ is H, R$^6$ is H, L—G is SO$_2$Me, and |
| 240 W is —C(CH$_3$)$_2$—, R$^1$ is Et, R$^2$ is Me, R$^5$ is H, R$^6$ is H, L—G is H, and |

| Table Row Heading |
| --- |
| 241 W is —C(CH$_3$)$_2$—, R$^1$ is Et, R$^2$ is Me, R$^5$ is H, R$^6$ is H, L—G is C(O)Me, and |
| 242 W is —C(CH$_3$)$_2$—, R$^1$ is Et, R$^2$ is Me, R$^5$ is H, R$^6$ is H, L—G is C(O)Et, and |
| 243 W is —C(CH$_3$)$_2$—, R$^1$ is Et, R$^2$ is Me, R$^5$ is H, R$^6$ is H, L—G is C(O)—i-Pr, and |
| 244 W is —C(CH$_3$)$_2$—, R$^1$ is Et, R$^2$ is Me, R$^5$ is H, R$^6$ is H, L—G is C(O)—t-Bu, and |
| 245 W is —C(CH$_3$)$_2$—, R$^1$ is Et, R$^2$ is Me, R$^5$ is H, R$^6$ is H, L—G is CO$_2$Me, and |
| 246 W is —C(CH$_3$)$_2$—, R$^1$ is Et, R$^2$ is Me, R$^5$ is H, R$^6$ is H, L—G is CO$_2$Et, and |
| 247 W is —C(CH$_3$)$_2$—, R$^1$ is Et, R$^2$ is Me, R$^5$ is H, R$^6$ is H, L—G is CO$_2$—i-Pr, and |
| 248 W is —C(CH$_3$)$_2$—, R$^1$ is Et, R$^2$ is Me, R$^5$ is H, R$^6$ is H, L—G is CO$_2$—t-Bu, and |
| 249 W is —C(CH$_3$)$_2$—, R$^1$ is Et, R$^2$ is Me, R$^5$ is H, R$^6$ is H, L—G is SO$_2$Me, and |
| 250 W is —C(CH$_3$)$_2$—, R$^1$ is Et, R$^2$ is H, R$^5$ is H, R$^6$ is H, L—G is H, and |
| 251 W is —C(CH$_3$)$_2$—, R$^1$ is Et, R$^2$ is H, R$^5$ is H, R$^6$ is H, L—G is C(O)Me, and |
| 252 W is —C(CH$_3$)$_2$—, R$^1$ is Et, R$^2$ is H, R$^5$ is H, R$^6$ is H, L—G is C(O)Et, and |
| 253 W is —C(CH$_3$)$_2$—, R$^1$ is Et, R$^2$ is H, R$^5$ is H, R$^6$ is H, L—G is C(O)—i-Pr, and |
| 254 W is —C(CH$_3$)$_2$—, R$^1$ is Et, R$^2$ is H, R$^5$ is H, R$^6$ is H, L—G is C(O)—t-Bu, and |
| 255 W is —C(CH$_3$)$_2$—, R$^1$ is Et, R$^2$ is H, R$^5$ is H, R$^6$ is H, L—G is CO$_2$Me, and |
| 256 W is —C(CH$_3$)$_2$—, R$^1$ is Et, R$^2$ is H, R$^5$ is H, R$^6$ is H, L—G is CO$_2$Et, and |
| 257 W is —C(CH$_3$)$_2$—, R$^1$ is Et, R$^2$ is H, R$^5$ is H, R$^6$ is H, L—G is CO$_2$—i-Pr, and |
| 258 W is —C(CH$_3$)$_2$—, R$^1$ is Et, R$^2$ is H, R$^5$ is H, R$^6$ is H, L—G is CO$_2$—t-Bu, and |
| 259 W is —C(CH$_3$)$_2$—, R$^1$ is Et, R$^2$ is H, R$^5$ is H, R$^6$ is H, L—G is SO$_2$Me, and |
| 260 W is —C(CH$_3$)$_2$—, R$^1$ is Et, R$^2$ is CF$_3$, R$^5$ is H, R$^6$ is H, L—G is H, and |
| 261 W is —C(CH$_3$)$_2$—, R$^1$ is Et, R$^2$ is CF$_3$, R$^5$ is H, R$^6$ is H, L—G is C(O)Me, and |
| 262 W is —C(CH$_3$)$_2$—, R$^1$ is Et, R$^2$ is CF$_3$, R$^5$ is H, R$^6$ is H, L—G is C(O)Et, and |
| 263 W is —C(CH$_3$)$_2$—, R$^1$ is Et, R$^2$ is CF$_3$, R$^5$ is H, R$^6$ is H, L—G is C(O)—i-Pr, and |
| 264 W is —C(CH$_3$)$_2$—, R$^1$ is Et, R$^2$ is CF$_3$, R$^5$ is H, R$^6$ is H, L—G is C(O)—t-Bu, and |
| 265 W is —C(CH$_3$)$_2$—, R$^1$ is Et, R$^2$ is CF$_3$, R$^5$ is H, R$^6$ is H, L—G is CO$_2$Me, and |
| 266 W is —C(CH$_3$)$_2$—, R$^1$ is Et, R$^2$ is CF$_3$, R$^5$ is H, R$^6$ is H, L—G is CO$_2$Et, and |
| 267 W is —C(CH$_3$)$_2$—, R$^1$ is Et, R$^2$ is CF$_3$, R$^5$ is H, R$^6$ is H, L—G is CO$_2$—i-Pr, and |
| 268 W is —C(CH$_3$)$_2$—, R$^1$ is Et, R$^2$ is CF$_3$, R$^5$ is H, R$^6$ is H, L—G is CO$_2$—t-Bu, and |
| 269 W is —C(CH$_3$)$_2$—, R$^1$ is Et, R$^2$ is CF$_3$, R$^5$ is H, R$^6$ is H, L—G is SO$_2$Me, and |
| 270 W is —C(CH$_3$)$_2$—, R$^1$ is Et, R$^2$ is Cl, R$^5$ is H, R$^6$ is H, L—G is H, and |
| 271 W is —C(CH$_3$)$_2$—, R$^1$ is Et, R$^2$ is Cl, R$^5$ is H, R$^6$ is H, L—G is C(O)Me, and |
| 272 W is —C(CH$_3$)$_2$—, R$^1$ is Et, R$^2$ is Cl, R$^5$ is H, R$^6$ is H, L—G is C(O)Et, and |
| 273 W is —C(CH$_3$)$_2$—, R$^1$ is Et, R$^2$ is Cl, R$^5$ is H, R$^6$ is H, L—G is C(O)—i-Pr, and |
| 274 W is —C(CH$_3$)$_2$—, R$^1$ is Et, R$^2$ is Cl, R$^5$ is H, R$^6$ is H, L—G is C(O)—t-Bu, and |
| 275 W is —C(CH$_3$)$_2$—, R$^1$ is Et, R$^2$ is Cl, R$^5$ is H, R$^6$ is H, L—G is CO$_2$Me, and |
| 276 W is —C(CH$_3$)$_2$—, R$^1$ is Et, R$^2$ is Cl, R$^5$ is H, R$^6$ is H, L—G is CO$_2$Et, and |
| 277 W is —C(CH$_3$)$_2$—, R$^1$ is Et, R$^2$ is Cl, R$^5$ is H, R$^6$ is H, L—G is CO$_2$—i-Pr, and |
| 278 W is —C(CH$_3$)$_2$—, R$^1$ is Et, R$^2$ is Cl, R$^5$ is H, R$^6$ is H, L—G is CO$_2$—t-Bu, and |
| 279 W is —C(CH$_3$)$_2$—, R$^1$ is Et, R$^2$ is Cl, R$^5$ is H, R$^6$ is H, L—G is SO$_2$Me, and |
| 280 W is —C(CH$_3$)$_2$—, R$^1$ is Et, R$^2$ is Br, R$^5$ is H, R$^6$ is H, L—G is H, and |
| 281 W is —C(CH$_3$)$_2$—, R$^1$ is Et, R$^2$ is Br, R$^5$ is H, R$^6$ is H, L—G is C(O)Me, and |
| 282 W is —C(CH$_3$)$_2$—, R$^1$ is Et, R$^2$ is Br, R$^5$ is H, R$^6$ is H, L—G is C(O)Et, and |
| 283 W is —C(CH$_3$)$_2$—, R$^1$ is Et, R$^2$ is Br, R$^5$ is H, R$^6$ is H, L—G is C(O)—i-Pr, and |
| 284 W is —C(CH$_3$)$_2$—, R$^1$ is Et, R$^2$ is Br, R$^5$ is H, R$^6$ is H, L—G is C(O)—t-Bu, and |
| 285 W is —C(CH$_3$)$_2$—, R$^1$ is Et, R$^2$ is Br, R$^5$ is H, R$^6$ is H, L—G is CO$_2$Me, and |
| 286 W is —C(CH$_3$)$_2$—, R$^1$ is Et, R$^2$ is Br, R$^5$ is H, R$^6$ is H, L—G is CO$_2$Et, and |
| 287 W is —C(CH$_3$)$_2$—, R$^1$ is Et, R$^2$ is Br, R$^5$ is H, R$^6$ is H, L—G is CO$_2$—i-Pr, and |
| 288 W is —C(CH$_3$)$_2$—, R$^1$ is Et, R$^2$ is Br, R$^5$ is H, R$^6$ is H, L—G is CO$_2$—t-Bu, and |
| 289 W is —C(CH$_3$)$_2$—, R$^1$ is Et, R$^2$ is Br, R$^5$ is H, R$^6$ is H, L—G is SO$_2$Me, and |
| 290 W is —C(CH$_3$)$_2$—, R$^1$ is Et, R$^2$ is I, R$^5$ is H, R$^6$ is H, L—G is H, and |
| 291 W is —C(CH$_3$)$_2$—, R$^1$ is Et, R$^2$ is I, R$^5$ is H, R$^6$ is H, L—G is C(O)Me, and |
| 292 W is —C(CH$_3$)$_2$—, R$^1$ is Et, R$^2$ is I, R$^5$ is H, R$^6$ is H, L—G is C(O)Et, and |
| 293 W is —C(CH$_3$)$_2$—, R$^1$ is Et, R$^2$ is I, R$^5$ is H, R$^6$ is H, L—G is C(O)—i-Pr, and |
| 294 W is —C(CH$_3$)$_2$—, R$^1$ is Et, R$^2$ is I, R$^5$ is H, R$^6$ is H, L—G is C(O)—t-Bu, and |
| 295 W is —C(CH$_3$)$_2$—, R$^1$ is Et, R$^2$ is I, R$^5$ is H, R$^6$ is H, L—G is CO$_2$Me, and |
| 296 W is —C(CH$_3$)$_2$—, R$^1$ is Et, R$^2$ is I, R$^5$ is H, R$^6$ is H, L—G is CO$_2$Et, and |
| 297 W is —C(CH$_3$)$_2$—, R$^1$ is Et, R$^2$ is I, R$^5$ is H, R$^6$ is H, L—G is CO$_2$—i-Pr, and |
| 298 W is —C(CH$_3$)$_2$—, R$^1$ is Et, R$^2$ is I, R$^5$ is H, R$^6$ is H, L—G is CO$_2$—t-Bu, and |
| 299 W is —C(CH$_3$)$_2$—, R$^1$ is Et, R$^2$ is I, R$^5$ is H, R$^6$ is H, L—G is SO$_2$Me, and |
| 300 W is —C(CH$_3$)$_2$—, R$^1$ is Et, R$^2$ is OMe, R$^5$ is H, R$^6$ is H, L—G is H, and |
| 301 W is —C(CH$_3$)$_2$—, R$^1$ is Et, R$^2$ is OMe, R$^5$ is H, R$^6$ is H, L—G is C(O)Me, and |
| 302 W is —C(CH$_3$)$_2$—, R$^1$ is Et, R$^2$ is OMe, R$^5$ is H, R$^6$ is H, L—G is C(O)Et, and |
| 303 W is —C(CH$_3$)$_2$—, R$^1$ is Et, R$^2$ is OMe, R$^5$ is H, R$^6$ is H, L—G is C(O)—i-Pr, and |
| 304 W is —C(CH$_3$)$_2$—, R$^1$ is Et, R$^2$ is OMe, R$^5$ is H, R$^6$ is H, L—G is C(O)—t-Bu, and |
| 305 W is —C(CH$_3$)$_2$—, R$^1$ is Et, R$^2$ is OMe, R$^5$ is H, R$^6$ is H, L—G is CO$_2$Me, and |
| 306 W is —C(CH$_3$)$_2$—, R$^1$ is Et, R$^2$ is OMe, R$^5$ is H, R$^6$ is H, L—G is CO$_2$Et, and |
| 307 W is —C(CH$_3$)$_2$—, R$^1$ is Et, R$^2$ is OMe, R$^5$ is H, R$^6$ is H, L—G is CO$_2$—i-Pr, and |
| 308 W is —C(CH$_3$)$_2$—, R$^1$ is Et, R$^2$ is OMe, R$^5$ is H, R$^6$ is H, L—G is CO$_2$—t-Bu, and |
| 309 W is —C(CH$_3$)$_2$—, R$^1$ is Et, R$^2$ is OMe, R$^5$ is H, R$^6$ is H, L—G is SO$_2$Me, and |
| 310 W is —C(CH$_3$)$_2$—, R$^1$ is Et, R$^2$ is CN, R$^5$ is H, R$^6$ is H, L—G is H, and |
| 311 W is —C(CH$_3$)$_2$—, R$^1$ is Et, R$^2$ is CN, R$^5$ is H, R$^6$ is H, L—G is C(O)Me, and |
| 312 W is —C(CH$_3$)$_2$—, R$^1$ is Et, R$^2$ is CN, R$^5$ is H, R$^6$ is H, L—G is C(O)Et, and |
| 313 W is —C(CH$_3$)$_2$—, R$^1$ is Et, R$^2$ is CN, R$^5$ is H, R$^6$ is H, L—G is C(O)—i-Pr, and |
| 314 W is —C(CH$_3$)$_2$—, R$^1$ is Et, R$^2$ is CN, R$^5$ is H, R$^6$ is H, L—G is C(O)—t-Bu, and |
| 315 W is —C(CH$_3$)$_2$—, R$^1$ is Et, R$^2$ is CN, R$^5$ is H, R$^6$ is H, L—G is CO$_2$Me, and |
| 316 W is —C(CH$_3$)$_2$—, R$^1$ is Et, R$^2$ is CN, R$^5$ is H, R$^6$ is H, L—G is CO$_2$Et, and |
| 317 W is —C(CH$_3$)$_2$—, R$^1$ is Et, R$^2$ is CN, R$^5$ is H, R$^6$ is H, L—G is CO$_2$—i-Pr, and |

| Table Row Heading |
|---|
| 318  W is —C(CH$_3$)$_2$—, R$^1$ is Et, R$^2$ is CN, R$^5$ is H, R$^6$ is H, L—G is CO$_2$—t-Bu, and |
| 319  W is —C(CH$_3$)$_2$—, R$^1$ is Et, R$^2$ is CN, R$^5$ is H, R$^6$ is H, L—G is SO$_2$Me, and |
| 320  W is —O—, R$^1$ is Me, R$^2$ is Me, R$^5$ is H, R$^6$ is H, L—G is H, and |
| 321  W is —O—, R$^1$ is Me, R$^2$ is Me, R$^5$ is H, R$^6$ is H, L—G is C(O)Me, and |
| 322  W is —O—, R$^1$ is Me, R$^2$ is Me, R$^5$ is H, R$^6$ is H, L—G is C(O)Et, and |
| 323  W is —O—, R$^1$ is Me, R$^2$ is Me, R$^5$ is H, R$^6$ is H, L—G is C(O)—i-Pr, and |
| 324  W is —O—, R$^1$ is Me, R$^2$ is Me, R$^5$ is H, R$^6$ is H, L—G is C(O)—t-Bu, and |
| 325  W is —O—, R$^1$ is Me, R$^2$ is Me, R$^5$ is H, R$^6$ is H, L—G is CO$_2$Me, and |
| 326  W is —O—, R$^1$ is Me, R$^2$ is Me, R$^5$ is H, R$^6$ is H, L—G is CO$_2$Et, and |
| 327  W is —O—, R$^1$ is Me, R$^2$ is Me, R$^5$ is H, R$^6$ is H, L—G is CO$_2$—i-Pr, and |
| 328  W is —O—, R$^1$ is Me, R$^2$ is Me, R$^5$ is H, R$^6$ is H, L—G is CO$_2$—t-Bu, and |
| 329  W is —O—, R$^1$ is Me, R$^2$ is Me, R$^5$ is H, R$^6$ is H, L—G is SO$_2$Me, and |
| 330  W is —O—, R$^1$ is Me, R$^2$ is H, R$^5$ is H, R$^6$ is H, L—G is H, and |
| 331  W is —O—, R$^1$ is Me, R$^2$ is H, R$^5$ is H, R$^6$ is H, L—G is C(O)Me, and |
| 332  W is —O—, R$^1$ is Me, R$^2$ is H, R$^5$ is H, R$^6$ is H, L—G is C(O)Et, and |
| 333  W is —O—, R$^1$ is Me, R$^2$ is H, R$^5$ is H, R$^6$ is H, L—G is C(O)—i-Pr, and |
| 334  W is —O—, R$^1$ is Me, R$^2$ is H, R$^5$ is H, R$^6$ is H, L—G is C(O)—t-Bu, and |
| 335  W is —O—, R$^1$ is Me, R$^2$ is H, R$^5$ is H, R$^6$ is H, L—G is CO$_2$Me, and |
| 336  W is —O—, R$^1$ is Me, R$^2$ is H, R$^5$ is H, R$^6$ is H, L—G is CO$_2$Et, and |
| 337  W is —O—, R$^1$ is Me, R$^2$ is H, R$^5$ is H, R$^6$ is H, L—G is CO$_2$—i-Pr, and |
| 338  W is —O—, R$^1$ is Me, R$^2$ is H, R$^5$ is H, R$^6$ is H, L—G is CO$_2$—t-Bu, and |
| 339  W is —O—, R$^1$ is Me, R$^2$ is H, R$^5$ is H, R$^6$ is H, L—G is SO$_2$Me, and |
| 340  W is —O—, R$^1$ is Me, R$^2$ is CF$_3$, R$^5$ is H, R$^6$ is H, L—G is H |
| 341  W is —O—, R$^1$ is Me, R$^2$ is CF$_3$, R$^5$ is H, R$^6$ is H, L—G is C(O)Me, and |
| 342  W is —O—, R$^1$ is Me, R$^2$ is CF$_3$, R$^5$ is H, R$^6$ is H, L—G is C(O)Et, and |
| 343  W is —O—, R$^1$ is Me, R$^2$ is CF$_3$, R$^5$ is H, R$^6$ is H, L—G is C(O)—i-Pr, and |
| 344  W is —O—, R$^1$ is Me, R$^2$ is CF$_3$, R$^5$ is H, R$^6$ is H, L—G is C(O)—t-Bu, and |
| 345  W is —O—, R$^1$ is Me, R$^2$ is CF$_3$, R$^5$ is H, R$^6$ is H, L—G is CO$_2$Me, and |
| 346  W is —O—, R$^1$ is Me, R$^2$ is CF$_3$, R$^5$ is H, R$^6$ is H, L—G is CO$_2$Et, and |
| 347  W is —O—, R$^1$ is Me, R$^2$ is CF$_3$, R$^5$ is H, R$^6$ is H, L—G is CO$_2$—i-Pr, and |
| 348  W is —O—, R$^1$ is Me, R$^2$ is CF$_3$, R$^5$ is H, R$^6$ is H, L—G is CO$_2$—t-Bu, and |
| 349  W is —O—, R$^1$ is Me, R$^2$ is CF$_3$, R$^5$ is H, R$^6$ is H, L—G is SO$_2$Me, and |
| 350  W is —O—, R$^1$ is Me, R$^2$ is Cl, R$^5$ is H, R$^6$ is H, L—G is H, and |
| 351  W is —O—, R$^1$ is Me, R$^2$ is Cl, R$^5$ is H, R$^6$ is H, L—G is C(O)Me, and |
| 352  W is —O—, R$^1$ is Me, R$^2$ is Cl, R$^5$ is H, R$^6$ is H, L—G is C(O)Et, and |
| 353  W is —O—, R$^1$ is Me, R$^2$ is Cl, R$^5$ is H, R$^6$ is H, L—G is C(O)—i-Pr, and |
| 354  W is —O—, R$^1$ is Me, R$^2$ is Cl, R$^5$ is H, R$^6$ is H, L—G is C(O)—t-Bu, and |
| 355  W is —O—, R$^1$ is Me, R$^2$ is Cl, R$^5$ is H, R$^6$ is H, L—G is CO$_2$Me, and |
| 356  W is —O—, R$^1$ is Me, R$^2$ is Cl, R$^5$ is H, R$^6$ is H, L—G is CO$_2$Et, and |
| 357  W is —O—, R$^1$ is Me, R$^2$ is Cl, R$^5$ is H, R$^6$ is H, L—G is CO$_2$—i-Pr, and |
| 358  W is —O—, R$^1$ is Me, R$^2$ is Cl, R$^5$ is H, R$^6$ is H, L—G is CO$_2$—t-Bu, and |
| 359  W is —O—, R$^1$ is Me, R$^2$ is Cl, R$^5$ is H, R$^6$ is H, L—G is SO$_2$Me, and |
| 360  W is —O—, R$^1$ is Me, R$^2$ is Br, R$^5$ is H, R$^6$ is H, L—G is H, and |
| 361  W is —O—, R$^1$ is Me, R$^2$ is Br, R$^5$ is H, R$^6$ is H, L—G is C(O)Me, and |
| 362  W is —O—, R$^1$ is Me, R$^2$ is Br, R$^5$ is H, R$^6$ is H, L—G is C(O)Et, and |
| 363  W is —O—, R$^1$ is Me, R$^2$ is Br, R$^5$ is H, R$^6$ is H, L—G is C(O)—i-Pr, and |
| 364  W is —O—, R$^1$ is Me, R$^2$ is Br, R$^5$ is H, R$^6$ is H, L—G is C(O)—t-Bu, and |
| 365  W is —O—, R$^1$ is Me, R$^2$ is Br, R$^5$ is H, R$^6$ is H, L—G is CO$_2$Me, and |
| 366  W is —O—, R$^1$ is Me, R$^2$ is Br, R$^5$ is H, R$^6$ is H, L—G is CO$_2$Et, and |
| 367  W is —O—, R$^1$ is Me, R$^2$ is Br, R$^5$ is H, R$^6$ is H, L—G is CO$_2$—i-Pr, and |
| 368  W is —O—, R$^1$ is Me, R$^2$ is Br, R$^5$ is H, R$^6$ is H, L—G is CO$_2$—t-Bu, and |
| 369  W is —O—, R$^1$ is Me, R$^2$ is Br, R$^5$ is H, R$^6$ is H, L—G is SO$_2$Me, and |
| 370  W is —O—, R$^1$ is Me, R$^2$ is I, R$^5$ is H, R$^6$ is H, L—G is H, and |
| 371  W is —O—, R$^1$ is Me, R$^2$ is I, R$^5$ is H, R$^6$ is H, L—G is C(O)Me, and |
| 372  W is —O—, R$^1$ is Me, R$^2$ is I, R$^5$ is H, R$^6$ is H, L—G is C(O)Et, and |
| 373  W is —O—, R$^1$ is Me, R$^2$ is I, R$^5$ is H, R$^6$ is H, L—G is C(O)—i-Pr, and |
| 374  W is —O—, R$^1$ is Me, R$^2$ is I, R$^5$ is H, R$^6$ is H, L—G is C(O)—t-Bu, and |
| 375  W is —O—, R$^1$ is Me, R$^2$ is I, R$^5$ is H, R$^6$ is H, L—G is CO$_2$Me, and |
| 376  W is —O—, R$^1$ is Me, R$^2$ is I, R$^5$ is H, R$^6$ is H, L—G is CO$_2$Et, and |
| 377  W is —O—, R$^1$ is Me, R$^2$ is I, R$^5$ is H, R$^6$ is H, L—G is CO$_2$—i-Pr, and |
| 378  W is —O—, R$^1$ is Me, R$^2$ is I, R$^5$ is H, R$^6$ is H, L—G is CO$_2$—t-Bu, and |
| 379  W is —O—, R$^1$ is Me, R$^2$ is I, R$^5$ is H, R$^6$ is H, L—G is SO$_2$Me, and |
| 380  W is —O—, R$^1$ is Me, R$^2$ is OMe, R$^5$ is H, R$^6$ is H, L—G is H, and |
| 381  W is —O—, R$^1$ is Me, R$^2$ is OMe, R$^5$ is H, R$^6$ is H, L—G is C(O)Me, and |
| 382  W is —O—, R$^1$ is Me, R$^2$ is OMe, R$^5$ is H, R$^6$ is H, L—G is C(O)Et, and |
| 383  W is —O—, R$^1$ is Me, R$^2$ is OMe, R$^5$ is H, R$^6$ is H, L—G is C(O)—i-Pr, and |
| 384  W is —O—, R$^1$ is Me, R$^2$ is OMe, R$^5$ is H, R$^6$ is H, L—G is C(O)—t-Bu, and |
| 385  W is —O—, R$^1$ is Me, R$^2$ is OMe, R$^5$ is H, R$^6$ is H, L—G is CO$_2$Me, and |
| 386  W is —O—, R$^1$ is Me, R$^2$ is OMe, R$^5$ is H, R$^6$ is H, L—G is CO$_2$Et, and |
| 387  W is —O—, R$^1$ is Me, R$^2$ is OMe, R$^5$ is H, R$^6$ is H, L—G is CO$_2$—i-Pr, and |
| 388  W is —O—, R$^1$ is Me, R$^2$ is OMe, R$^5$ is H, R$^6$ is H, L—G is CO$_2$—t-Bu, and |
| 389  W is —O—, R$^1$ is Me, R$^2$ is OMe, R$^5$ is H, R$^6$ is H, L—G is SO$_2$Me, and |
| 390  W is —O—, R$^1$ is Me, R$^2$ is CN, R$^5$ is H, R$^6$ is H, L—G is H, and |
| 391  W is —O—, R$^1$ is Me, R$^2$ is CN, R$^5$ is H, R$^6$ is H, L—G is C(O)Me, and |
| 392  W is —O—, R$^1$ is Me, R$^2$ is CN, R$^5$ is H, R$^6$ is H, L—G is C(O)Et, and |
| 393  W is —O—, R$^1$ is Me, R$^2$ is CN, R$^5$ is H, R$^6$ is H, L—G is C(O)—i-Pr, and |
| 394  W is —O—, R$^1$ is Me, R$^2$ is CN, R$^5$ is H, R$^6$ is H, L—G is C(O)—t-Bu, and |

-continued

| Table Row Heading |
|---|
| 395 W is —O—, $R^1$ is Me, $R^2$ is CN, $R^5$ is H, $R^6$ is H, L—G is $CO_2Me$, and |
| 396 W is —O—, $R^1$ is Me, $R^2$ is CN, $R^5$ is H, $R^6$ is H, L—G is $CO_2Et$, and |
| 397 W is —O—, $R^1$ is Me, $R^2$ is CN, $R^5$ is H, $R^6$ is H, L—G is $CO_2$—i-Pr, and |
| 398 W is —O—, $R^1$ is Me, $R^2$ is CN, $R^5$ is H, $R^6$ is H, L—G is $CO_2$—t-Bu, and |
| 399 W is —O—, $R^1$ is Me, $R^2$ is CN, $R^5$ is H, $R^6$ is H, L—G is $SO_2Me$, and |
| 400 W is —O—, $R^1$ is Et, $R^2$ is Me, $R^5$ is H, $R^6$ is H, L—G is H, and |
| 401 W is —O—, $R^1$ is Et, $R^2$ is Me, $R^5$ is H, $R^6$ is H, L—G is C(O)Me, and |
| 402 W is —O—, $R^1$ is Et, $R^2$ is Me, $R^5$ is H, $R^6$ is H, L—G is C(O)Et, and |
| 403 W is —O—, $R^1$ is Et, $R^2$ is Me, $R^5$ is H, $R^6$ is H, L—G is C(O)—i-Pr, and |
| 404 W is —O—, $R^1$ is Et, $R^2$ is Me, $R^5$ is H, $R^6$ is H, L—G is C(O)—t-Bu, and |
| 405 W is —O—, $R^1$ is Et, $R^2$ is Me, $R^5$ is H, $R^6$ is H, L—G is $CO_2Me$, and |
| 406 W is —O—, $R^1$ is Et, $R^2$ is Me, $R^5$ is H, $R^6$ is H, L—G is $CO_2Et$, and |
| 407 W is —O—, $R^1$ is Et, $R^2$ is Me, $R^5$ is H, $R^6$ is H, L—G is $CO_2$—i-Pr, and |
| 408 W is —O—, $R^1$ is Et, $R^2$ is Me, $R^5$ is H, $R^6$ is H, L—G is $CO_2$—t-Bu, and |
| 409 W is —O—, $R^1$ is Et, $R^2$ is Me, $R^5$ is H, $R^6$ is H, L—G is $SO_2Me$, and |
| 410 W is —O—, $R^1$ is Et, $R^2$ is H, $R^5$ is H, $R^6$ is H, L—G is H, and |
| 411 W is —O—, $R^1$ is Et, $R^2$ is H, $R^5$ is H, $R^6$ is H, L—G is C(O)Me, and |
| 412 W is —O—, $R^1$ is Et, $R^2$ is H, $R^5$ is H, $R^6$ is H, L—G is C(O)Et, and |
| 413 W is —O—, $R^1$ is Et, $R^2$ is H, $R^5$ is H, $R^6$ is H, L—G is C(O)—i-Pr, and |
| 414 W is —O—, $R^1$ is Et, $R^2$ is H, $R^5$ is H, $R^6$ is H, L—G is C(O)—t-Bu, and |
| 415 W is —O—, $R^1$ is Et, $R^2$ is H, $R^5$ is H, $R^6$ is H, L—G is $CO_2Me$, and |
| 416 W is —O—, $R^1$ is Et, $R^2$ is H, $R^5$ is H, $R^6$ is H, L—G is $CO_2Et$, and |
| 417 W is —O—, $R^1$ is Et, $R^2$ is H, $R^5$ is H, $R^6$ is H, L—G is $CO_2$—i-Pr, and |
| 418 W is —O—, $R^1$ is Et, $R^2$ is H, $R^5$ is H, $R^6$ is H, L—G is $CO_2$—t-Bu, and |
| 419 W is —O—, $R^1$ is Et, $R^2$ is H, $R^5$ is H, $R^6$ is H, L—G is $SO_2Me$, and |
| 420 W is —O—, $R^1$ is Et, $R^2$ is $CF_3$, $R^5$ is H, $R^6$ is H, L—G is H, and |
| 421 W is —O—, $R^1$ is Et, $R^2$ is $CF_3$, $R^5$ is H, $R^6$ is H, L—G is C(O)Me, and |
| 422 W is —O—, $R^1$ is Et, $R^2$ is $CF_3$, $R^5$ is H, $R^6$ is H, L—G is C(O)Et, and |
| 423 W is —O—, $R^1$ is Et, $R^2$ is $CF_3$, $R^5$ is H, $R^6$ is H, L—G is C(O)—i-Pr, and |
| 424 W is —O—, $R^1$ is Et, $R^2$ is $CF_3$, $R^5$ is H, $R^6$ is H, L—G is C(O)—t-Bu, and |
| 425 W is —O—, $R^1$ is Et, $R^2$ is $CF_3$, $R^5$ is H, $R^6$ is H, L—G is $CO_2Me$, and |
| 426 W is —O—, $R^1$ is Et, $R^2$ is $CF_3$, $R^5$ is H, $R^6$ is H, L—G is $CO_2Et$, and |
| 427 W is —O—, $R^1$ is Et, $R^2$ is $CF_3$, $R^5$ is H, $R^6$ is H, L—G is $CO_2$—i-Pr, and |
| 428 W is —O—, $R^1$ is Et, $R^2$ is $CF_3$, $R^5$ is H, $R^6$ is H, L—G is $CO_2$—t-Bu, and |
| 429 W is —O—, $R^1$ is Et, $R^2$ is $CF_3$, $R^5$ is H, $R^6$ is H, L—G is $SO_2Me$, and |
| 430 W is —O—, $R^1$ is Et, $R^2$ is Cl, $R^5$ is H, $R^6$ is H, L—G is H, and |
| 431 W is —O—, $R^1$ is Et, $R^2$ is Cl, $R^5$ is H, $R^6$ is H, L—G is C(O)Me, and |
| 432 W is —O—, $R^1$ is Et, $R^2$ is Cl, $R^5$ is H, $R^6$ is H, L—G is C(O)Et, and |
| 433 W is —O—, $R^1$ is Et, $R^2$ is Cl, $R^5$ is H, $R^6$ is H, L—G is C(O)—i-Pr, and |
| 434 W is —O—, $R^1$ is Et, $R^2$ is Cl, $R^5$ is H, $R^6$ is H, L—G is C(O)—t-Bu, and |
| 435 W is —O—, $R^1$ is Et, $R^2$ is Cl, $R^5$ is H, $R^6$ is H, L—G is $CO_2Me$, and |
| 436 W is —O—, $R^1$ is Et, $R^2$ is Cl, $R^5$ is H, $R^6$ is H, L—G is $CO_2Et$, and |
| 437 W is —O—, $R^1$ is Et, $R^2$ is Cl, $R^5$ is H, $R^6$ is H, L—G is $CO_2$—i-Pr, and |
| 438 W is —O—, $R^1$ is Et, $R^2$ is Cl, $R^5$ is H, $R^6$ is H, L—G is $CO_2$—t-Bu, and |
| 439 W is —O—, $R^1$ is Et, $R^2$ is Cl, $R^5$ is H, $R^6$ is H, L—G is $SO_2Me$, and |
| 440 W is —O—, $R^1$ is Et, $R^2$ is Br, $R^5$ is H, $R^6$ is H, L—G is H, and |
| 441 W is —O—, $R^1$ is Et, $R^2$ is Br, $R^5$ is H, $R^6$ is H, L—G is C(O)Me, and |
| 442 W is —O—, $R^1$ is Et, $R^2$ is Br, $R^5$ is H, $R^6$ is H, L—G is C(O)Et, and |
| 443 W is —O—, $R^1$ is Et, $R^2$ is Br, $R^5$ is H, $R^6$ is H, L—G is C(O)—i-Pr, and |
| 444 W is —O—, $R^1$ is Et, $R^2$ is Br, $R^5$ is H, $R^6$ is H, L—G is C(O)—t-Bu, and |
| 445 W is —O—, $R^1$ is Et, $R^2$ is Br, $R^5$ is H, $R^6$ is H, L—G is $CO_2Me$, and |
| 446 W is —O—, $R^1$ is Et, $R^2$ is Br, $R^5$ is H, $R^6$ is H, L—G is $CO_2Et$, and |
| 447 W is —O—, $R^1$ is Et, $R^2$ is Br, $R^5$ is H, $R^6$ is H, L—G is $CO_2$—i-Pr, and |
| 448 W is —O—, $R^1$ is Et, $R^2$ is Br, $R^5$ is H, $R^6$ is H, L—G is $CO_2$—t-Bu, and |
| 449 W is —O—, $R^1$ is Et, $R^2$ is Br, $R^5$ is H, $R^6$ is H, L—G is $SO_2Me$, and |
| 450 W is —O—, $R^1$ is Et, $R^2$ is I, $R^5$ is H, $R^6$ is H, L—G is H, and |
| 451 W is —O—, $R^1$ is Et, $R^2$ is I, $R^5$ is H, $R^6$ is H, L—G is C(O)Me, and |
| 452 W is —O—, $R^1$ is Et, $R^2$ is I, $R^5$ is H, $R^6$ is H, L—G is C(O)Et, and |
| 453 W is —O—, $R^1$ is Et, $R^2$ is I, $R^5$ is H, $R^6$ is H, L—G is C(O)—i-Pr, and |
| 454 W is —O—, $R^1$ is Et, $R^2$ is I, $R^5$ is H, $R^6$ is H, L—G is C(O)—t-Bu, and |
| 455 W is —O—, $R^1$ is Et, $R^2$ is I, $R^5$ is H, $R^6$ is H, L—G is $CO_2Me$, and |
| 456 W is —O—, $R^1$ is Et, $R^2$ is I, $R^5$ is H, $R^6$ is H, L—G is $CO_2Et$, and |
| 457 W is —O—, $R^1$ is Et, $R^2$ is I, $R^5$ is H, $R^6$ is H, L—G is $CO_2$—i-Pr, and |
| 458 W is —O—, $R^1$ is Et, $R^2$ is I, $R^5$ is H, $R^6$ is H, L—G is $CO_2$—t-Bu, and |
| 459 W is —O—, $R^1$ is Et, $R^2$ is I, $R^5$ is H, $R^6$ is H, L—G is $SO_2Me$, and |
| 460 W is —O—, $R^1$ is Et, $R^2$ is OMe, $R^5$ is H, $R^6$ is H, L—G is H, and |
| 461 W is —O—, $R^1$ is Et, $R^2$ is OMe, $R^5$ is H, $R^6$ is H, L—G is C(O)Me, and |
| 462 W is —O—, $R^1$ is Et, $R^2$ is OMe, $R^5$ is H, $R^6$ is H, L—G is C(O)Et, and |
| 463 W is —O—, $R^1$ is Et, $R^2$ is OMe, $R^5$ is H, $R^6$ is H, L—G is C(O)—i-Pr, and |
| 464 W is —O—, $R^1$ is Et, $R^2$ is OMe, $R^5$ is H, $R^6$ is H, L—G is C(O)—t-Bu, and |
| 465 W is —O—, $R^1$ is Et, $R^2$ is OMe, $R^5$ is H, $R^6$ is H, L—G is $CO_2Me$, and |
| 466 W is —O—, $R^1$ is Et, $R^2$ is OMe, $R^5$ is H, $R^6$ is H, L—G is $CO_2Et$, and |
| 467 W is —O—, $R^1$ is Et, $R^2$ is OMe, $R^5$ is H, $R^6$ is H, L—G is $CO_2$—i-Pr, and |
| 468 W is —O—, $R^1$ is Et, $R^2$ is OMe, $R^5$ is H, $R^6$ is H, L—G is $CO_2$—t-Bu, and |
| 469 W is —O—, $R^1$ is Et, $R^2$ is OMe, $R^5$ is H, $R^6$ is H, L—G is $SO_2Me$, and |
| 470 W is —O—, $R^1$ is Et, $R^2$ is CN, $R^5$ is H, $R^6$ is H, L—G is H, and |
| 471 W is —O—, $R^1$ is Et, $R^2$ is CN, $R^5$ is H, $R^6$ is H, L—G is C(O)Me, and |

| Table Row Heading |
|---|
| 472 W is —O—, $R^1$ is Et, $R^2$ is CN, $R^5$ is H, $R^6$ is H, L—G is C(O)Et, and |
| 473 W is —O—, $R^1$ is Et, $R^2$ is CN, $R^5$ is H, $R^6$ is H, L—G is C(O)—i-Pr, and |
| 474 W is —O—, $R^1$ is Et, $R^2$ is CN, $R^5$ is H, $R^6$ is H, L—G is C(O)—t-Bu, and |
| 475 W is —O—, $R^1$ is Et, $R^2$ is CN, $R^5$ is H, $R^6$ is H, L—G is $CO_2$Me, and |
| 476 W is —O—, $R^1$ is Et, $R^2$ is CN, $R^5$ is H, $R^6$ is H, L—G is $CO_2$Et, and |
| 477 W is —O—, $R^1$ is Et, $R^2$ is CN, $R^5$ is H, $R^6$ is H, L—G is $CO_2$—i-Pr, and |
| 478 W is —O—, $R^1$ is Et, $R^2$ is CN, $R^5$ is H, $R^6$ is H, L—G is $CO_2$—t-Bu, and |
| 479 W is —O—, $R^1$ is Et, $R^2$ is CN, $R^5$ is H, $R^6$ is H, L—G is $SO_2$Me, and |
| 480 W is —CH(CH$_3$)—, $R^1$ is Me, $R^2$ is Me, $R^5$ is H, $R^6$ is H, L—G is H, and |
| 481 W is —CH(CH$_3$)—, $R^1$ is Me, $R^2$ is Me, $R^5$ is H, $R^6$ is H, L—G is C(O)Me, and |
| 482 W is —CH(CH$_3$)—, $R^1$ is Me, $R^2$ is Me, $R^5$ is H, $R^6$ is H, L—G is C(O)Et, and |
| 483 W is —CH(CH$_3$)—, $R^1$ is Me, $R^2$ is Me, $R^5$ is H, $R^6$ is H, L—G is C(O)—i-Pr, and |
| 484 W is —CH(CH$_3$)—, $R^1$ is Me, $R^2$ is Me, $R^5$ is H, $R^6$ is H, L—G is C(O)—t-Bu, and |
| 485 W is —CH(CH$_3$)—, $R^1$ is Me, $R^2$ is Me, $R^5$ is H, $R^6$ is H, L—G is $CO_2$Me, and |
| 486 W is —CH(CH$_3$)—, $R^1$ is Me, $R^2$ is Me, $R^5$ is H, $R^6$ is H, L—G is $CO_2$Et, and |
| 487 W is —CH(CH$_3$)—, $R^1$ is Me, $R^2$ is Me, $R^5$ is H, $R^6$ is H, L—G is $CO_2$—i-Pr, and |
| 488 W is —CH(CH$_3$)—, $R^1$ is Me, $R^2$ is Me, $R^5$ is H, $R^6$ is H, L—G is $CO_2$—t-Bu, and |
| 489 W is —CH(CH$_3$)—, $R^1$ is Me, $R^2$ is Me, $R^5$ is H, $R^6$ is H, L—G is $SO_2$Me, and |
| 490 W is —CH(CH$_3$)—, $R^1$ is Me, $R^2$ is H, $R^5$ is H, $R^6$ is H, L—G is H, and |
| 491 W is —CH(CH$_3$)—, $R^1$ is Me, $R^2$ is H, $R^5$ is H, $R^6$ is H, L—G is C(O)Me, and |
| 492 W is —CH(CH$_3$)—, $R^1$ is Me, $R^2$ is H, $R^5$ is H, $R^6$ is H, L—G is C(O)Et, and |
| 493 W is —CH(CH$_3$)—, $R^1$ is Me, $R^2$ is H, $R^5$ is H, $R^6$ is H, L—G is C(O)—i-Pr, and |
| 494 W is —CH(CH$_3$)—, $R^1$ is Me, $R^2$ is H, $R^5$ is H, $R^6$ is H, L—G is C(O)—t-Bu, and |
| 495 W is —CH(CH$_3$)—, $R^1$ is Me, $R^2$ is H, $R^5$ is H, $R^6$ is H, L—G is $CO_2$Me, and |
| 496 W is —CH(CH$_3$)—, $R^1$ is Me, $R^2$ is H, $R^5$ is H, $R^6$ is H, L—G is $CO_2$Et, and |
| 497 W is —CH(CH$_3$)—, $R^1$ is Me, $R^2$ is H, $R^5$ is H, $R^6$ is H, L—G is $CO_2$—i-Pr, and |
| 498 W is —CH(CH$_3$)—, $R^1$ is Me, $R^2$ is H, $R^5$ is H, $R^6$ is H, L—G is $CO_2$—t-Bu, and |
| 499 W is —CH(CH$_3$)—, $R^1$ is Me, $R^2$ is H, $R^5$ is H, $R^6$ is H, L—G is $SO_2$Me, and |
| 500 W is —CH(CH$_3$)—, $R^1$ is Me, $R^2$ is CF$_3$, $R^5$ is H, $R^6$ is H, L—G is H, and |
| 501 W is —CH(CH$_3$)—, $R^1$ is Me, $R^2$ is CF$_3$, $R^5$ is H, $R^6$ is H, L—G is C(O)Me, and |
| 502 W is —CH(CH$_3$)—, $R^1$ is Me, $R^2$ is CF$_3$, $R^5$ is H, $R^6$ is H, L—G is C(O)Et, and |
| 503 W is —CH(CH$_3$)—, $R^1$ is Me, $R^2$ is CF$_3$, $R^5$ is H, $R^6$ is H, L—G is C(O)—i-Pr, and |
| 504 W is —CH(CH$_3$)—, $R^1$ is Me, $R^2$ is CF$_3$, $R^5$ is H, $R^6$ is H, L—G is C(O)—t-Bu, and |
| 505 W is —CH(CH$_3$)—, $R^1$ is Me, $R^2$ is CF$_3$, $R^5$ is H, $R^6$ is H, L—G is $CO_2$Me, and |
| 506 W is —CH(CH$_3$)—, $R^1$ is Me, $R^2$ is CF$_3$, $R^5$ is H, $R^6$ is H, L—G is $CO_2$Et, and |
| 507 W is —CH(CH$_3$)—, $R^1$ is Me, $R^2$ is CF$_3$, $R^5$ is H, $R^6$ is H, L—G is $CO_2$—i-Pr, and |
| 508 W is —CH(CH$_3$)—, $R^1$ is Me, $R^2$ is CF$_3$, $R^5$ is H, $R^6$ is H, L—G is $CO_2$—t-Bu, and |
| 509 W is —CH(CH$_3$)—, $R^1$ is Me, $R^2$ is CF$_3$, $R^5$ is H, $R^6$ is H, L—G is $SO_2$Me, and |
| 510 W is —CH(CH$_3$)—, $R^1$ is Me, $R^2$ is Cl, $R^5$ is H, $R^6$ is H, L—G is H, and |
| 511 W is —CH(CH$_3$)—, $R^1$ is Me, $R^2$ is Cl, $R^5$ is H, $R^6$ is H, L—G is C(O)Me, and |
| 512 W is —CH(CH$_3$)—, $R^1$ is Me, $R^2$ is Cl, $R^5$ is H, $R^6$ is H, L—G is C(O)Et, and |
| 513 W is —CH(CH$_3$)—, $R^1$ is Me, $R^2$ is Cl, $R^5$ is H, $R^6$ is H, L—G is C(O)—i-Pr, and |
| 514 W is —CH(CH$_3$)—, $R^1$ is Me, $R^2$ is Cl, $R^5$ is H, $R^6$ is H, L—G is C(O)—t-Bu, and |
| 515 W is —CH(CH$_3$)—, $R^1$ is Me, $R^2$ is Cl, $R^5$ is H, $R^6$ is H, L—G is $CO_2$Me, and |
| 516 W is —CH(CH$_3$)—, $R^1$ is Me, $R^2$ is Cl, $R^5$ is H, $R^6$ is H, L—G is $CO_2$Et, and |
| 517 W is —CH(CH$_3$)—, $R^1$ is Me, $R^2$ is Cl, $R^5$ is H, $R^6$ is H, L—G is $CO_2$—i-Pr, and |
| 518 W is —CH(CH$_3$)—, $R^1$ is Me, $R^2$ is Cl, $R^5$ is H, $R^6$ is H, L—G is $CO_2$—t-Bu, and |
| 519 W is —CH(CH$_3$)—, $R^1$ is Me, $R^2$ is Cl, $R^5$ is H, $R^6$ is H, L—G is $SO_2$Me, and |
| 520 W is —CH(CH$_3$)—, $R^1$ is Me, $R^2$ is Br, $R^5$ is H, $R^6$ is H, L—G is H, and |
| 521 W is —CH(CH$_3$)—, $R^1$ is Me, $R^2$ is Br, $R^5$ is H, $R^6$ is H, L—G is C(O)Me, and |
| 522 W is —CH(CH$_3$)—, $R^1$ is Me, $R^2$ is Br, $R^5$ is H, $R^6$ is H, L—G is C(O)Et, and |
| 523 W is —CH(CH$_3$)—, $R^1$ is Me, $R^2$ is Br, $R^5$ is H, $R^6$ is H, L—G is C(O)—i-Pr, and |
| 524 W is —CH(CH$_3$)—, $R^1$ is Me, $R^2$ is Br, $R^5$ is H, $R^6$ is H, L—G is C(O)—t-Bu, and |
| 525 W is —CH(CH$_3$)—, $R^1$ is Me, $R^2$ is Br, $R^5$ is H, $R^6$ is H, L—G is $CO_2$Me, and |
| 526 W is —CH(CH$_3$)—, $R^1$ is Me, $R^2$ is Br, $R^5$ is H, $R^6$ is H, L—G is $CO_2$Et, and |
| 527 W is —CH(CH$_3$)—, $R^1$ is Me, $R^2$ is Br, $R^5$ is H, $R^6$ is H, L—G is $CO_2$—i-Pr, and |
| 528 W is —CH(CH$_3$)—, $R^1$ is Me, $R^2$ is Br, $R^5$ is H, $R^6$ is H, L—G is $CO_2$—t-Bu, and |
| 529 W is —CH(CH$_3$)—, $R^1$ is Me, $R^2$ is Br, $R^5$ is H, $R^6$ is H, L—G is $SO_2$Me, and |
| 530 W is —CH(CH$_3$)—, $R^1$ is Me, $R^2$ is I, $R^5$ is H, $R^6$ is H, L—G is H, and |
| 531 W is —CH(CH$_3$)—, $R^1$ is Me, $R^2$ is I, $R^5$ is H, $R^6$ is H, L—G is C(O)Me, and |
| 532 W is —CH(CH$_3$)—, $R^1$ is Me, $R^2$ is I, $R^5$ is H, $R^6$ is H, L—G is C(O)Et, and |
| 533 W is —CH(CH$_3$)—, $R^1$ is Me, $R^2$ is I, $R^5$ is H, $R^6$ is H, L—G is C(O)—i-Pr, and |
| 534 W is —CH(CH$_3$)—, $R^1$ is Me, $R^2$ is I, $R^5$ is H, $R^6$ is H, L—G is C(O)—t-Bu, and |
| 535 W is —CH(CH$_3$)—, $R^1$ is Me, $R^2$ is I, $R^5$ is H, $R^6$ is H, L—G is $CO_2$Me, and |
| 536 W is —CH(CH$_3$)—, $R^1$ is Me, $R^2$ is I, $R^5$ is H, $R^6$ is H, L—G is $CO_2$Et, and |
| 537 W is —CH(CH$_3$)—, $R^1$ is Me, $R^2$ is I, $R^5$ is H, $R^6$ is H, L—G is $CO_2$—i-Pr, and |
| 538 W is —CH(CH$_3$)—, $R^1$ is Me, $R^2$ is I, $R^5$ is H, $R^6$ is H, L—G is $CO_2$—t-Bu, and |
| 539 W is —CH(CH$_3$)—, $R^1$ is Me, $R^2$ is I, $R^5$ is H, $R^6$ is H, L—G is $SO_2$Me, and |
| 540 W is —CH(CH$_3$)—, $R^1$ is Me, $R^2$ is OMe, $R^5$ is H, $R^6$ is H, L—G is H, and |
| 541 W is —CH(CH$_3$)—, $R^1$ is Me, $R^2$ is OMe, $R^5$ is H, $R^6$ is H, L—G is C(O)Me, and |
| 542 W is —CH(CH$_3$)—, $R^1$ is Me, $R^2$ is OMe, $R^5$ is H, $R^6$ is H, L—G is C(O)Et, and |
| 543 W is —CH(CH$_3$)—, $R^1$ is Me, $R^2$ is OMe, $R^5$ is H, $R^6$ is H, L—G is C(O)—i-Pr, and |
| 544 W is —CH(CH$_3$)—, $R^1$ is Me, $R^2$ is OMe, $R^5$ is H, $R^6$ is H, L—G is C(O)—t-Bu, and |
| 545 W is —CH(CH$_3$)—, $R^1$ is Me, $R^2$ is OMe, $R^5$ is H, $R^6$ is H, L—G is $CO_2$Me, and |
| 546 W is —CH(CH$_3$)—, $R^1$ is Me, $R^2$ is OMe, $R^5$ is H, $R^6$ is H, L—G is $CO_2$Et, and |
| 547 W is —CH(CH$_3$)—, $R^1$ is Me, $R^2$ is OMe, $R^5$ is H, $R^6$ is H, L—G is $CO_2$—i-Pr, and |
| 548 W is —CH(CH$_3$)—, $R^1$ is Me, $R^2$ is OMe, $R^5$ is H, $R^6$ is H, L—G is $CO_2$—t-Bu, and |

| Table Row Heading |
| --- |
| 549 W is —CH(CH$_3$)—, R$^1$ is Me, R$^2$ is OMe, R$^5$ is H, R$^6$ is H, L—G is SO$_2$Me, and |
| 550 W is —CH(CH$_3$)—, R$^1$ is Me, R$^2$ is CN, R$^5$ is H, R$^6$ is H, L—G is H, and |
| 551 W is —CH(CH$_3$)—, R$^1$ is Me, R$^2$ is CN, R$^5$ is H, R$^6$ is H, L—G is C(O)Me, and |
| 552 W is —CH(CH$_3$)—, R$^1$ is Me, R$^2$ is CN, R$^5$ is H, R$^6$ is H, L—G is C(O)Et, and |
| 553 W is —CH(CH$_3$)—, R$^1$ is Me, R$^2$ is CN, R$^5$ is H, R$^6$ is H, L—G is C(O)—i-Pr, and |
| 554 W is —CH(CH$_3$)—, R$^1$ is Me, R$^2$ is CN, R$^5$ is H, R$^6$ is H, L—G is C(O)—t-Bu, and |
| 555 W is —CH(CH$_3$)—, R$^1$ is Me, R$^2$ is CN, R$^5$ is H, R$^6$ is H, L—G is CO$_2$Me, and |
| 556 W is —CH(CH$_3$)—, R$^1$ is Me, R$^2$ is CN, R$^5$ is H, R$^6$ is H, L—G is CO$_2$Et, and |
| 557 W is —CH(CH$_3$)—, R$^1$ is Me, R$^2$ is CN, R$^5$ is H, R$^6$ is H, L—G is CO$_2$—i-Pr, and |
| 558 W is —CH(CH$_3$)—, R$^1$ is Me, R$^2$ is CN, R$^5$ is H, R$^6$ is H, L—G is CO$_2$—t-Bu, and |
| 559 W is —CH(CH$_3$)—, R$^1$ is Me, R$^2$ is CN, R$^5$ is H, R$^6$ is H, L—G is SO$_2$Me, and |
| 560 W is —CH(CH$_3$)—, R$^1$ is Et, R$^2$ is Me, R$^5$ is H, R$^6$ is H, L—G is H, and |
| 561 W is —CH(CH$_3$)—, R$^1$ is Et, R$^2$ is Me, R$^5$ is H, R$^6$ is H, L—G is C(O)Me, and |
| 562 W is —CH(CH$_3$)—, R$^1$ is Et, R$^2$ is Me, R$^5$ is H, R$^6$ is H, L—G is C(O)Et, and |
| 563 W is —CH(CH$_3$)—, R$^1$ is Et, R$^2$ is Me, R$^5$ is H, R$^6$ is H, L—G is C(O)—i-Pr, and |
| 564 W is —CH(CH$_3$)—, R$^1$ is Et, R$^2$ is Me, R$^5$ is H, R$^6$ is H, L—G is C(O)—t-Bu, and |
| 565 W is —CH(CH$_3$)—, R$^1$ is Et, R$^2$ is Me, R$^5$ is H, R$^6$ is H, L—G is CO$_2$Me, and |
| 566 W is —CH(CH$_3$)—, R$^1$ is Et, R$^2$ is Me, R$^5$ is H, R$^6$ is H, L—G is CO$_2$Et, and |
| 567 W is —CH(CH$_3$)—, R$^1$ is Et, R$^2$ is Me, R$^5$ is H, R$^6$ is H, L—G is CO$_2$—i-Pr, and |
| 568 W is —CH(CH$_3$)—, R$^1$ is Et, R$^2$ is Me, R$^5$ is H, R$^6$ is H, L—G is CO$_2$—t-Bu, and |
| 569 W is —CH(CH$_3$)—, R$^1$ is Et, R$^2$ is Me, R$^5$ is H, R$^6$ is H, L—G is SO$_2$Me, and |
| 570 W is —CH(CH$_3$)—, R$^1$ is Et, R$^2$ is H, R$^5$ is H, R$^6$ is H, L—G is H, and |
| 571 W is —CH(CH$_3$)—, R$^1$ is Et, R$^2$ is H, R$^5$ is H, R$^6$ is H, L—G is C(O)Me, and |
| 572 W is —CH(CH$_3$)—, R$^1$ is Et, R$^2$ is H, R$^5$ is H, R$^6$ is H, L—G is C(O)Et, and |
| 573 W is —CH(CH$_3$)—, R$^1$ is Et, R$^2$ is H, R$^5$ is H, R$^6$ is H, L—G is C(O)—i-Pr, and |
| 574 W is —CH(CH$_3$)—, R$^1$ is Et, R$^2$ is H, R$^5$ is H, R$^6$ is H, L—G is C(O)—t-Bu, and |
| 575 W is —CH(CH$_3$)—, R$^1$ is Et, R$^2$ is H, R$^5$ is H, R$^6$ is H, L—G is CO$_2$Me, and |
| 576 W is —CH(CH$_3$)—, R$^1$ is Et, R$^2$ is H, R$^5$ is H, R$^6$ is H, L—G is CO$_2$Et, and |
| 577 W is —CH(CH$_3$)—, R$^1$ is Et, R$^2$ is H, R$^5$ is H, R$^6$ is H, L—G is CO$_2$—i-Pr, and |
| 578 W is —CH(CH$_3$)—, R$^1$ is Et, R$^2$ is H, R$^5$ is H, R$^6$ is H, L—G is CO$_2$—t-Bu, and |
| 579 W is —CH(CH$_3$)—, R$^1$ is Et, R$^2$ is H, R$^5$ is H, R$^6$ is H, L—G is SO$_2$Me, and |
| 580 W is —CH(CH$_3$)—, R$^1$ is Et, R$^2$ is CF$_3$, R$^5$ is H, R$^6$ is H, L—G is H, and |
| 581 W is —CH(CH$_3$)—, R$^1$ is Et, R$^2$ is CF$_3$, R$^5$ is H, R$^6$ is H, L—G is C(O)Me, and |
| 582 W is —CH(CH$_3$)—, R$^1$ is Et, R$^2$ is CF$_3$, R$^5$ is H, R$^6$ is H, L—G is C(O)Et, and |
| 583 W is —CH(CH$_3$)—, R$^1$ is Et, R$^2$ is CF$_3$, R$^5$ is H, R$^6$ is H, L—G is C(O)—i-Pr, and |
| 584 W is —CH(CH$_3$)—, R$^1$ is Et, R$^2$ is CF$_3$, R$^5$ is H, R$^6$ is H, L—G is C(O)—t-Bu, and |
| 585 W is —CH(CH$_3$)—, R$^1$ is Et, R$^2$ is CF$_3$, R$^5$ is H, R$^6$ is H, L—G is CO$_2$Me, and |
| 586 W is —CH(CH$_3$)—, R$^1$ is Et, R$^2$ is CF$_3$, R$^5$ is H, R$^6$ is H, L—G is CO$_2$Et, and |
| 587 W is —CH(CH$_3$)—, R$^1$ is Et, R$^2$ is CF$_3$, R$^5$ is H, R$^6$ is H, L—G is CO$_2$—i-Pr, and |
| 588 W is —CH(CH$_3$)—, R$^1$ is Et, R$^2$ is CF$_3$, R$^5$ is H, R$^6$ is H, L—G is CO$_2$—t-Bu, and |
| 589 W is —CH(CH$_3$)—, R$^1$ is Et, R$^2$ is CF$_3$, R$^5$ is H, R$^6$ is H, L—G is SO$_2$Me, and |
| 590 W is —CH(CH$_3$)—, R$^1$ is Et, R$^2$ is Cl, R$^5$ is H, R$^6$ is H, L—G is H, and |
| 591 W is —CH(CH$_3$)—, R$^1$ is Et, R$^2$ is Cl, R$^5$ is H, R$^6$ is H, L—G is C(O)Me, and |
| 592 W is —CH(CH$_3$)—, R$^1$ is Et, R$^2$ is Cl, R$^5$ is H, R$^6$ is H, L—G is C(O)Et, and |
| 593 W is —CH(CH$_3$)—, R$^1$ is Et, R$^2$ is Cl, R$^5$ is H, R$^6$ is H, L—G is C(O)—i-Pr, and |
| 594 W is —CH(CH$_3$)—, R$^1$ is Et, R$^2$ is Cl, R$^5$ is H, R$^6$ is H, L—G is C(O)—t-Bu, and |
| 595 W is —CH(CH$_3$)—, R$^1$ is Et, R$^2$ is Cl, R$^5$ is H, R$^6$ is H, L—G is CO$_2$Me, and |
| 596 W is —CH(CH$_3$)—, R$^1$ is Et, R$^2$ is Cl, R$^5$ is H, R$^6$ is H, L—G is CO$_2$Et, and |
| 597 W is —CH(CH$_3$)—, R$^1$ is Et, R$^2$ is Cl, R$^5$ is H, R$^6$ is H, L—G is CO$_2$—i-Pr, and |
| 598 W is —CH(CH$_3$)—, R$^1$ is Et, R$^2$ is Cl, R$^5$ is H, R$^6$ is H, L—G is CO$_2$—t-Bu, and |
| 599 W is —CH(CH$_3$)—, R$^1$ is Et, R$^2$ is Cl, R$^5$ is H, R$^6$ is H, L—G is SO$_2$Me, and |
| 600 W is —CH(CH$_3$)—, R$^1$ is Et, R$^2$ is Br, R$^5$ is H, R$^6$ is H, L—G is H, and |
| 601 W is —CH(CH$_3$)—, R$^1$ is Et, R$^2$ is Br, R$^5$ is H, R$^6$ is H, L—G is C(O)Me, and |
| 602 W is —CH(CH$_3$)—, R$^1$ is Et, R$^2$ is Br, R$^5$ is H, R$^6$ is H, L—G is C(O)Et, and |
| 603 W is —CH(CH$_3$)—, R$^1$ is Et, R$^2$ is Br, R$^5$ is H, R$^6$ is H, L—G is C(O)—i-Pr, and |
| 604 W is —CH(CH$_3$)—, R$^1$ is Et, R$^2$ is Br, R$^5$ is H, R$^6$ is H, L—G is C(O)—t-Bu, and |
| 605 W is —CH(CH$_3$)—, R$^1$ is Et, R$^2$ is Br, R$^5$ is H, R$^6$ is H, L—G is CO$_2$Me, and |
| 606 W is —CH(CH$_3$)—, R$^1$ is Et, R$^2$ is Br, R$^5$ is H, R$^6$ is H, L—G is CO$_2$Et, and |
| 607 W is —CH(CH$_3$)—, R$^1$ is Et, R$^2$ is Br, R$^5$ is H, R$^6$ is H, L—G is CO$_2$—i-Pr, and |
| 608 W is —CH(CH$_3$)—, R$^1$ is Et, R$^2$ is Br, R$^5$ is H, R$^6$ is H, L—G is CO$_2$—t-Bu, and |
| 609 W is —CH(CH$_3$)—, R$^1$ is Et, R$^2$ is Br, R$^5$ is H, R$^6$ is H, L—G is SO$_2$Me, and |
| 610 W is —CH(CH$_3$)—, R$^1$ is Et, R$^2$ is I, R$^5$ is H, R$^6$ is H, L—G is H, and |
| 611 W is —CH(CH$_3$)—, R$^1$ is Et, R$^2$ is I, R$^5$ is H, R$^6$ is H, L—G is C(O)Me, and |
| 612 W is —CH(CH$_3$)—, R$^1$ is Et, R$^2$ is I, R$^5$ is H, R$^6$ is H, L—G is C(O)Et, and |
| 613 W is —CH(CH$_3$)—, R$^1$ is Et, R$^2$ is I, R$^5$ is H, R$^6$ is H, L—G is C(O)—i-Pr, and |
| 614 W is —CH(CH$_3$)—, R$^1$ is Et, R$^2$ is I, R$^5$ is H, R$^6$ is H, L—G is C(O)—t-Bu, and |
| 615 W is —CH(CH$_3$)—, R$^1$ is Et, R$^2$ is I, R$^5$ is H, R$^6$ is H, L—G is CO$_2$Me, and |
| 616 W is —CH(CH$_3$)—, R$^1$ is Et, R$^2$ is I, R$^5$ is H, R$^6$ is H, L—G is CO$_2$Et, and |
| 617 W is —CH(CH$_3$)—, R$^1$ is Et, R$^2$ is I, R$^5$ is H, R$^6$ is H, L—G is CO$_2$—i-Pr, and |
| 618 W is —CH(CH$_3$)—, R$^1$ is Et, R$^2$ is I, R$^5$ is H, R$^6$ is H, L—G is CO$_2$—t-Bu, and |
| 619 W is —CH(CH$_3$)—, R$^1$ is Et, R$^2$ is I, R$^5$ is H, R$^6$ is H, L—G is SO$_2$Me, and |
| 620 W is —CH(CH$_3$)—, R$^1$ is Et, R$^2$ is OMe, R$^5$ is H, R$^6$ is H, L—G is H, and |
| 621 W is —CH(CH$_3$)—, R$^1$ is Et, R$^2$ is OMe, R$^5$ is H, R$^6$ is H, L—G is C(O)Me, and |
| 622 W is —CH(CH$_3$)—, R$^1$ is Et, R$^2$ is OMe, R$^5$ is H, R$^6$ is H, L—G is C(O)Et, and |
| 623 W is —CH(CH$_3$)—, R$^1$ is Et, R$^2$ is OMe, R$^5$ is H, R$^6$ is H, L—G is C(O)—i-Pr, and |
| 624 W is —CH(CH$_3$)—, R$^1$ is Et, R$^2$ is OMe, R$^5$ is H, R$^6$ is H, L—G is C(O)—t-Bu, and |
| 625 W is —CH(CH$_3$)—, R$^1$ is Et, R$^2$ is OMe, R$^5$ is H, R$^6$ is H, L—G is CO$_2$Me, and |

-continued

| Table Row Heading |
|---|
| 626  W is —CH(CH$_3$)—, R$^1$ is Et, R$^2$ is OMe, R$^5$ is H, R$^6$ is H, L—G is CO$_2$Et, and |
| 627  W is —CH(CH$_3$)—, R$^1$ is Et, R$^2$ is OMe, R$^5$ is H, R$^6$ is H, L—G is CO$_2$—i-Pr, and |
| 628  W is —CH(CH$_3$)—, R$^1$ is Et, R$^2$ is OMe, R$^5$ is H, R$^6$ is H, L—G is CO$_2$—t-Bu, and |
| 629  W is —CH(CH$_3$)—, R$^1$ is Et, R$^2$ is OMe, R$^5$ is H, R$^6$ is H, L—G is SO$_2$Me, and |
| 630  W is —CH(CH$_3$)—, R$^1$ is Et, R$^2$ is CN, R$^5$ is H, R$^6$ is H, L—G is H, and |
| 631  W is —CH(CH$_3$)—, R$^1$ is Et, R$^2$ is CN, R$^5$ is H, R$^6$ is H, L—G is C(O)Me, and |
| 632  W is —CH(CH$_3$)—, R$^1$ is Et, R$^2$ is CN, R$^5$ is H, R$^6$ is H, L—G is C(O)Et, and |
| 633  W is —CH(CH$_3$)—, R$^1$ is Et, R$^2$ is CN, R$^5$ is H, R$^6$ is H, L—G is C(O)—i-Pr, and |
| 634  W is —CH(CH$_3$)—, R$^1$ is Et, R$^2$ is CN, R$^5$ is H, R$^6$ is H, L—G is C(O)—t-Bu, and |
| 635  W is —CH(CH$_3$)—, R$^1$ is Et, R$^2$ is CN, R$^5$ is H, R$^6$ is H, L—G is CO$_2$Me, and |
| 636  W is —CH(CH$_3$)—, R$^1$ is Et, R$^2$ is CN, R$^5$ is H, R$^6$ is H, L—G is CO$_2$Et, and |
| 637  W is —CH(CH$_3$)—, R$^1$ is Et, R$^2$ is CN, R$^5$ is H, R$^6$ is H, L—G is CO$_2$—i-Pr, and |
| 638  W is —CH(CH$_3$)—, R$^1$ is Et, R$^2$ is CN, R$^5$ is H, R$^6$ is H, L—G is CO$_2$—t-Bu, and |
| 639  W is —CH(CH$_3$)—, R$^1$ is Et, R$^2$ is CN, R$^5$ is H, R$^6$ is H, L—G is SO$_2$Me, and |
| 640  W is —CH$_2$—, R$^1$ is Me, R$^2$ is Me, R$^5$ is CH$_3$, R$^6$ is H, L—G is H, and |
| 641  W is —CH$_2$—, R$^1$ is Me, R$^2$ is Me, R$^5$ is CH$_3$, R$^6$ is H, L—G is C(O)Me, and |
| 642  W is —CH$_2$—, R$^1$ is Me, R$^2$ is Me, R$^5$ is CH$_3$, R$^6$ is H, L—G is C(O)Et, and |
| 643  W is —CH$_2$—, R$^1$ is Me, R$^2$ is Me, R$^5$ is CH$_3$, R$^6$ is H, L—G is C(O)—i-Pr, and |
| 644  W is —CH$_2$—, R$^1$ is Me, R$^2$ is Me, R$^5$ is CH$_3$, R$^6$ is H, L—G is C(O)—t-Bu, and |
| 645  W is —CH$_2$—, R$^1$ is Me, R$^2$ is Me, R$^5$ is CH$_3$, R$^6$ is H, L—G is CO$_2$Me, and |
| 646  W is —CH$_2$—, R$^1$ is Me, R$^2$ is Me, R$^5$ is CH$_3$, R$^6$ is H, L—G is CO$_2$Et, and |
| 647  W is —CH$_2$—, R$^1$ is Me, R$^2$ is Me, R$^5$ is CH$_3$, R$^6$ is H, L—G is CO$_2$—i-Pr, and |
| 648  W is —CH$_2$—, R$^1$ is Me, R$^2$ is Me, R$^5$ is CH$_3$, R$^6$ is H, L—G is CO$_2$—t-Bu, and |
| 649  W is —CH$_2$—, R$^1$ is Me, R$^2$ is Me, R$^5$ is CH$_3$, R$^6$ is H, L—G is SO$_2$Me, and |
| 650  W is —CH$_2$—, R$^1$ is Me, R$^2$ is H, R$^5$ is CH$_3$, R$^6$ is H, L—G is H, and |
| 651  W is —CH$_2$—, R$^1$ is Me, R$^2$ is H, R$^5$ is CH$_3$, R$^6$ is H, L—G is C(O)Me, and |
| 652  W is —CH$_2$—, R$^1$ is Me, R$^2$ is H, R$^5$ is CH$_3$, R$^6$ is H, L—G is C(O)Et, and |
| 653  W is —CH$_2$—, R$^1$ is Me, R$^2$ is H, R$^5$ is CH$_3$, R$^6$ is H, L—G is C(O)—i-Pr, and |
| 654  W is —CH$_2$—, R$^1$ is Me, R$^2$ is H, R$^5$ is CH$_3$, R$^6$ is H, L—G is C(O)—t-Bu, and |
| 655  W is —CH$_2$—, R$^1$ is Me, R$^2$ is H, R$^5$ is CH$_3$, R$^6$ is H, L—G is CO$_2$Me, and |
| 656  W is —CH$_2$—, R$^1$ is Me, R$^2$ is H, R$^5$ is CH$_3$, R$^6$ is H, L—G is CO$_2$Et, and |
| 657  W is —CH$_2$—, R$^1$ is Me, R$^2$ is H, R$^5$ is CH$_3$, R$^6$ is H, L—G is CO$_2$—i-Pr, and |
| 658  W is —CH$_2$—, R$^1$ is Me, R$^2$ is H, R$^5$ is CH$_3$, R$^6$ is H, L—G is CO$_2$—t-Bu, and |
| 659  W is —CH$_2$—, R$^1$ is Me, R$^2$ is H, R$^5$ is CH$_3$, R$^6$ is H, L—G is SO$_2$Me, and |
| 660  W is —CH$_2$—, R$^1$ is Me, R$^2$ is CF$_3$, R$^5$ is CH$_3$, R$^6$ is H, L—G is H, and |
| 661  W is —CH$_2$—, R$^1$ is Me, R$^2$ is CF$_3$, R$^5$ is CH$_3$, R$^6$ is H, L—G is C(O)Me, and |
| 662  W is —CH$_2$—, R$^1$ is Me, R$^2$ is CF$_3$, R$^5$ is CH$_3$, R$^6$ is H, L—G is C(O)Et, and |
| 663  W is —CH$_2$—, R$^1$ is Me, R$^2$ is CF$_3$, R$^5$ is CH$_3$, R$^6$ is H, L—G is C(O)—i-Pr, and |
| 664  W is —CH$_2$—, R$^1$ is Me, R$^2$ is CF$_3$, R$^5$ is CH$_3$, R$^6$ is H, L—G is C(O)—t-Bu, and |
| 665  W is —CH$_2$—, R$^1$ is Me, R$^2$ is CF$_3$, R$^5$ is CH$_3$, R$^6$ is H, L—G is CO$_2$Me, and |
| 666  W is —CH$_2$—, R$^1$ is Me, R$^2$ is CF$_3$, R$^5$ is CH$_3$, R$^6$ is H, L—G is CO$_2$Et, and |
| 667  W is —CH$_2$—, R$^1$ is Me, R$^2$ is CF$_3$, R$^5$ is CH$_3$, R$^6$ is H, L—G is CO$_2$—i-Pr, and |
| 668  W is —CH$_2$—, R$^1$ is Me, R$^2$ is CF$_3$, R$^5$ is CH$_3$, R$^6$ is H, L—G is CO$_2$—t-Bu, and |
| 669  W is —CH$_2$—, R$^1$ is Me, R$^2$ is CF$_3$, R$^5$ is CH$_3$, R$^6$ is H, L—G is SO$_2$Me, and |
| 670  W is —CH$_2$—, R$^1$ is Me, R$^2$ is Cl, R$^5$ is CH$_3$, R$^6$ is H, L—G is H, and |
| 671  W is —CH$_2$—, R$^1$ is Me, R$^2$ is Cl, R$^5$ is CH$_3$, R$^6$ is H, L—G is C(O)Me, and |
| 672  W is —CH$_2$—, R$^1$ is Me, R$^2$ is Cl, R$^5$ is CH$_3$, R$^6$ is H, L—G is C(O)Et, and |
| 673  W is —CH$_2$—, R$^1$ is Me, R$^2$ is Cl, R$^5$ is CH$_3$, R$^6$ is H, L—G is C(O)—i-Pr, and |
| 674  W is —CH$_2$—, R$^1$ is Me, R$^2$ is Cl, R$^5$ is CH$_3$, R$^6$ is H, L—G is C(O)—t-Bu, and |
| 675  W is —CH$_2$—, R$^1$ is Me, R$^2$ is Cl, R$^5$ is CH$_3$, R$^6$ is H, L—G is CO$_2$Me, and |
| 676  W is —CH$_2$—, R$^1$ is Me, R$^2$ is Cl, R$^5$ is CH$_3$, R$^6$ is H, L—G is CO$_2$Et, and |
| 677  W is —CH$_2$—, R$^1$ is Me, R$^2$ is Cl, R$^5$ is CH$_3$, R$^6$ is H, L—G is CO$_2$—i-Pr, and |
| 678  W is —CH$_2$—, R$^1$ is Me, R$^2$ is Cl, R$^5$ is CH$_3$, R$^6$ is H, L—G is CO$_2$—t-Bu, and |
| 679  W is —CH$_2$—, R$^1$ is Me, R$^2$ is Cl, R$^5$ is CH$_3$, R$^6$ is H, L—G is SO$_2$Me, and |
| 680  W is —CH$_2$—, R$^1$ is Me, R$^2$ is Br, R$^5$ is CH$_3$, R$^6$ is H, L—G is H, and |
| 681  W is —CH$_2$—, R$^1$ is Me, R$^2$ is Br, R$^5$ is CH$_3$, R$^6$ is H, L—G is C(O)Me, and |
| 682  W is —CH$_2$—, R$^1$ is Me, R$^2$ is Br, R$^5$ is CH$_3$, R$^6$ is H, L—G is C(O)Et, and |
| 683  W is —CH$_2$—, R$^1$ is Me, R$^2$ is Br, R$^5$ is CH$_3$, R$^6$ is H, L—G is C(O)—i-Pr, and |
| 684  W is —CH$_2$—, R$^1$ is Me, R$^2$ is Br, R$^5$ is CH$_3$, R$^6$ is H, L—G is C(O)—t-Bu, and |
| 685  W is —CH$_2$—, R$^1$ is Me, R$^2$ is Br, R$^5$ is CH$_3$, R$^6$ is H, L—G is CO$_2$Me, and |
| 686  W is —CH$_2$—, R$^1$ is Me, R$^2$ is Br, R$^5$ is CH$_3$, R$^6$ is H, L—G is CO$_2$Et, and |
| 687  W is —CH$_2$—, R$^1$ is Me, R$^2$ is Br, R$^5$ is CH$_3$, R$^6$ is H, L—G is CO$_2$—i-Pr, and |
| 688  W is —CH$_2$—, R$^1$ is Me, R$^2$ is Br, R$^5$ is CH$_3$, R$^6$ is H, L—G is CO$_2$—t-Bu, and |
| 689  W is —CH$_2$—, R$^1$ is Me, R$^2$ is Br, R$^5$ is CH$_3$, R$^6$ is H, L—G is SO$_2$Me, and |
| 690  W is —CH$_2$—, R$^1$ is Me, R$^2$ is I, R$^5$ is CH$_3$, R$^6$ is H, L—G is H, and |
| 691  W is —CH$_2$—, R$^1$ is Me, R$^2$ is I, R$^5$ is CH$_3$, R$^6$ is H, L—G is C(O)Me, and |
| 692  W is —CH$_2$—, R$^1$ is Me, R$^2$ is I, R$^5$ is CH$_3$, R$^6$ is H, L—G is C(O)Et, and |
| 693  W is —CH$_2$—, R$^1$ is Me, R$^2$ is I, R$^5$ is CH$_3$, R$^6$ is H, L—G is C(O)—i-Pr, and |
| 694  W is —CH$_2$—, R$^1$ is Me, R$^2$ is I, R$^5$ is CH$_3$, R$^6$ is H, L—G is C(O)—t-Bu, and |
| 695  W is —CH$_2$—, R$^1$ is Me, R$^2$ is I, R$^5$ is CH$_3$, R$^6$ is H, L—G is CO$_2$Me, and |
| 696  W is —CH$_2$—, R$^1$ is Me, R$^2$ is I, R$^5$ is CH$_3$, R$^6$ is H, L—G is CO$_2$Et, and |
| 697  W is —CH$_2$—, R$^1$ is Me, R$^2$ is I, R$^5$ is CH$_3$, R$^6$ is H, L—G is CO$_2$—i-Pr, and |
| 698  W is —CH$_2$—, R$^1$ is Me, R$^2$ is I, R$^5$ is CH$_3$, R$^6$ is H, L—G is CO$_2$—t-Bu, and |
| 699  W is —CH$_2$—, R$^1$ is Me, R$^2$ is I, R$^5$ is CH$_3$, R$^6$ is H, L—G is SO$_2$Me, and |
| 700  W is —CH$_2$—, R$^1$ is Me, R$^2$ is OMe, R$^5$ is CH$_3$, R$^6$ is H, L—G is H, and |
| 701  W is —CH$_2$—, R$^1$ is Me, R$^2$ is OMe, R$^5$ is CH$_3$, R$^6$ is H, L—G is C(O)Me, and |
| 702  W is —CH$_2$—, R$^1$ is Me, R$^2$ is OMe, R$^5$ is CH$_3$, R$^6$ is H, L—G is C(O)Et, and |

-continued

| Table Row Heading |
|---|
| 703 W is —CH$_2$—, R$^1$ is Me, R$^2$ is OMe, R$^5$ is CH$_3$, R$^6$ is H, L—G is C(O)—i-Pr, and |
| 704 W is —CH$_2$—, R$^1$ is Me, R$^2$ is OMe, R$^5$ is CH$_3$, R$^6$ is H, L—G is C(O)—t-Bu, and |
| 705 W is —CH$_2$—, R$^1$ is Me, R$^2$ is OMe, R$^5$ is CH$_3$, R$^6$ is H, L—G is CO$_2$Me, and |
| 706 W is —CH$_2$—, R$^1$ is Me, R$^2$ is OMe, R$^5$ is CH$_3$, R$^6$ is H, L—G is CO$_2$Et, and |
| 707 W is —CH$_2$—, R$^1$ is Me, R$^2$ is OMe, R$^5$ is CH$_3$, R$^6$ is H, L—G is CO$_2$—i-Pr, and |
| 708 W is —CH$_2$—, R$^1$ is Me, R$^2$ is OMe, R$^5$ is CH$_3$, R$^6$ is H, L—G is CO$_2$—t-Bu, and |
| 709 W is —CH$_2$—, R$^1$ is Me, R$^2$ is OMe, R$^5$ is CH$_3$, R$^6$ is H, L—G is SO$_2$Me, and |
| 710 W is —CH$_2$—, R$^1$ is Me, R$^2$ is CN, R$^5$ is CH$_3$, R$^6$ is H, L—G is H, and |
| 711 W is —CH$_2$—, R$^1$ is Me, R$^2$ is CN, R$^5$ is CH$_3$, R$^6$ is H, L—G is C(O)Me, and |
| 712 W is —CH$_2$—, R$^1$ is Me, R$^2$ is CN, R$^5$ is CH$_3$, R$^6$ is H, L—G is C(O)Et, and |
| 713 W is —CH$_2$—, R$^1$ is Me, R$^2$ is CN, R$^5$ is CH$_3$, R$^6$ is H, L—G is C(O)—i-Pr, and |
| 714 W is —CH$_2$—, R$^1$ is Me, R$^2$ is CN, R$^5$ is CH$_3$, R$^6$ is H, L—G is C(O)—t-Bu, and |
| 715 W is —CH$_2$—, R$^1$ is Me, R$^2$ is CN, R$^5$ is CH$_3$, R$^6$ is H, L—G is CO$_2$Me, and |
| 716 W is —CH$_2$—, R$^1$ is Me, R$^2$ is CN, R$^5$ is CH$_3$, R$^6$ is H, L—G is CO$_2$Et, and |
| 717 W is —CH$_2$—, R$^1$ is Me, R$^2$ is CN, R$^5$ is CH$_3$, R$^6$ is H, L—G is CO$_2$—i-Pr, and |
| 718 W is —CH$_2$—, R$^1$ is Me, R$^2$ is CN, R$^5$ is CH$_3$, R$^6$ is H, L—G is CO$_2$—t-Bu, and |
| 719 W is —CH$_2$—, R$^1$ is Me, R$^2$ is CN, R$^5$ is CH$_3$, R$^6$ is H, L—G is SO$_2$Me, and |
| 720 W is —CH$_2$—, R$^1$ is Et, R$^2$ is Me, R$^5$ is CH$_3$, R$^6$ is H, L—G is H, and |
| 721 W is —CH$_2$—, R$^1$ is Et, R$^2$ is Me, R$^5$ is CH$_3$, R$^6$ is H, L—G is C(O)Me, and |
| 722 W is —CH$_2$—, R$^1$ is Et, R$^2$ is Me, R$^5$ is CH$_3$, R$^6$ is H, L—G is C(O)Et, and |
| 723 W is —CH$_2$—, R$^1$ is Et, R$^2$ is Me, R$^5$ is CH$_3$, R$^6$ is H, L—G is C(O)—i-Pr, and |
| 724 W is —CH$_2$—, R$^1$ is Et, R$^2$ is Me, R$^5$ is CH$_3$, R$^6$ is H, L—G is C(O)—t-Bu, and |
| 725 W is —CH$_2$—, R$^1$ is Et, R$^2$ is Me, R$^5$ is CH$_3$, R$^6$ is H, L—G is CO$_2$Me, and |
| 726 W is —CH$_2$—, R$^1$ is Et, R$^2$ is Me, R$^5$ is CH$_3$, R$^6$ is H, L—G is CO$_2$Et, and |
| 727 W is —CH$_2$—, R$^1$ is Et, R$^2$ is Me, R$^5$ is CH$_3$, R$^6$ is H, L—G is CO$_2$—i-Pr, and |
| 728 W is —CH$_2$—, R$^1$ is Et, R$^2$ is Me, R$^5$ is CH$_3$, R$^6$ is H, L—G is CO$_2$—t-Bu, and |
| 729 W is —CH$_2$—, R$^1$ is Et, R$^2$ is Me, R$^5$ is CH$_3$, R$^6$ is H, L—G is SO$_2$Me, and |
| 730 W is —CH$_2$—, R$^1$ is Et, R$^2$ is H, R$^5$ is CH$_3$, R$^6$ is H, L—G is H, and |
| 731 W is —CH$_2$—, R$^1$ is Et, R$^2$ is H, R$^5$ is CH$_3$, R$^6$ is H, L—G is C(O)Me, and |
| 732 W is —CH$_2$—, R$^1$ is Et, R$^2$ is H, R$^5$ is CH$_3$, R$^6$ is H, L—G is C(O)Et, and |
| 733 W is —CH$_2$—, R$^1$ is Et, R$^2$ is H, R$^5$ is CH$_3$, R$^6$ is H, L—G is C(O)—i-Pr, and |
| 734 W is —CH$_2$—, R$^1$ is Et, R$^2$ is H, R$^5$ is CH$_3$, R$^6$ is H, L—G is C(O)—t-Bu, and |
| 735 W is —CH$_2$—, R$^1$ is Et, R$^2$ is H, R$^5$ is CH$_3$, R$^6$ is H, L—G is CO$_2$Me, and |
| 736 W is —CH$_2$—, R$^1$ is Et, R$^2$ is H, R$^5$ is CH$_3$, R$^6$ is H, L—G is CO$_2$Et, and |
| 737 W is —CH$_2$—, R$^1$ is Et, R$^2$ is H, R$^5$ is CH$_3$, R$^6$ is H, L—G is CO$_2$—i-Pr, and |
| 738 W is —CH$_2$—, R$^1$ is Et, R$^2$ is H, R$^5$ is CH$_3$, R$^6$ is H, L—G is CO$_2$—t-Bu, and |
| 739 W is —CH$_2$—, R$^1$ is Et, R$^2$ is H, R$^5$ is CH$_3$, R$^6$ is H, L—G is SO$_2$Me, and |
| 740 W is —CH$_2$—, R$^1$ is Et, R$^2$ is CF$_3$, R$^5$ is CH$_3$, R$^6$ is H, L—G is H, and |
| 741 W is —CH$_2$—, R$^1$ is Et, R$^2$ is CF$_3$, R$^5$ is CH$_3$, R$^6$ is H, L—G is C(O)Me, and |
| 742 W is —CH$_2$—, R$^1$ is Et, R$^2$ is CF$_3$, R$^5$ is CH$_3$, R$^6$ is H, L—G is C(O)Et, and |
| 743 W is —CH$_2$—, R$^1$ is Et, R$^2$ is CF$_3$, R$^5$ is CH$_3$, R$^6$ is H, L—G is C(O)—i-Pr, and |
| 744 W is —CH$_2$—, R$^1$ is Et, R$^2$ is CF$_3$, R$^5$ is CH$_3$, R$^6$ is H, L—G is C(O)—t-Bu, and |
| 745 W is —CH$_2$—, R$^1$ is Et, R$^2$ is CF$_3$, R$^5$ is CH$_3$, R$^6$ is H, L—G is CO$_2$Me, and |
| 746 W is —CH$_2$—, R$^1$ is Et, R$^2$ is CF$_3$, R$^5$ is CH$_3$, R$^6$ is H, L—G is CO$_2$Et, and |
| 747 W is —CH$_2$—, R$^1$ is Et, R$^2$ is CF$_3$, R$^5$ is CH$_3$, R$^6$ is H, L—G is CO$_2$—i-Pr, and |
| 748 W is —CH$_2$—, R$^1$ is Et, R$^2$ is CF$_3$, R$^5$ is CH$_3$, R$^6$ is H, L—G is CO$_2$—t-Bu, and |
| 749 W is —CH$_2$—, R$^1$ is Et, R$^2$ is CF$_3$, R$^5$ is CH$_3$, R$^6$ is H, L—G is SO$_2$Me, and |
| 750 W is —CH$_2$—, R$^1$ is Et, R$^2$ is Cl, R$^5$ is CH$_3$, R$^6$ is H, L—G is H, and |
| 751 W is —CH$_2$—, R$^1$ is Et, R$^2$ is Cl, R$^5$ is CH$_3$, R$^6$ is H, L—G is C(O)Me, and |
| 752 W is —CH$_2$—, R$^1$ is Et, R$^2$ is Cl, R5 is CH$_3$, R$^6$ is H, L—G is C(O)Et, and |
| 753 W is —CH$_2$—, R$^1$ is Et, R$^2$ is Cl, R$^5$ is CH$_3$, R$^6$ is H, L—G is C(O)—i-Pr, and |
| 754 W is —CH$_2$—, R$^1$ is Et, R$^2$ is Cl, R$^5$ is CH$_3$, R$^6$ is H, L—G is C(O)—t-Bu, and |
| 755 W is —CH$_2$—, R$^1$ is Et, R$^2$ is Cl, R$^5$ is CH$_3$, R$^6$ is H, L—G is CO$_2$Me, and |
| 756 W is —CH$_2$—, R$^1$ is Et, R$^2$ is Cl, R$^5$ is CH$_3$, R$^6$ is H, L—G is CO$_2$Et, and |
| 757 W is —CH$_2$—, R$^1$ is Et, R$^2$ is Cl, R$^5$ is CH$_3$, R$^6$ is H, L—G is CO$_2$—i-Pr, and |
| 758 W is —CH$_2$—, R$^1$ is Et, R$^2$ is Cl, R$^5$ is CH$_3$, R$^6$ is H, L—G is CO$_2$—t-Bu, and |
| 759 W is —CH$_2$—, R$^1$ is Et, R$^2$ is Cl, R$^5$ is CH$_3$, R$^6$ is H, L—G is SO$_2$Me, and |
| 760 W is —CH$_2$—, R$^1$ is Et, R$^2$ is Br, R$^5$ is CH$_3$, R$^6$ is H, L—G is H, and |
| 761 W is —CH$_2$—, R$^1$ is Et, R$^2$ is Br, R$^5$ is CH$_3$, R$^6$ is H, L—G is C(O)Me, and |
| 762 W is —CH$_2$—, R$^1$ is Et, R$^2$ is Br, R$^5$ is CH$_3$, R$^6$ is H, L—G is C(O)Et, and |
| 763 W is —CH$_2$—, R$^1$ is Et, R$^2$ is Br, R$^5$ is CH$_3$, R$^6$ is H, L—G is C(O)—i-Pr, and |
| 764 W is —CH$_2$—, R$^1$ is Et, R$^2$ is Br, R$^5$ is CH$_3$, R$^6$ is H, L—G is C(O)—t-Bu, and |
| 765 W is —CH$_2$—, R$^1$ is Et, R$^2$ is Br, R$^5$ is CH$_3$, R$^6$ is H, L—G is CO$_2$Me, and |
| 766 W is —CH$_2$—, R$^1$ is Et, R$^2$ is Br, R$^5$ is CH$_3$, R$^6$ is H, L—G is CO$_2$Et, and |
| 767 W is —CH$_2$—, R$^1$ is Et, R$^2$ is Br, R$^5$ is CH$_3$, R$^6$ is H, L—G is CO$_2$—i-Pr, and |
| 768 W is —CH$_2$—, R$^1$ is Et, R$^2$ is Br, R$^5$ is CH$_3$, R$^6$ is H, L—G is CO$_2$—t-Bu, and |
| 769 W is —CH$_2$—, R$^1$ is Et, R$^2$ is Br, R$^5$ is CH$_3$, R$^6$ is H, L—G is SO$_2$Me, and |
| 770 W is —CH$_2$—, R$^1$ is Et, R$^2$ is I, R$^5$ is CH$_3$, R$^6$ is H, L—G is H, and |
| 771 W is —CH$_2$—, R$^1$ is Et, R$^2$ is I, R$^5$ is CH$_3$, R$^6$ is H, L—G is C(O)Me, and |
| 772 W is —CH$_2$—, R$^1$ is Et, R$^2$ is I, R$^5$ is CH$_3$, R$^6$ is H, L—G is C(O)Et, and |
| 773 W is —CH$_2$—, R$^1$ is Et, R$^2$ is I, R$^5$ is CH$_3$, R$^6$ is H, L—G is C(O)—i-Pr, and |
| 774 W is —CH$_2$—, R$^1$ is Et, R$^2$ is I, R$^5$ is CH$_3$, R$^6$ is H, L—G is C(O)—t-Bu, and |
| 775 W is —CH$_2$—, R$^1$ is Et, R$^2$ is I, R$^5$ is CH$_3$, R$^6$ is H, L—G is CO$_2$Me, and |
| 776 W is —CH$_2$—, R$^1$ is Et, R$^2$ is I, R$^5$ is CH$_3$, R$^6$ is H, L—G is CO$_2$Et, and |
| 777 W is —CH$_2$—, R$^1$ is Et, R$^2$ is I, R$^5$ is CH$_3$, R$^6$ is H, L—G is CO$_2$—i-Pr, and |
| 778 W is —CH$_2$—, R$^1$ is Et, R$^2$ is I, R$^5$ is CH$_3$, R$^6$ is H, L—G is CO$_2$—t-Bu, and |
| 779 W is —CH$_2$—, R$^1$ is Et, R$^2$ is I, R$^5$ is CH$_3$, R$^6$ is H, L—G is SO$_2$Me, and |

-continued

| Table Row Heading |
|---|
| 780 W is —CH$_2$—, R$^1$ is Et, R$^2$ is OMe, R$^5$ is CH$_3$, R$^6$ is H, L—G is H, and |
| 781 W is —CH$_2$—, R$^1$ is Et, R$^2$ is OMe, R$^5$ is CH$_3$, R$^6$ is H, L—G is C(O)Me, and |
| 782 W is —CH$_2$—, R$^1$ is Et, R$^2$ is OMe, R$^5$ is CH$_3$, R$^6$ is H, L—G is C(O)Et, and |
| 783 W is —CH$_2$—, R$^1$ is Et, R$^2$ is OMe, R$^5$ is CH$_3$, R$^6$ is H, L—G is C(O)—i-Pr, and |
| 784 W is —CH$_2$—, R$^1$ is Et, R$^2$ is OMe, R$^5$ is CH$_3$, R$^6$ is H, L—G is C(O)—t-Bu, and |
| 785 W is —CH$_2$—, R$^1$ is Et, R$^2$ is OMe, R$^5$ is CH$_3$, R$^6$ is H, L—G is CO$_2$Me, and |
| 786 W is —CH$_2$—, R$^1$ is Et, R$^2$ is OMe, R$^5$ is CH$_3$, R$^6$ is H, L—G is CO$_2$Et, and |
| 787 W is —CH$_2$—, R$^1$ is Et, R$^2$ is OMe, R$^5$ is CH$_3$, R$^6$ is H, L—G is CO$_2$—i-Pr, and |
| 788 W is —CH$_2$—, R$^1$ is Et, R$^2$ is OMe, R$^5$ is CH$_3$, R$^6$ is H, L—G is CO$_2$—t-Bu, and |
| 789 W is —CH$_2$—, R$^1$ is Et, R$^2$ is OMe, R$^5$ is CH$_3$, R$^6$ is H, L—G is SO$_2$Me, and |
| 790 W is —CH$_2$—, R$^1$ is Et, R$^2$ is CN, R$^5$ is CH$_3$, R$^6$ is H, L—G is H, and |
| 791 W is —CH$_2$—, R$^1$ is Et, R$^2$ is CN, R$^5$ is CH$_3$, R$^6$ is H, L—G is C(O)Me, and |
| 792 W is —CH$_2$—, R$^1$ is Et, R$^2$ is CN, R$^5$ is CH$_3$, R$^6$ is H, L—G is C(O)Et, and |
| 793 W is —CH$_2$—, R$^1$ is Et, R$^2$ is CN, R$^5$ is CH$_3$, R$^6$ is H, L—G is C(O)—i-Pr, and |
| 794 W is —CH$_2$—, R$^1$ is Et, R$^2$ is CN, R$^5$ is CH$_3$, R$^6$ is H, L—G is C(O)—t-Bu, and |
| 795 W is —CH$_2$—, R$^1$ is Et, R$^2$ is CN, R$^5$ is CH$_3$, R$^6$ is H, L—G is CO$_2$Me, and |
| 796 W is —CH$_2$—, R$^1$ is Et, R$^2$ is CN, R$^5$ is CH$_3$, R$^6$ is H, L—G is CO$_2$Et, and |
| 797 W is —CH$_2$—, R$^1$ is Et, R$^2$ is CN, R$^5$ is CH$_3$, R$^6$ is H, L—G is CO$_2$—i-Pr, and |
| 798 W is —CH$_2$—, R$^1$ is Et, R$^2$ is CN, R$^5$ is CH$_3$, R$^6$ is H, L—G is CO$_2$—t-Bu, and |
| 799 W is —CH$_2$—, R$^1$ is Et, R$^2$ is CN, R$^5$ is CH$_3$, R$^6$ is H, L—G is SO$_2$Me, and |
| 800 W is —CH$_2$—, R$^1$ is Me, R$^2$ is Me, R$^5$ is CH$_3$, R$^6$ CH$_3$, L—G is H, and |
| 801 W is —CH$_2$—, R$^1$ is Me, R$^2$ is Me, R$^5$ is CH$_3$, R$^6$ CH$_3$, L—G is C(O)Me, and |
| 802 W is —CH$_2$—, R$^1$ is Me, R$^2$ is Me, R$^5$ is CH$_3$, R$^6$ CH$_3$, L—G is C(O)Et, and |
| 803 W is —CH$_2$—, R$^1$ is Me, R$^2$ is Me, R$^5$ is CH$_3$, R$^6$ CH$_3$, L—G is C(O)—i-Pr, and |
| 804 W is —CH$_2$—, R$^1$ is Me, R$^2$ is Me, R$^5$ is CH$_3$, R$^6$ CH$_3$, L—G is C(O)—t-Bu, and |
| 805 W is —CH$_2$—, R$^1$ is Me, R$^2$ is Me, R$^5$ is CH$_3$, R$^6$ CH$_3$, L—G is CO$_2$Me, and |
| 806 W is —CH$_2$—, R$^1$ is Me, R$^2$ is Me, R$^5$ is CH$_3$, R$^6$ CH$_3$, L—G is CO$_2$Et, and |
| 807 W is —CH$_2$—, R$^1$ is Me, R$^2$ is Me, R$^5$ is CH$_3$, R$^6$ CH$_3$, L—G is CO$_2$—i-Pr, and |
| 808 W is —CH$_2$—, R$^1$ is Me, R$^2$ is Me, R$^5$ is CH$_3$, R$^6$ CH$_3$, L—G is CO$_2$—t-Bu, and |
| 809 W is —CH$_2$—, R$^1$ is Me, R$^2$ is Me, R$^5$ is CH$_3$, R$^6$ CH$_3$, L—G is SO$_2$Me, and |
| 810 W is —CH$_2$—, R$^1$ is Me, R$^2$ is H, R$^5$ is CH$_3$, R$^6$ CH$_3$, L—G is H, and |
| 811 W is —CH$_2$—, R$^1$ is Me, R$^2$ is H, R$^5$ is CH$_3$, R$^6$ CH$_3$, L—G is C(O)Me, and |
| 812 W is —CH$_2$—, R$^1$ is Me, R$^2$ is H, R$^5$ is CH$_3$, R$^6$ CH$_3$, L—G is C(O)Et, and |
| 813 W is —CH$_2$—, R$^1$ is Me, R$^2$ is H, R$^5$ is CH$_3$, R$^6$ CH$_3$, L—G is C(O)—i-Pr, and |
| 814 W is —CH$_2$—, R$^1$ is Me, R$^2$ is H, R$^5$ is CH$_3$, R$^6$ CH$_3$, L—G is C(O)—t-Bu, and |
| 815 W is —CH$_2$—, R$^1$ is Me, R$^2$ is H, R$^5$ is CH$_3$, R$^6$ CH$_3$, L—G is CO$_2$Me, and |
| 816 W is —CH$_2$—, R$^1$ is Me, R$^2$ is H, R$^5$ is CH$_3$, R$^6$ CH$_3$, L—G is CO$_2$Et, and |
| 817 W is —CH$_2$—, R$^1$ is Me, R$^2$ is H, R$^5$ is CH$_3$, R$^6$ CH$_3$, L—G is CO$_2$—i-Pr, and |
| 818 W is —CH$_2$—, R$^1$ is Me, R$^2$ is H, R$^5$ is CH$_3$, R$^6$ CH$_3$, L—G is CO$_2$—t-Bu, and |
| 819 W is —CH$_2$—, R$^1$ is Me, R$^2$ is H, R$^5$ is CH$_3$, R$^6$ CH$_3$, L—G is SO$_2$Me, and |
| 820 W is —CH$_2$—, R$^1$ is Me, R$^2$ is CF$_3$, R$^5$ is CH$_3$, R$^6$ CH$_3$, L—G is H, and |
| 821 W is —CH$_2$—, R$^1$ is Me, R$^2$ is CF$_3$, R$^5$ is CH$_3$, R$^6$ CH$_3$, L—G is C(O)Me, and |
| 822 W is —CH$_2$—, R$^1$ is Me, R$^2$ is CF$_3$, R$^5$ is CH$_3$, R$^6$ CH$_3$, L—G is C(O)Et, and |
| 823 W is —CH$_2$—, R$^1$ is Me, R$^2$ is CF$_3$, R$^5$ is CH$_3$, R$^6$ CH$_3$, L—G is C(O)—i-Pr, and |
| 824 W is —CH$_2$—, R$^1$ is Me, R$^2$ is CF$_3$, R$^5$ is CH$_3$, R$^6$ CH$_3$, L—G is C(O)—t-Bu, and |
| 825 W is —CH$_2$—, R$^1$ is Me, R$^2$ is CF$_3$, R$^5$ is CH$_3$, R$^6$ CH$_3$, L—G is CO$_2$Me, and |
| 826 W is —CH$_2$—, R$^1$ is Me, R$^2$ is CF$_3$, R$^5$ is CH$_3$, R$^6$ CH$_3$, L—G is CO$_2$Et, and |
| 827 W is —CH$_2$—, R$^1$ is Me, R$^2$ is CF$_3$, R$^5$ is CH$_3$, R$^6$ CH$_3$, L—G is CO$_2$—i-Pr, and |
| 828 W is —CH$_2$—, R$^1$ is Me, R$^2$ is CF$_3$, R$^5$ is CH$_3$, R$^6$ CH$_3$, L—G is CO$_2$—t-Bu, and |
| 829 W is —CH$_2$—, R$^1$ is Me, R$^2$ is CF$_3$, R$^5$ is CH$_3$, R$^6$ CH$_3$, L—G is SO$_2$Me, and |
| 830 W is —CH$_2$—, R$^1$ is Me, R$^2$ is Cl, R$^5$ is CH$_3$, R$^6$ CH$_3$, L—G is H, and |
| 831 W is —CH$_2$—, R$^1$ is Me, R$^2$ is Cl, R$^5$ is CH$_3$, R$^6$ CH$_3$, L—G is C(O)Me, and |
| 832 W is —CH$_2$—, R$^1$ is Me, R$^2$ is Cl, R$^5$ is CH$_3$, R$^6$ CH$_3$, L—G is C(O)Et, and |
| 833 W is —CH$_2$—, R$^1$ is Me, R$^2$ is Cl, R$^5$ is CH$_3$, R$^6$ CH$_3$, L—G is C(O)—i-Pr, and |
| 834 W is —CH$_2$—, R$^1$ is Me, R$^2$ is Cl, R$^5$ is CH$_3$, R$^6$ CH$_3$, L—G is C(O)—t-Bu, and |
| 835 W is —CH$_2$—, R$^1$ is Me, R$^2$ is Cl, R$^5$ is CH$_3$, R$^6$ CH$_3$, L—G is CO$_2$Me, and |
| 836 W is —CH$_2$—, R$^1$ is Me, R$^2$ is Cl, R$^5$ is CH$_3$, R$^6$ CH$_3$, L—G is CO$_2$Et, and |
| 837 W is —CH$_2$—, R$^1$ is Me, R$^2$ is Cl, R$^5$ is CH$_3$, R$^6$ CH$_3$, L—G is CO$_2$—i-Pr, and |
| 838 W is —CH$_2$—, R$^1$ is Me, R$^2$ is Cl, R$^5$ is CH$_3$, R$^6$ CH$_3$, L—G is CO$_2$—t-Bu, and |
| 839 W is —CH$_2$—, R$^1$ is Me, R$^2$ is Cl, R$^5$ is CH$_3$, R$^6$ CH$_3$, L—G is SO$_2$Me, and |
| 840 W is —CH$_2$—, R$^1$ is Me, R$^2$ is Br, R$^5$ is CH$_3$, R$^6$ CH$_3$, L—G is H, and |
| 841 W is —CH$_2$—, R$^1$ is Me, R$^2$ is Br, R$^5$ is CH$_3$, R$^6$ CH$_3$, L—G is C(O)Me, and |
| 842 W is —CH$_2$—, R$^1$ is Me, R$^2$ is Br, R$^5$ is CH$_3$, R$^6$ CH$_3$, L—G is C(O)Et, and |
| 843 W is —CH$_2$—, R$^1$ is Me, R$^2$ is Br, R$^5$ is CH$_3$, R$^6$ CH$_3$, L—G is C(O)—i-Pr, and |
| 844 W is —CH$_2$—, R$^1$ is Me, R$^2$ is Br, R$^5$ is CH$_3$, R$^6$ CH$_3$, L—G is C(O)—t-Bu, and |
| 845 W is —CH$_2$—, R$^1$ is Me, R$^2$ is Br, R$^5$ is CH$_3$, R$^6$ CH$_3$, L—G is CO$_2$Me, and |
| 846 W is —CH$_2$—, R$^1$ is Me, R$^2$ is Br, R$^5$ is CH$_3$, R$^6$ CH$_3$, L—G is CO$_2$Et, and |
| 847 W is —CH$_2$—, R$^1$ is Me, R$^2$ is Br, R$^5$ is CH$_3$, R$^6$ CH$_3$, L—G is CO$_2$—i-Pr, and |
| 848 W is —CH$_2$—, R$^1$ is Me, R$^2$ is Br, R$^5$ is CH$_3$, R$^6$ CH$_3$, L—G is CO$_2$—t-Bu, and |
| 849 W is —CH$_2$—, R$^1$ is Me, R$^2$ is Br, R$^5$ is CH$_3$, R$^6$ CH$_3$, L—G is SO$_2$Me, and |
| 850 W is —CH$_2$—, R$^1$ is Me, R$^2$ is I, R$^5$ is CH$_3$, R$^6$ CH$_3$, L—G is H, and |
| 851 W is —CH$_2$—, R$^1$ is Me, R$^2$ is I, R$^5$ is CH$_3$, R$^6$ CH$_3$, L—G is C(O)Me, and |
| 852 W is —CH$_2$—, R$^1$ is Me, R$^2$ is I, R$^5$ is CH$_3$, R$^6$ CH$_3$, L—G is C(O)Et, and |
| 853 W is —CH$_2$—, R$^1$ is Me, R$^2$ is I, R$^5$ is CH$_3$, R$^6$ CH$_3$, L—G is C(O)—i-Pr, and |
| 854 W is —CH$_2$—, R$^1$ is Me, R$^2$ is I, R$^5$ is CH$_3$, R$^6$ CH$_3$, L—G is C(O)—t-Bu, and |
| 855 W is —CH$_2$—, R$^1$ is Me, R$^2$ is I, R$^5$ is CH$_3$, R$^6$ CH$_3$, L—G is CO$_2$Me, and |
| 856 W is —CH$_2$—, R$^1$ is Me, R$^2$ is I, R$^5$ is CH$_3$, R$^6$ CH$_3$, L—G is CO$_2$Et, and |

-continued

| Table Row Heading |
|---|
| 857 W is —CH$_2$—, R$^1$ is Me, R$^2$ is I, R$^5$ is CH$_3$, R$^6$ CH$_3$, L—G is CO$_2$—i-Pr, and |
| 858 W is —CH$_2$—, R$^1$ is Me, R$^2$ is I, R$^5$ is CH$_3$, R$^6$ CH$_3$, L—G is CO$_2$—t-Bu, and |
| 859 W is —CH$_2$—, R$^1$ is Me, R$^2$ is I, R$^5$ is CH$_3$, R$^6$ CH$_3$, L—G is SO$_2$Me, and |
| 860 W is —CH$_2$—, R$^1$ is Me, R$^2$ is OMe, R$^5$ is CH$_3$, R$^6$ CH$_3$, L—G is H, and |
| 861 W is —CH$_2$—, R$^1$ is Me, R$^2$ is OMe, R$^5$ is CH$_3$, R$^6$ CH$_3$, L—G is C(O)Me, and |
| 862 W is —CH$_2$—, R$^1$ is Me, R$^2$ is OMe, R$^5$ is CH$_3$, R$^6$ CH$_3$, L—G is C(O)Et, and |
| 863 W is —CH$_2$—, R$^1$ is Me, R$^2$ is OMe, R$^5$ is CH$_3$, R$^6$ CH$_3$, L—G is C(O)—i-Pr, and |
| 864 W is —CH$_2$—, R$^1$ is Me, R$^2$ is OMe, R$^5$ is CH$_3$, R$^6$ CH$_3$, L—G is C(O)—t-Bu, and |
| 865 W is —CH$_2$—, R$^1$ is Me, R$^2$ is OMe, R$^5$ is CH$_3$, R$^6$ CH$_3$, L—G is CO$_2$Me, and |
| 866 W is —CH$_2$—, R$^1$ is Me, R$^2$ is OMe, R$^5$ is CH$_3$, R$^6$ CH$_3$, L—G is CO$_2$Et, and |
| 867 W is —CH$_2$—, R$^1$ is Me, R$^2$ is OMe, R$^5$ is CH$_3$, R$^6$ CH$_3$, L—G is CO$_2$—i-Pr, and |
| 868 W is —CH$_2$—, R$^1$ is Me, R$^2$ is OMe, R$^5$ is CH$_3$, R$^6$ CH$_3$, L—G is CO$_2$—t-Bu, and |
| 869 W is —CH$_2$—, R$^1$ is Me, R$^2$ is OMe, R$^5$ is CH$_3$, R$^6$ CH$_3$, L—G is SO$_2$Me, and |
| 870 W is —CH$_2$—, R$^1$ is Me, R$^2$ is CN, R$^5$ is CH$_3$, R$^6$ CH$_3$, L—G is H, and |
| 871 W is —CH$_2$—, R$^1$ is Me, R$^2$ is CN, R$^5$ is CH$_3$, R$^6$ CH$_3$, L—G is C(O)Me, and |
| 872 W is —CH$_2$—, R$^1$ is Me, R$^2$ is CN, R$^5$ is CH$_3$, R$^6$ CH$_3$, L—G is C(O)Et, and |
| 873 W is —CH$_2$—, R$^1$ is Me, R$^2$ is CN, R$^5$ is CH$_3$, R$^6$ CH$_3$, L—G is C(O)—i-Pr, and |
| 874 W is —CH$_2$—, R$^1$ is Me, R$^2$ is CN, R$^5$ is CH$_3$, R$^6$ CH$_3$, L—G is C(O)—t-Bu, and |
| 875 W is —CH$_2$—, R$^1$ is Me, R$^2$ is CN, R$^5$ is CH$_3$, R$^6$ CH$_3$, L—G is CO$_2$Me, and |
| 876 W is —CH$_2$—, R$^1$ is Me, R$^2$ is CN, R$^5$ is CH$_3$, R$^6$ CH$_3$, L—G is CO$_2$Et, and |
| 877 W is —CH$_2$—, R$^1$ is Me, R$^2$ is CN, R$^5$ is CH$_3$, R$^6$ CH$_3$, L—G is CO$_2$—i-Pr, and |
| 878 W is —CH$_2$—, R$^1$ is Me, R$^2$ is CN, R$^5$ is CH$_3$, R$^6$ CH$_3$, L—G is CO$_2$—t-Bu, and |
| 879 W is —CH$_2$—, R$^1$ is Me, R$^2$ is CN, R$^5$ is CH$_3$, R$^6$ CH$_3$, L—G is SO$_2$Me, and |
| 880 W is —CH$_2$—, R$^1$ is Et, R$^2$ is Me, R$^5$ is CH$_3$, R$^6$ CH$_3$, L—G is H, and |
| 881 W is —CH$_2$—, R$^1$ is Et, R$^2$ is Me, R$^5$ is CH$_3$, R$^6$ CH$_3$, L—G is C(O)Me, and |
| 882 W is —CH$_2$—, R$^1$ is Et, R$^2$ is Me, R$^5$ is CH$_3$, R$^6$ CH$_3$, L—G is C(O)Et, and |
| 883 W is —CH$_2$—, R$^1$ is Et, R$^2$ is Me, R$^5$ is CH$_3$, R$^6$ CH$_3$, L—G is C(O)—i-Pr, and |
| 884 W is —CH$_2$—, R$^1$ is Et, R$^2$ is Me, R$^5$ is CH$_3$, R$^6$ CH$_3$, L—G is C(O)—t-Bu, and |
| 885 W is —CH$_2$—, R$^1$ is Et, R$^2$ is Me, R$^5$ is CH$_3$, R$^6$ CH$_3$, L—G is CO$_2$Me, and |
| 886 W is —CH$_2$—, R$^1$ is Et, R$^2$ is Me, R$^5$ is CH$_3$, R$^6$ CH$_3$, L—G is CO$_2$Et, and |
| 887 W is —CH$_2$—, R$^1$ is Et, R$^2$ is Me, R$^5$ is CH$_3$, R$^6$ CH$_3$, L—G is CO$_2$—i-Pr, and |
| 888 W is —CH$_2$—, R$^1$ is Et, R$^2$ is Me, R$^5$ is CH$_3$, R$^6$ CH$_3$, L—G is CO$_2$—t-Bu, and |
| 889 W is —CH$_2$—, R$^1$ is Et, R$^2$ is Me, R$^5$ is CH$_3$, R$^6$ CH$_3$, L—G is SO$_2$Me, and |
| 890 W is —CH$_2$—, R$^1$ is Et, R$^2$ is H, R$^5$ is CH$_3$, R$^6$ CH$_3$, L—G is H, and |
| 891 W is —CH$_2$—, R$^1$ is Et, R$^2$ is H, R$^5$ is CH$_3$, R$^6$ CH$_3$, L—G is C(O)Me, and |
| 892 W is —CH$_2$—, R$^1$ is Et, R$^2$ is H, R$^5$ is CH$_3$, R$^6$ CH$_3$, L—G is C(O)Et, and |
| 893 W is —CH$_2$—, R$^1$ is Et, R$^2$ is H, R$^5$ is CH$_3$, R$^6$ CH$_3$, L—G is C(O)—i-Pr, and |
| 894 W is —CH$_2$—, R$^1$ is Et, R$^2$ is H, R$^5$ is CH$_3$, R$^6$ CH$_3$, L—G is C(O)—t-Bu, and |
| 895 W is —CH$_2$—, R$^1$ is Et, R$^2$ is H, R$^5$ is CH$_3$, R$^6$ CH$_3$, L—G is CO$_2$Me, and |
| 896 W is —CH$_2$—, R$^1$ is Et, R$^2$ is H, R$^5$ is CH$_3$, R$^6$ CH$_3$, L—G is CO$_2$Et, and |
| 897 W is —CH$_2$—, R$^1$ is Et, R$^2$ is H, R$^5$ is CH$_3$, R$^6$ CH$_3$, L—G is CO$_2$—i-Pr, and |
| 898 W is —CH$_2$—, R$^1$ is Et, R$^2$ is H, R$^5$ is CH$_3$, R$^6$ CH$_3$, L—G is CO$_2$—t-Bu, and |
| 899 W is —CH$_2$—, R$^1$ is Et, R$^2$ is H, R$^5$ is CH$_3$, R$^6$ CH$_3$, L—G is SO$_2$Me, and |
| 900 W is —CH$_2$—, R$^1$ is Et, R$^2$ is CF$_3$, R$^5$ is CH$_3$, R$^6$ CH$_3$, L—G is H, and |
| 901 W is —CH$_2$—, R$^1$ is Et, R$^2$ is CF$_3$, R$^5$ is CH$_3$, R$^6$ CH$_3$, L—G is C(O)Me, and |
| 902 W is —CH$_2$—, R$^1$ is Et, R$^2$ is CF$_3$, R$^5$ is CH$_3$, R$^6$ CH$_3$, L—G is C(O)Et, and |
| 903 W is —CH$_2$—, R$^1$ is Et, R$^2$ is CF$_3$, R$^5$ is CH$_3$, R$^6$ CH$_3$, L—G is C(O)—i-Pr, and |
| 904 W is —CH$_2$—, R$^1$ is Et, R$^2$ is CF$_3$, R$^5$ is CH$_3$, R$^6$ CH$_3$, L—G is C(O)—t-Bu, and |
| 905 W is —CH$_2$—, R$^1$ is Et, R$^2$ is CF$_3$, R$^5$ is CH$_3$, R$^6$ CH$_3$, L—G is CO$_2$Me, and |
| 906 W is —CH$_2$—, R$^1$ is Et, R$^2$ is CF$_3$, R$^5$ is CH$_3$, R$^6$ CH$_3$, L—G is CO$_2$Et, and |
| 907 W is —CH$_2$—, R$^1$ is Et, R$^2$ is CF$_3$, R$^5$ is CH$_3$, R$^6$ CH$_3$, L—G is CO$_2$—i-Pr, and |
| 908 W is —CH$_2$—, R$^1$ is Et, R$^2$ is CF$_3$, R$^5$ is CH$_3$, R$^6$ CH$_3$, L—G is CO$_2$—t-Bu, and |
| 909 W is —CH$_2$—, R$^1$ is Et, R$^2$ is CF$_3$, R$^5$ is CH$_3$, R$^6$ CH$_3$, L—G is SO$_2$Me, and |
| 910 W is —CH$_2$—, R$^1$ is Et, R$^2$ is Cl, R$^5$ is CH$_3$, R$^6$ CH$_3$, L—G is H, and |
| 911 W is —CH$_2$—, R$^1$ is Et, R$^2$ is Cl, R$^5$ is CH$_3$, R$^6$ CH$_3$, L—G is C(O)Me, and |
| 912 W is —CH$_2$—, R$^1$ is Et, R$^2$ is Cl, R$^5$ is CH$_3$, R$^6$ CH$_3$, L—G is C(O)Et, and |
| 913 W is —CH$_2$—, R$^1$ is Et, R$^2$ is Cl, R$^5$ is CH$_3$, R$^6$ CH$_3$, L—G is C(O)—i-Pr, and |
| 914 W is —CH$_2$—, R$^1$ is Et, R$^2$ is Cl, R$^5$ is CH$_3$, R$^6$ CH$_3$, L—G is C(O)—t-Bu, and |
| 915 W is —CH$_2$—, R$^1$ is Et, R$^2$ is Cl, R$^5$ is CH$_3$, R$^6$ CH$_3$, L—G is CO$_2$Me, and |
| 916 W is —CH$_2$—, R$^1$ is Et, R$^2$ is Cl, R$^5$ is CH$_3$, R$^6$ CH$_3$, L—G is CO$_2$Et, and |
| 917 W is —CH$_2$—, R$^1$ is Et, R$^2$ is Cl, R$^5$ is CH$_3$, R$^6$ CH$_3$, L—G is CO$_2$—i-Pr, and |
| 918 W is —CH$_2$—, R$^1$ is Et, R$^2$ is Cl, R$^5$ is CH$_3$, R$^6$ CH$_3$, L—G is CO$_2$—t-Bu, and |
| 919 W is —CH$_2$—, R$^1$ is Et, R$^2$ is Cl, R$^5$ is CH$_3$, R$^6$ CH$_3$, L—G is SO$_2$Me, and |
| 920 W is —CH$_2$—, R$^1$ is Et, R$^2$ is Br, R$^5$ is CH$_3$, R$^6$ CH$_3$, L—G is H, and |
| 921 W is —CH$_2$—, R$^1$ is Et, R$^2$ is Br, R$^5$ is CH$_3$, R$^6$ CH$_3$, L—G is C(O)Me, and |
| 922 W is —CH$_2$—, R$^1$ is Et, R$^2$ is Br, R$^5$ is CH$_3$, R$^6$ CH$_3$, L—G is C(O)Et, and |
| 923 W is —CH$_2$—, R$^1$ is Et, R$^2$ is Br, R$^5$ is CH$_3$, R$^6$ CH$_3$, L—G is C(O)—i-Pr, and |
| 924 W is —CH$_2$—, R$^1$ is Et, R$^2$ is Br, R$^5$ is CH$_3$, R$^6$ CH$_3$, L—G is C(O)—t-Bu, and |
| 925 W is —CH$_2$—, R$^1$ is Et, R$^2$ is Br, R$^5$ is CH$_3$, R$^6$ CH$_3$, L—G is CO$_2$Me, and |
| 926 W is —CH$_2$—, R$^1$ is Et, R$^2$ is Br, R$^5$ is CH$_3$, R$^6$ CH$_3$, L—G is CO$_2$Et, and |
| 927 W is —CH$_2$—, R$^1$ is Et, R$^2$ is Br, R$^5$ is CH$_3$, R$^6$ CH$_3$, L—G is CO$_2$—i-Pr, and |
| 928 W is —CH$_2$—, R$^1$ is Et, R$^2$ is Br, R$^5$ is CH$_3$, R$^6$ CH$_3$, L—G is CO$_2$—t-Bu, and |
| 929 W is —CH$_2$—, R$^1$ is Et, R$^2$ is Br, R$^5$ is CH$_3$, R$^6$ CH$_3$, L—G is SO$_2$Me, and |
| 930 W is —CH$_2$—, R$^1$ is Et, R$^2$ is I, R$^5$ is CH$_3$, R$^6$ CH$_3$, L—G is H, and |
| 931 W is —CH$_2$—, R$^1$ is Et, R$^2$ is I, R$^5$ is CH$_3$, R$^6$ CH$_3$, L—G is C(O)Me, and |
| 932 W is —CH$_2$—, R$^1$ is Et, R$^2$ is I, R$^5$ is CH$_3$, R$^6$ CH$_3$, L—G is C(O)Et, and |
| 933 W is —CH$_2$—, R$^1$ is Et, R$^2$ is I, R$^5$ is CH$_3$, R$^6$ CH$_3$, L—G is C(O)—i-Pr, and |

-continued

| Table Row Heading |
| --- |
| 934 W is —CH$_2$—, R$^1$ is Et, R$^2$ is I, R$^5$ is CH$_3$, R$^6$ CH$_3$, L—G is C(O)—t-Bu, and |
| 935 W is —CH$_2$—, R$^1$ is Et, R$^2$ is I, R$^5$ is CH$_3$, R$^6$ CH$_3$, L—G is CO$_2$Me, and |
| 936 W is —CH$_2$—, R$^1$ is Et, R$^2$ is I, R$^5$ is CH$_3$, R$^6$ CH$_3$, L—G is CO$_2$Et, and |
| 937 W is —CH$_2$—, R$^1$ is Et, R$^2$ is I, R$^5$ is CH$_3$, R$^6$ CH$_3$, L—G is CO$_2$—i-Pr, and |
| 938 W is —CH$_2$—, R$^1$ is Et, R$^2$ is I, R$^5$ is CH$_3$, R$^6$ CH$_3$, L—G is CO$_2$—t-Bu, and |
| 939 W is —CH$_2$—, R$^1$ is Et, R$^2$ is I, R$^5$ is CH$_3$, R$^6$ CH$_3$, L—G is SO$_2$Me, and |
| 940 W is —CH$_2$—, R$^1$ is Et, R$^2$ is OMe, R$^5$ is CH$_3$, R$^6$ CH$_3$, L—G is H, and |
| 941 W is —CH$_2$—, R$^1$ is Et, R$^2$ is OMe, R$^5$ is CH$_3$, R$^6$ CH$_3$, L—G is C(O)Me, and |
| 942 W is —CH$_2$—, R$^1$ is Et, R$^2$ is OMe, R$^5$ is CH$_3$, R$^6$ CH$_3$, L—G is C(O)Et, and |
| 943 W is —CH$_2$—, R$^1$ is Et, R$^2$ is OMe, R$^5$ is CH$_3$, R$^6$ CH$_3$, L—G is C(O)—i-Pr, and |
| 944 W is —CH$_2$—, R$^1$ is Et, R$^2$ is OMe, R$^5$ is CH$_3$, R$^6$ CH$_3$, L—G is C(O)—t-Bu, and |
| 945 W is —CH$_2$—, R$^1$ is Et, R$^2$ is OMe, R$^5$ is CH$_3$, R$^6$ CH$_3$, L—G is CO$_2$Me, and |
| 946 W is —CH$_2$—, R$^1$ is Et, R$^2$ is OMe, R$^5$ is CH$_3$, R$^6$ CH$_3$, L—G is CO$_2$Et, and |
| 947 W is —CH$_2$—, R$^1$ is Et, R$^2$ is OMe, R$^5$ is CH$_3$, R$^6$ CH$_3$, L—G is CO$_2$—i-Pr, and |
| 948 W is —CH$_2$—, R$^1$ is Et, R$^2$ is OMe, R$^5$ is CH$_3$, R$^6$ CH$_3$, L—G is CO$_2$—t-Bu, and |
| 949 W is —CH$_2$—, R$^1$ is Et, R$^2$ is OMe, R$^5$ is CH$_3$, R$^6$ CH$_3$, L—G is SO$_2$Me, and |
| 950 W is —CH$_2$—, R$^1$ is Et, R$^2$ is CN, R$^5$ is CH$_3$, R$^6$ CH$_3$, L—G is H, and |
| 951 W is —CH$_2$—, R$^1$ is Et, R$^2$ is CN, R$^5$ is CH$_3$, R$^6$ CH$_3$, L—G is C(O)Me, and |
| 952 W is —CH$_2$—, R$^1$ is Et, R$^2$ is CN, R$^5$ is CH$_3$, R$^6$ CH$_3$, L—G is C(O)Et, and |
| 953 W is —CH$_2$—, R$^1$ is Et, R$^2$ is CN, R$^5$ is CH$_3$, R$^6$ CH$_3$, L—G is C(O)—i-Pr, and |
| 954 W is —CH$_2$—, R$^1$ is Et, R$^2$ is CN, R$^5$ is CH$_3$, R$^6$ CH$_3$, L—G is C(O)—t-Bu, and |
| 955 W is —CH$_2$—, R$^1$ is Et, R$^2$ is CN, R$^5$ is CH$_3$, R$^6$ CH$_3$, L—G is CO$_2$Me, and |
| 956 W is —CH$_2$—, R$^1$ is Et, R$^2$ is CN, R$^5$ is CH$_3$, R$^6$ CH$_3$, L—G is CO$_2$Et, and |
| 957 W is —CH$_2$—, R$^1$ is Et, R$^2$ is CN, R$^5$ is CH$_3$, R$^6$ CH$_3$, L—G is CO$_2$—i-Pr, and |
| 958 W is —CH$_2$—, R$^1$ is Et, R$^2$ is CN, R$^5$ is CH$_3$, R$^6$ CH$_3$, L—G is CO$_2$—t-Bu, and |
| 959 W is —CH$_2$—, R$^1$ is Et, R$^2$ is CN, R$^5$ is CH$_3$, R$^6$ CH$_3$, L—G is SO$_2$Me, and |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
| --- | --- | --- | --- |
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, Synthetic Detergents, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

EXAMPLE A

High Strength Concentrate

| | |
|---|---|
| Compound 1 | 98.5% |
| silica aerogel | 0.5% |
| synthetic amorphous fine silica | 1.0% |

EXAMPLE B

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE C

Granule

| | |
|---|---|
| Compound 1 | 10.0% |
| attapulgite granules (low volatile matter, 0.71/0.30 mm; U.S.S. No. 25-50 sieves) | 90.0% |

EXAMPLE D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE E

Emulsifiable Concentrate

| | |
|---|---|
| Compound 1 | 10.0% |
| polyoxyethylene sorbitol hexoleate | 20.0% |
| $C_6$-$C_{10}$ fatty acid methyl ester | 70.0% |

EXAMPLE F

Microemulsion

| | |
|---|---|
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE G

Suspension Concentrate

| | |
|---|---|
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

EXAMPLE H

Emulsion in Water

| | |
|---|---|
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

EXAMPLE I

Oil Dispersion

| | |
|---|---|
| Compound 1 | 25% |
| polyoxyethylene sorbitol hexaoleate | 15% |
| organically modified bentonite clay | 2.5% |
| fatty acid methyl ester | 57.5% |

The present disclosure also includes Examples A through I above except "Compound 1" is replaced with "Compound 2" and "Compound 3". "Compound 4", "Compound 5", "Compound 6", Compound 7" or "Compound 8" above as described in Index Table A. Test results indicate that the compounds of the present invention are highly active preemergent and/or postemergent herbicides and/or plant growth regulants. The compounds of the invention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation. Undesired vegetation includes at least one selected from the group consisting of grass weeds and broadleaf weeds. Undesired vegetation is selected from the group consisting of annual bluegrass (*Poa annua*), Benghal dayflower, blackgrass (*Alopecurus myosuroides*), black nightshade (eastern black nightshade, *Solanum ptycanthum*), broadleaf signalgrass, Canada thistle, cheat, common cocklebur (*Xanthium pensylvanicum* or *Xanthium strumarium*), corn poppies, field violet (*Viola arvensis*), goosegrass (*Eleusine indica*), guinea grass, hairy beggarticks (*Bidens pilosa*), herbicide-resistant blackgrass, horseweed, Italian rye grass, jimsonweed, Johnson grass (*Sorghum halepense*), large crabgrass (*Digitaria sanguinalis*), little seed canary grass, morning glory, Pennsylvania smartweed, ladysthumb smartweed (*Polygonum Persicaria*), pitted morning glory, prickly sida, quackgrass, redroot pigweed, palmer pigweed (*Amaranthus palmeri*), shattercane, shepherd's purse, windgrass, silky windgrass (*Apera spica-venti*), sunflower (*Helianthus annuus*, as a weed in a potato crop), wild buckwheat (*Polygonum convolvulus*), wild mustard (*Sinapis arvensis*), wild oat (*Avena fatua*), wild pointsettia, yellow foxtail, yellow nutsedge (*Cyperus esculentus*), johnsongrass (*Sorghum halepense*), lambsquarters (*Chenopodium album*), morningglory (*Ipomoea coccinea*), common waterhemp (*Amaranthus rudis*), surinam grass (*Brachiaria decumbens*), downy bromegrass (*Bromus tectorum*), woolly cupgrass (*Eriochloa villosa*), bermudagrass (*Cynodon dactylon*), Russian thistle (*Salsola kali*), velvetleaf (*Abutilon theophrasti*), common chickweed (*Stellaria media*), henbit deadnettle (*Lamium amplexicaule*), littleseed canarygrass (*Phalaris minor*), field poppy (*Papaver rhoeas*), scentless chamomile (*Matricaria inodora*), bird's-eye speedwell (*Veronica persica*), wild radish (*Raphanus raphanistrum*), wild poinsettia (*Euphorbia heterophylla*), Brazilian crabgrass (*Digitaria horizontalis*), fall panicum (*Panicum dichotomiflorum*), southern sandbur (*Cenchrus echinatus*), arrowleaf sida (*Sida rhombifolia*), Virginia dayflower (*Commelina virginica*), field bindweed (*Convolvulus arvensis*), monochoria (*Monochoria vaginalis*), hardstem bulrush (*Scirpus juncoides*), purple redstem (*Ammannia coccinea*), bearded sprangletop (*Leptochloa fascicularis*), common waterplantain (*Alisma plantago-aquatica*), and late watergrass (*Echinochloa oryzicola*).

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Plant varieties and cultivars of the desired vegetation in the locus treated with a compound of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Although most typically, compounds of the invention are used to control undesired vegetation, contact of desired vegetation in the treated locus with compounds of the invention may result in super-additive or synergistic (enhanced) effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent.

For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, S-beflubutamide, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyranil, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazasulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, triallate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxy-pyrido[2,3-b]pyrazin-6(5H)-one), 4-(2,6-diethyl-4-methylphenyl)-5-hydroxy-2,6-dimethyl-3 (2H)-pyridazinone), 5-[[(2,6-difluorophenyl)methoxy]methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2, 55-oxadiazol-3-yl)-3-(methylsulfinyl)-4-(trifluoromethyl) benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Preferred for better control of undesired vegetation (e.g., lower use rate such as from greater-than-additive effects, broader spectrum of weeds controlled, or enhanced crop safety) or for preventing the development of resistant weeds are mixtures of a compound of this invention with a herbicide selected from the group consisting of atrazine, azimsulfuron, beflubutamid, S-beflubutamide, benzisothiazolinone, carfentrazone-ethyl, chlorimuron-ethyl, chlorsulfuron-methyl, clomazone, clopyralid potassium, cloransulam-methyl, 2-[(2,5-dichlorophenyl)methyl]-4,4-dimethyl-3-isoxazolidinone, ethametsulfuron-methyl, flumetsulam, 4-(4-fluorophenyl)-6-[(2-hydroxy-6-oxo-1-cyclohexen-1-yl)carbonyl]-2-methyl-i 1,2,4-triazine-3,5-(2H,4H)-dione, flupyrsulfuron-methyl, fluthiacet-methyl, fomesafen, imazethapyr, lenacil, mesotrione, metribuzin, metsulfuron-methyl, pethoxamid, picloram, pyroxasulfone, quinclorac, rimsulfuron, S-metolachlor, sulfentrazone, thifensulfuron-methyl, triflusulfuron-methyl and tribenuron-methyl.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th Edition, C. D. S. Tomlin, Ed., British Crop Protection Council, Farnham, Surrey, U. K., 2003 and *The BioPesticide Manual*, 2nd Edition, L. G. Copping, Ed., British Crop Protection Council, Farnham, Surrey, U. K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic or (enhanced)) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism (enhancement) of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl] benzene (BCS), 4-(dichloroacetyl)-1-oxa-4-azospiro[4.5] decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Compounds of the invention can also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents. Table A1 lists specific combinations of a Component (a) with Component (b) illustrative of the mixtures, compositions and methods of the present invention. Compound 1 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:192-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
| --- | --- | --- | --- | --- |
| 1 | 2,4-D | 1:192-6:1 | 1:64-2:1 | 1:24-1:3 |
| 1 | Acetochlor | 1:768-2:1 | 1:256-1:2 | 1:96-1:11 |
| 1 | Acifluorfen | 1:96-12:1 | 1:32-4:1 | 1:12-1:2 |
| 1 | Aclonifen | 1:857-2:1 | 1:285-1:3 | 1:107-1:12 |
| 1 | Alachlor | 1:768-2:1 | 1:256-1:2 | 1:96-1:11 |
| 1 | Ametryn | 1:384-3:1 | 1:128-1:1 | 1:48-1:6 |
| 1 | Amicarbazone | 1:192-6:1 | 1:64-2:1 | 1:24-1:3 |
| 1 | Amidosulfuron | 1:6-168:1 | 1:2-56:1 | 1:1-11:1 |
| 1 | Aminocyclopyrachlor | 1:48-24:1 | 1:16-8:1 | 1:6-2:1 |
| 1 | Aminopyralid | 1:20-56:1 | 1:6-19:1 | 1:2-4:1 |
| 1 | Amitrole | 1:768-2:1 | 1:256-1:2 | 1:96-1:11 |
| 1 | Anilofos | 1:96-12:1 | 1:32-4:1 | 1:12-1:2 |
| 1 | Asulam | 1:960-2:1 | 1:320-1:3 | 1:120-1:14 |
| 1 | Atrazine | 1:192-6:1 | 1:64-2:1 | 1:24-1:3 |
| 1 | Azimsulfuron | 1:6-168:1 | 1:2-56:1 | 1:1-11:1 |
| 1 | Beflubutamid | 1:342-4:1 | 1:114-2:1 | 1:42-1:5 |
| 1 | S-Beflubutamid | 1:171-4:0.5 | 1:57-2:0.5 | 1:21-1:2.5 |
| 1 | Benfuresate | 1:617-2:1 | 1:205-1:2 | 1:77-1:9 |
| 1 | Bensulfuron-methyl | 1:25-45:1 | 1:8-15:1 | 1:3-3:1 |
| 1 | Bentazone | 1:192-6:1 | 1:64-2:1 | 1:24-1:3 |
| 1 | Benzobicyclon | 1:85-14:1 | 1:28-5:1 | 1:10-1:2 |
| 1 | Benzofenap | 1:257-5:1 | 1:85-2:1 | 1:32-1:4 |
| 1 | Bicyclopyrone | 1:42-27:1 | 1:14-9:1 | 1:5-2:1 |
| 1 | Bifenox | 1:257-5:1 | 1:85-2:1 | 1:32-1:4 |
| 1 | Bispyribac-sodium | 1:10-112:1 | 1:3-38:1 | 1:1-7:1 |
| 1 | Bromacil | 1:384-3:1 | 1:128-1:1 | 1:48-1:6 |

TABLE A1-continued

| Component (a) (Compound #) | Component (b) | Typical Weight Ratio | More Typical Weight Ratio | Most Typical Weight Ratio |
|---|---|---|---|---|
| 1 | Bromobutide | 1:384-3:1 | 1:128-1:1 | 1:48-1:6 |
| 1 | Bromoxynil | 1:96-12:1 | 1:32-4:1 | 1:12-1:2 |
| 1 | Butachlor | 1:768-2:1 | 1:256-1:2 | 1:96-1:11 |
| 1 | Butafenacil | 1:42-27:1 | 1:14-9:1 | 1:5-2:1 |
| 1 | Butylate | 1:1542-1:2 | 1:514-1:5 | 1:192-1:22 |
| 1 | Carfenstrole | 1:192-6:1 | 1:64-2:1 | 1:24-1:3 |
| 1 | Carfentrazone-ethyl | 1:128-9:1 | 1:42-3:1 | 1:16-1:2 |
| 1 | Chlorimuron-ethyl | 1:8-135:1 | 1:2-45:1 | 1:1-9:1 |
| 1 | Chlorotoluron | 1:768-2:1 | 1:256-1:2 | 1:96-1:11 |
| 1 | Chlorsulfuron | 1:6-168:1 | 1:2-56:1 | 1:1-11:1 |
| 1 | Cincosulfuron | 1:17-68:1 | 1:5-23:1 | 1:2-5:1 |
| 1 | Cinidon-ethyl | 1:384-3:1 | 1:128-1:1 | 1:48-1:6 |
| 1 | Cinmethylin | 1:34-34:1 | 1:11-12:1 | 1:4-3:1 |
| 1 | Clacyfos | 1:34-34:1 | 1:11-12:1 | 1:4-3:1 |
| 1 | Clethodim | 1:48-24:1 | 1:16-8:1 | 1:6-2:1 |
| 1 | Clodinafop-propargyl | 1:20-56:1 | 1:6-19:1 | 1:2-4:1 |
| 1 | Clomazone | 1:384-3:1 | 1:128-1:1 | 1:48-1:6 |
| 1 | Clomeprop | 1:171-7:1 | 1:57-3:1 | 1:21-1:3 |
| 1 | Clopyralid | 1:192-6:1 | 1:64-2:1 | 1:24-1:3 |
| 1 | Cloransulam-methyl | 1:12-96:1 | 1:4-32:1 | 1:1-6:1 |
| 1 | Cumyluron | 1:384-3:1 | 1:128-1:1 | 1:48-1:6 |
| 1 | Cyanazine | 1:384-3:1 | 1:128-1:1 | 1:48-1:6 |
| 1 | Cyclopyrimorate | 1:17-68:1 | 1:5-23:1 | 1:2-5:1 |
| 1 | Cyclosulfamuron | 1:17-68:1 | 1:5-23:1 | 1:2-5:1 |
| 1 | Cycloxydim | 1:96-12:1 | 1:32-4:1 | 1:12-1:2 |
| 1 | Cyhalofop | 1:25-45:1 | 1:8-15:1 | 1:3-3:1 |
| 1 | Daimuron | 1:192-6:1 | 1:64-2:1 | 1:24-1:3 |
| 1 | Desmedipham | 1:322-4:1 | 1:107-2:1 | 1:40-1:5 |
| 1 | Dicamba | 1:192-6:1 | 1:64-2:1 | 1:24-1:3 |
| 1 | Dichlobenil | 1:1371-1:2 | 1:457-1:4 | 1:171-1:20 |
| 1 | Dichlorprop | 1:925-2:1 | 1:308-1:3 | 1:115-1:13 |
| 1 | Diclofop-methyl | 1:384-3:1 | 1:128-1:1 | 1:48-1:6 |
| 1 | Diclosulam | 1:10-112:1 | 1:3-38:1 | 1:1-7:1 |
| 1 | Difenzoquat | 1:288-4:1 | 1:96-2:1 | 1:36-1:4 |
| 1 | Diflufenican | 1:857-2:1 | 1:285-1:3 | 1:107-1:12 |
| 1 | Diflufenzopyr | 1:12-96:1 | 1:4-32:1 | 1:1-6:1 |
| 1 | Dimethachlor | 1:768-2:1 | 1:256-1:2 | 1:96-1:11 |
| 1 | Dimethametryn | 1:192-6:1 | 1:64-2:1 | 1:24-1:3 |
| 1 | Dimethenamid-P | 1:384-3:1 | 1:128-1:1 | 1:48-1:6 |
| 1 | Dithiopyr | 1:192-6:1 | 1:64-2:1 | 1:24-1:3 |
| 1 | Diuron | 1:384-3:1 | 1:128-1:1 | 1:48-1:6 |
| 1 | EPTC | 1:768-2:1 | 1:256-1:2 | 1:96-1:11 |
| 1 | Esprocarb | 1:1371-1:2 | 1:457-1:4 | 1:171-1:20 |
| 1 | Ethalfluralin | 1:384-3:1 | 1:128-1:1 | 1:48-1:6 |
| 1 | Ethametsulfuron-methyl | 1:17-68:1 | 1:5-23:1 | 1:2-5:1 |
| 1 | Ethoxyfen | 1:8-135:1 | 1:2-45:1 | 1:1-9:1 |
| 1 | Ethoxysulfuron | 1:20-56:1 | 1:6-19:1 | 1:2-4:1 |
| 1 | Etobenzanid | 1:257-5:1 | 1:85-2:1 | 1:32-1:4 |
| 1 | Fenoxaprop-ethyl | 1:120-10:1 | 1:40-4:1 | 1:15-1:2 |
| 1 | Fenoxasulfone | 1:85-14:1 | 1:28-5:1 | 1:10-1:2 |
| 1 | Fenquinotrione | 1:17-68:1 | 1:5-23:1 | 1:2-5:1 |
| 1 | Fentrazamide | 1:17-68:1 | 1:5-23:1 | 1:2-5:1 |
| 1 | Flazasulfuron | 1:17-68:1 | 1:5-23:1 | 1:2-5:1 |
| 1 | Florasulam | 1:2-420:1 | 1:1-140:1 | 2:1-27:1 |
| 1 | Fluazifop-butyl | 1:192-6:1 | 1:64-2:1 | 1:24-1:3 |
| 1 | Flucarbazone | 1:8-135:1 | 1:2-45:1 | 1:1-9:1 |
| 1 | Flucetosulfuron | 1:8-135:1 | 1:2-45:1 | 1:1-9:1 |
| 1 | Flufenacet | 1:257-5:1 | 1:85-2:1 | 1:32-1:4 |
| 1 | Flumetsulam | 1:24-48:1 | 1:8-16:1 | 1:3-3:1 |
| 1 | Flumiclorac-pentyl | 1:10-112:1 | 1:3-38:1 | 1:1-7:1 |
| 1 | Flumioxazin | 1:25-45:1 | 1:8-15:1 | 1:3-3:1 |
| 1 | Fluometuron | 1:384-3:1 | 1:128-1:1 | 1:48-1:6 |
| 1 | Flupyrsulfuron-methyl | 1:3-336:1 | 1:1-112:1 | 2:1-21:1 |
| 1 | Fluridone | 1:384-3:1 | 1:128-1:1 | 1:48-1:6 |
| 1 | Fluroxypyr | 1:96-12:1 | 1:32-4:1 | 1:12-1:2 |
| 1 | Flurtamone | 1:857-2:1 | 1:285-1:3 | 1:107-1:12 |
| 1 | Fluthiacet-methyl | 1:48-42:1 | 1:16-14:1 | 1:3-3:1 |
| 1 | Fomesafen | 1:96-12:1 | 1:32-4:1 | 1:12-1:2 |
| 1 | Foramsulfuron | 1:13-84:1 | 1:4-28:1 | 1:1-6:1 |
| 1 | Glufosinate | 1:288-4:1 | 1:96-2:1 | 1:36-1:4 |
| 1 | Glyphosate | 1:288-4:1 | 1:96-2:1 | 1:36-1:4 |
| 1 | Halosulfuron-methyl | 1:17-68:1 | 1:5-23:1 | 1:2-5:1 |
| 1 | Halauxifen | 1:20-56:1 | 1:6-19:1 | 1:2-4:1 |
| 1 | Halauxifen methyl | 1:20-56:1 | 1:6-19:1 | 1:2-4:1 |
| 1 | Haloxyfop-methyl | 1:34-34:1 | 1:11-12:1 | 1:4-3:1 |
| 1 | Hexazinone | 1:192-6:1 | 1:64-2:1 | 1:24-1:3 |
| 1 | Hydantocidin | 1:1100-16:1 | 1:385-8:1 | 1:144-4:1 |

TABLE A1-continued

| Component (a) (Compound #) | Component (b) | Typical Weight Ratio | More Typical Weight Ratio | Most Typical Weight Ratio |
|---|---|---|---|---|
| 1 | Imazamox | 1:13-84:1 | 1:4-28:1 | 1:1-6:1 |
| 1 | Imazapic | 1:20-56:1 | 1:6-19:1 | 1:2-4:1 |
| 1 | Imazapyr | 1:85-14:1 | 1:28-5:1 | 1:10-1:2 |
| 1 | Imazaquin | 1:34-34:1 | 1:11-12:1 | 1:4-3:1 |
| 1 | Imazethabenz-methyl | 1:171-7:1 | 1:57-3:1 | 1:21-1:3 |
| 1 | Imazethapyr | 1:24-48:1 | 1:8-16:1 | 1:3-3:1 |
| 1 | Imazosulfuron | 1:27-42:1 | 1:9-14:1 | 1:3-3:1 |
| 1 | Indanofan | 1:342-4:1 | 1:114-2:1 | 1:42-1:5 |
| 1 | Indaziflam | 1:25-45:1 | 1:8-15:1 | 1:3-3:1 |
| 1 | Iodosulfuron-methyl | 1:3-336:1 | 1:1-112:1 | 2:1-21:1 |
| 1 | Ioxynil | 1:192-6:1 | 1:64-2:1 | 1:24-1:3 |
| 1 | Ipfencarbazone | 1:85-14:1 | 1:28-5:1 | 1:10-1:2 |
| 1 | Isoproturon | 1:384-3:1 | 1:128-1:1 | 1:48-1:6 |
| 1 | Isoxaben | 1:288-4:1 | 1:96-2:1 | 1:36-1:4 |
| 1 | Isoxaflutole | 1:60-20:1 | 1:20-7:1 | 1:7-2:1 |
| 1 | Lactofen | 1:42-27:1 | 1:14-9:1 | 1:5-2:1 |
| 1 | Lenacil | 1:384-3:1 | 1:128-1:1 | 1:48-1:6 |
| 1 | Linuron | 1:384-3:1 | 1:128-1:1 | 1:48-1:6 |
| 1 | MCPA | 1:192-6:1 | 1:64-2:1 | 1:24-1:3 |
| 1 | MCPB | 1:288-4:1 | 1:96-2:1 | 1:36-1:4 |
| 1 | Mecoprop | 1:768-2:1 | 1:256-1:2 | 1:96-1:11 |
| 1 | Mefenacet | 1:384-3:1 | 1:128-1:1 | 1:48-1:6 |
| 1 | Mefluidide | 1:192-6:1 | 1:64-2:1 | 1:24-1:3 |
| 1 | Mesosulfuron-methyl | 1:5-224:1 | 1:1-75:1 | 1:1-14:1 |
| 1 | Mesotrione | 1:42-27:1 | 1:14-9:1 | 1:5-2:1 |
| 1 | Metamifop | 1:42-27:1 | 1:14-9:1 | 1:5-2:1 |
| 1 | Metazachlor | 1:384-3:1 | 1:128-1:1 | 1:48-1:6 |
| 1 | Metazosulfuron | 1:25-45:1 | 1:8-15:1 | 1:3-3:1 |
| 1 | Methabenzthiazuron | 1:768-2:1 | 1:256-1:2 | 1:96-1:11 |
| 1 | Metolachlor | 1:768-2:1 | 1:256-1:2 | 1:96-1:11 |
| 1 | Metosulam | 1:8-135:1 | 1:2-45:1 | 1:1-9:1 |
| 1 | Metribuzin | 1:192-6:1 | 1:64-2:1 | 1:24-1:3 |
| 1 | Metsulfuron-methyl | 1:2-560:1 | 1:1-187:1 | 3:1-35:1 |
| 1 | Molinate | 1:1028-2:1 | 1:342-1:3 | 1:128-1:15 |
| 1 | Napropamide | 1:384-3:1 | 1:128-1:1 | 1:48-1:6 |
| 1 | Napropamide-M | 1:192-6:1 | 1:64-2:1 | 1:24-1:3 |
| 1 | Naptalam | 1:192-6:1 | 1:64-2:1 | 1:24-1:3 |
| 1 | Nicosulfuron | 1:12-96:1 | 1:4-32:1 | 1:1-6:1 |
| 1 | Norflurazon | 1:1152-1:1 | 1:384-1:3 | 1:144-1:16 |
| 1 | Orbencarb | 1:1371-1:2 | 1:457-1:4 | 1:171-1:20 |
| 1 | Orthosulfamuron | 1:20-56:1 | 1:6-19:1 | 1:2-4:1 |
| 1 | Oryzalin | 1:514-3:1 | 1:171-1:2 | 1:64-1:8 |
| 1 | Oxadiargyl | 1:384-3:1 | 1:128-1:1 | 1:48-1:6 |
| 1 | Oxadiazon | 1:548-3:1 | 1:182-1:2 | 1:68-1:8 |
| 1 | Oxasulfuron | 1:27-42:1 | 1:9-14:1 | 1:3-3:1 |
| 1 | Oxaziclomefone | 1:42-27:1 | 1:14-9:1 | 1:5-2:1 |
| 1 | Oxyfluorfen | 1:384-3:1 | 1:128-1:1 | 1:48-1:6 |
| 1 | Paraquat | 1:192-6:1 | 1:64-2:1 | 1:24-1:3 |
| 1 | Pendimethalin | 1:384-3:1 | 1:128-1:1 | 1:48-1:6 |
| 1 | Penoxsulam | 1:10-112:1 | 1:3-38:1 | 1:1-7:1 |
| 1 | Penthoxamid | 1:384-3:1 | 1:128-1:1 | 1:48-1:6 |
| 1 | Pentoxazone | 1:102-12:1 | 1:34-4:1 | 1:12-1:2 |
| 1 | Phenmedipham | 1:102-12:1 | 1:34-4:1 | 1:12-1:2 |
| 1 | Picloram | 1:96-12:1 | 1:32-4:1 | 1:12-1:2 |
| 1 | Picolinafen | 1:34-34:1 | 1:11-12:1 | 1:4-3:1 |
| 1 | Pinoxaden | 1:25-45:1 | 1:8-15:1 | 1:3-3:1 |
| 1 | Pretilachlor | 1:192-6:1 | 1:64-2:1 | 1:24-1:3 |
| 1 | Primisulfuron-methyl | 1:8-135:1 | 1:2-45:1 | 1:1-9:1 |
| 1 | Prodiamine | 1:384-3:1 | 1:128-1:1 | 1:48-1:6 |
| 1 | Profoxydim | 1:42-27:1 | 1:14-9:1 | 1:5-2:1 |
| 1 | Prometryn | 1:384-3:1 | 1:128-1:1 | 1:48-1:6 |
| 1 | Propachlor | 1:1152-1:1 | 1:384-1:3 | 1:144-1:16 |
| 1 | Propanil | 1:384-3:1 | 1:128-1:1 | 1:48-1:6 |
| 1 | Propaquizafop | 1:48-24:1 | 1:16-8:1 | 1:6-2:1 |
| 1 | Propoxycarbazone | 1:17-68:1 | 1:5-23:1 | 1:2-5:1 |
| 1 | Propyrisulfuron | 1:17-68:1 | 1:5-23:1 | 1:2-5:1 |
| 1 | Propyzamide | 1:384-3:1 | 1:128-1:1 | 1:48-1:6 |
| 1 | Prosulfocarb | 1:1200-1:2 | 1:400-1:4 | 1:150-1:17 |
| 1 | Prosulfuron | 1:6-168:1 | 1:2-56:1 | 1:1-11:1 |
| 1 | Pyraclonil | 1:42-27:1 | 1:14-9:1 | 1:5-2:1 |
| 1 | Pyraflufen-ethyl | 1:5-224:1 | 1:1-75:1 | 1:1-14:1 |
| 1 | Pyrasulfotole | 1:13-84:1 | 1:4-28:1 | 1:1-6:1 |
| 1 | Pyrazolynate | 1:857-2:1 | 1:285-1:3 | 1:107-1:12 |
| 1 | Pyrazosulfuron-ethyl | 1:10-112:1 | 1:3-38:1 | 1:1-7:1 |
| 1 | Pyrazoxyfen | 1:5-224:1 | 1:1-75:1 | 1:1-14:1 |
| 1 | Pyribenzoxim | 1:10-112:1 | 1:3-38:1 | 1:1-7:1 |
| 1 | Pyributicarb | 1:384-3:1 | 1:128-1:1 | 1:48-1:6 |

TABLE A1-continued

| Component (a) (Compound #) | Component (b) | Typical Weight Ratio | More Typical Weight Ratio | Most Typical Weight Ratio |
|---|---|---|---|---|
| 1 | Pyridate | 1:288-4:1 | 1:96-2:1 | 1:36-1:4 |
| 1 | Pyriftalid | 1:10-112:1 | 1:3-38:1 | 1:1-7:1 |
| 1 | Pyriminobac-methyl | 1:20-56:1 | 1:6-19:1 | 1:2-4:1 |
| 1 | Pyrimisulfan | 1:17-68:1 | 1:5-23:1 | 1:2-5:1 |
| 1 | Pyrithiobac | 1:24-48:1 | 1:8-16:1 | 1:3-3:1 |
| 1 | Pyroxasulfone | 1:85-14:1 | 1:28-5:1 | 1:10-1:2 |
| 1 | Pyroxsulam | 1:5-224:1 | 1:1-75:1 | 1:1-14:1 |
| 1 | Quinclorac | 1:192-6:1 | 1:64-2:1 | 1:24-1:3 |
| 1 | Quizalofop-ethyl | 1:42-27:1 | 1:14-9:1 | 1:5-2:1 |
| 1 | Rimsulfuron | 1:13-84:1 | 1:4-28:1 | 1:1-6:1 |
| 1 | Saflufenacil | 1:25-45:1 | 1:8-15:1 | 1:3-3:1 |
| 1 | Sethoxydim | 1:96-12:1 | 1:32-4:1 | 1:12-1:2 |
| 1 | Simazine | 1:384-3:1 | 1:128-1:1 | 1:48-1:6 |
| 1 | Sulcotrione | 1:120-10:1 | 1:40-4:1 | 1:15-1:2 |
| 1 | Sulfentrazone | 1:147-8:1 | 1:49-3:1 | 1:18-1:3 |
| 1 | Sulfometuron-methyl | 1:34-34:1 | 1:11-12:1 | 1:4-3:1 |
| 1 | Sulfosulfuron | 1:8-135:1 | 1:2-45:1 | 1:1-9:1 |
| 1 | Tebuthiuron | 1:384-3:1 | 1:128-1:1 | 1:48-1:6 |
| 1 | Tefuryltrione | 1:42-27:1 | 1:14-9:1 | 1:5-2:1 |
| 1 | Tembotrione | 1:31-37:1 | 1:10-13:1 | 1:3-3:1 |
| 1 | Tepraloxydim | 1:25-45:1 | 1:8-15:1 | 1:3-3:1 |
| 1 | Terbacil | 1:288-4:1 | 1:96-2:1 | 1:36-1:4 |
| 1 | Terbuthylazine | 1:857-2:1 | 1:285-1:3 | 1:107-1:12 |
| 1 | Terbutryn | 1:192-6:1 | 1:64-2:1 | 1:24-1:3 |
| 1 | Thenylchlor | 1:85-14:1 | 1:28-5:1 | 1:10-1:2 |
| 1 | Thiazopyr | 1:384-3:1 | 1:128-1:1 | 1:48-1:6 |
| 1 | Thiencarbazone | 1:3-336:1 | 1:1-112:1 | 2:1-21:1 |
| 1 | Thifensulfuron-methyl | 1:5-224:1 | 1:1-75:1 | 1:1-14:1 |
| 1 | Tiafenacil | 1:17-68:1 | 1:5-23:1 | 1:2-5:1 |
| 1 | Thiobencarb | 1:768-2:1 | 1:256-1:2 | 1:96-1:11 |
| 1 | Tolpyralate | 1:31-37:1 | 1:10-13:1 | 1:3-3:1 |
| 1 | Topramzone | 1:6-168:1 | 1:2-56:1 | 1:1-11:1 |
| 1 | Tralkoxydim | 1:68-17:1 | 1:22-6:1 | 1:8-2:1 |
| 1 | Triafamone | 1:2-420:1 | 1:1-140:1 | 2:1-27:1 |
| 1 | Triallate | 1:768-2:1 | 1:256-1:2 | 1:96-1:11 |
| 1 | Triasulfuron | 1:5-224:1 | 1:1-75:1 | 1:1-14:1 |
| 1 | Triaziflam | 1:171-7:1 | 1:57-3:1 | 1:21-1:3 |
| 1 | Tribenuron-methyl | 1:3-336:1 | 1:1-112:1 | 2:1-21:1 |
| 1 | Triclopyr | 1:192-6:1 | 1:64-2:1 | 1:24-1:3 |
| 1 | Trifloxysulfuron | 1:2-420:1 | 1:1-140:1 | 2:1-27:1 |
| 1 | Trifludimoxazin | 1:25-45:1 | 1:8-15:1 | 1:3-3:1 |
| 1 | Trifluralin | 1:288-4:1 | 1:96-2:1 | 1:36-1:4 |
| 1 | Triflusulfuron-methyl | 1:17-68:1 | 1:5-23:1 | 1:2-5:1 |
| 1 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 1 in the Component (a) column is identified in Index Table A. Thus, for example, in Table A2 the entries below the "Component (a)" column heading all recite "Compound 2" (i.e. Compound 2 identified in Index Table A), and the first line below the column headings in Table A2 specifically discloses a mixture of Compound 2 with 2,4-D. Tables A3 through A7 are constructed similarly.

| Table Number | Component (a) Column Entries |
|---|---|
| A2 | Compound 2 |
| A3 | Compound 3 |
| A4 | Compound 4 |
| A5 | Compound 5 |
| A6 | Compound 6 |
| A7 | Compound 7 |
| A8 | Compound 8 |

Preferred for better control of undesired vegetation (e.g., lower use rate such as from synergism (enhancement), broader spectrum of weeds controlled, or enhanced crop safety) or for preventing the development of resistant weeds are mixtures of a compound of this invention with a herbicide selected from the group consisting of chlorsulfuron, ethametsulfuron, chlorimuron-ethyl, mesotrione, thifensulfuron-methyl, flupyrsulfuron-methyl, tribenuron-methyl, metsulfuron-methyl, triflusulfuron-methyl, pyroxasulfone, pinoxaden, tembotrione, pyroxsulam, metolachlor and S-metolachlor.

The following Tests demonstrate the control efficacy of the compounds of this invention against specific weeds. The weed control afforded by the compounds is not limited, however, to these species. See Index Table A for compound descriptions. The abbreviation Me means methyl. The abbreviation "Cmpd. No." stands for "Compound Number". The abbreviation "Ex." stands for "Example" and is followed by a number indicating in which example the compound is prepared. Mass spectra are reported with an estimated precision within ±0.5 Da as the molecular weight of the highest isotopic abundance parent ion (M+1) formed by addition of $H^+$ (molecular weight of 1) to the molecule observed by using atmospheric pressure chemical ionization (AP+).

INDEX TABLE A

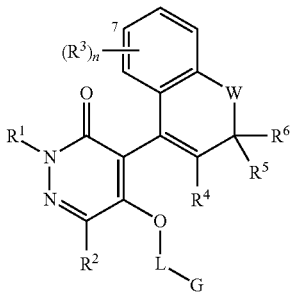

| Cmpd. No. | $R^1$ | $R^2$ | $(R^3)_n$ | $R^4$ | $R^5/R^6$ | W | L—G | Mass (AP+) |
|---|---|---|---|---|---|---|---|---|
| 1 (Ex. 1) | $CH_3$ | $CH_3$ | H | $CH_3$ | H/H | —$CH_2$— | $CH_3$ | 297 * |
| 2 (Ex. 2) | $CH_3$ | $CH_3$ | H | $CH_3$ | H/H | —$CH_2$— | H | 283 * |
| 3 (Ex. 3) | $CH_3$ | $CH_3$ | H | $CH_3$ | H/H | —O— | H | 285 * |
| 4 | $CH_3$ | $CH_3$ | 7-$CH_3$ | $CH_3$ | H/H | —$CH_2$— | H | 297 |
| 5 | $CH_3$ | $CH_3$ | H | $CH_3$ | H/H | —$CH_2$— | —C(=O)$CH_3$ | 325 |
| 6 | $CH_3$ | $CH_3$ | H | H | H/H | —C($CH_3$)$_2$— | $CH_3$ | 311 |
| 7 | $CH_3$ | $CH_3$ | H | H | H/H | —C($CH_3$)$_2$— | H | 297 |
| 8 | $CH_3$ | Cl | 7-$CH_3$ | $CH_3$ | H/H | —$CH_2$— | H | ** |

\* See Synthesis Example for $^1$H NMR data.
\*\* M.P. = 204-229° C.

BIOLOGICAL EXAMPLES OF THE INVENTION

Test A

Seeds of plant species selected from barnyardgrass (*Echinochloa crus-galli*), kochia (*Kochia scoparia*), ragweed (common ragweed, *Ambrosia elatior*), ryegrass, It. (Italian ryegrass, *Lolium multiflorum*), foxtail, green (green foxtail, *Setaria viridis*), and pigweed (*Amaranthus retroflexus*) were planted into a blend of loam soil and sand and treated preemergence with a directed soil spray using test chemicals formulated in a non-phytotoxic solvent mixture which included a surfactant.

At the same time, plants selected from these weed species and also wheat (*Triticum aestivum*), corn (*Zea mays*), blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 1000 g ai/ha Postemergence | Compound 1 | 1000 g ai/ha Postemergence | Compound 1 |
|---|---|---|---|
| Barnyardgrass | 60 | Kochia | 20 |
| Blackgrass | 70 | Pigweed | 80 |
| Corn | 10 | Ragweed | 90 |
| Foxtail, Green | 60 | Ryegrass, Italian | 90 |
| Galium | 100 | Wheat | 0 |

| 500 g ai/ha Postemergence | \multicolumn{4}{Compounds} | 500 g ai/ha Postemergence | \multicolumn{4}{Compounds} |

| 500 g ai/ha Postemergence | 2 | 3 | 6 | 7 | 500 g ai/ha Postemergence | 2 | 3 | 6 | 7 |
|---|---|---|---|---|---|---|---|---|---|
| Barnyardgrass | 20 | 10 | 0 | 30 | Kochia | 90 | 90 | 0 | 70 |
| Blackgrass | 20 | 10 | 20 | 10 | Pigweed | 90 | 100 | 0 | 90 |
| Corn | 10 | 10 | 0 | 10 | Ragweed | 90 | 90 | 20 | 70 |
| Foxtail, Giant | — | — | 0 | 10 | Ryegrass, Italian | 100 | 60 | 0 | 80 |
| Foxtail, Green | 70 | 20 | — | — | Wheat | 0 | 0 | 0 | 0 |
| Galium | 100 | — | 0 | 70 | | | | | |

| 125 g ai/ha Postemergence | 2 | 3 | 4 | 5 | 6 | 7 | 8 | 31 g ai/ha Postemergence | 4 | 5 | 8 |
|---|---|---|---|---|---|---|---|---|---|---|---|
| Barnyardgrass | 0 | 0 | 10 | 30 | 0 | 10 | 80 | Barnyardgrass | 10 | 20 | 50 |
| Blackgrass | 0 | 0 | 0 | 30 | 0 | 10 | 30 | Blackgrass | 0 | 0 | 20 |
| Corn | 10 | 0 | 0 | 20 | 0 | 0 | 20 | Corn | 0 | 20 | 0 |
| Foxtail, Giant | — | — | — | — | 0 | 0 | 80 | Foxtail, Giant | — | — | 60 |
| Foxtail, Green | 10 | 0 | 20 | 40 | — | — | — | Foxtail, Green | 10 | 20 | — |

TABLE A-continued

| | | | | | | | | | | | |
|---|---|---|---|---|---|---|---|---|---|---|---|
| Galium | 90 | — | 70 | 90 | 0 | 50 | 90 Galium | 40 | | 90 | 90 |
| Kochia | 80 | 70 | 20 | 80 | 0 | 30 | 50 Kochia | 0 | | 70 | 40 |
| Pigweed | 80 | 80 | 70 | 100 | 0 | 80 | 100 Pigweed | 50 | | 70 | 90 |
| Ragweed | 80 | 60 | 20 | 80 | 0 | 0 | 100 Ragweed | 0 | | 30 | 80 |
| Ryegrass, It. | 60 | 10 | 20 | 80 | — | 30 | 80 Ryegrass, It. | 0 | | 70 | 40 |
| Wheat | 0 | 0 | 0 | 0 | 0 | 0 | 0 Wheat | 0 | | 0 | 0 |

| 1000 g ai/ha Preemergence | Compound 1 | 1000 g ai/ha Preemergence | Compound 1 |
|---|---|---|---|
| Barnyardgrass | 80 | Pigweed | 60 |
| Foxtail, Green | 70 | Ragweed | 100 |
| Kochia | 70 | Ryegrass, It. | 100 |

| 500 g ai/ha Preemergence | Compounds | | | | 125 g ai/ha Preemergence | Compounds | | | | | | |
|---|---|---|---|---|---|---|---|---|---|---|---|---|
| | 2 | 3 | 6 | 7 | | 2 | 3 | 4 | 5 | 6 | 7 | 8 |
| Barnyardgrass | 0 | 0 | 30 | 0 | Barnyardgrass | 0 | 0 | 0 | 0 | 0 | 0 | 60 |
| Foxtail, Giant | — | — | 0 | 0 | Foxtail, Giant | — | — | — | — | 0 | 0 | 70 |
| Foxtail, Green | 0 | 0 | — | — | Foxtail, Green | 0 | 0 | 0 | 0 | — | — | — |
| Kochia | 80 | 30 | 40 | 0 | Kochia | 0 | 10 | 0 | 10 | 0 | 0 | 10 |
| Pigweed | 80 | 60 | 0 | 10 | Pigweed | 0 | 10 | 0 | 100 | 0 | 0 | 100 |
| Ragweed | 90 | 50 | 0 | 0 | Ragweed | 40 | 0 | 0 | 80 | 0 | 0 | 30 |
| Ryegrass, It. | 50 | 10 | 0 | 10 | Ryegrass, It. | 40 | 0 | 0 | 70 | 0 | 0 | 10 |

| 500 g ai/ha Preemergence | Compounds | | | 125 g ai/ha Preemergence | Compounds | | | | |
|---|---|---|---|---|---|---|---|---|---|
| | 2 | 3 | 7 | | 2 | 3 | 4 | 5 | 7 |
| Barnyardgrass | 0 | 0 | 0 | Barnyardgrass | 0 | 0 | 0 | 0 | 0 |
| Foxtail, Giant | — | — | 0 | Foxtail, Giant | — | — | — | — | 0 |
| Foxtail, Green | 0 | 0 | — | Foxtail, Green | 0 | 0 | 0 | 0 | — |
| Kochia | 80 | 30 | 0 | Kochia | 0 | 10 | 0 | 10 | 0 |
| Pigweed | 80 | 60 | 10 | Pigweed | 0 | 10 | 0 | 100 | 0 |
| Ragweed | 90 | 50 | 0 | Ragweed | 40 | 0 | 0 | 80 | 0 |
| Ryegrass, It. | 50 | 10 | 10 | Ryegrass, It. | 40 | 0 | 0 | 70 | 0 |

| 31 g ai/ha Preemergence | Compounds | | | 31 g ai/ha Preemergence | Compounds | | |
|---|---|---|---|---|---|---|---|
| | 4 | 5 | 8 | | 4 | 5 | 8 |
| Barnyardgrass | 0 | 20 | 0 | Pigweed | 0 | 20 | 10 |
| Foxtail, Green | 0 | 0 | 0 | Ragweed | 0 | 20 | 0 |
| Kochia | 0 | 0 | — | Ryegrass, It. | 0 | 40 | 0 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At the time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table B, are based on a scale of 0 to 100 where 0 is no effect and 100 is complete control. A dash (-) response means no test result.

TABLE B

| 250 g ai/ha Flood | Compounds | | | | | | |
|---|---|---|---|---|---|---|---|
| | 2 | 3 | 4 | 5 | 6 | 7 | 8 |
| Barnyardgrass | 0 | 0 | 0 | 0 | 0 | 0 | 60 |
| Ducksalad | 0 | 0 | 0 | 0 | 0 | 0 | 90 |
| Rice | 0 | 0 | 0 | 0 | 0 | 0 | 0 |
| Sedge, Umbrella | 0 | 50 | 0 | 0 | 0 | 0 | 95 |

What is claimed is:

1. A compound selected from Formula 1, N-oxides and salts thereof,

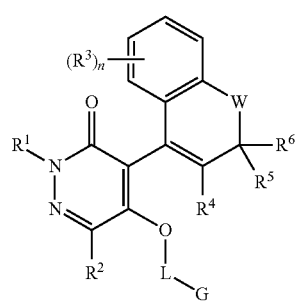

1 wherein
W is $C(R^7)(R^8)$;
$R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_2$-$C_7$ alkenyl, $C_3$-$C_7$ alkynyl, $C_3$-$C_7$ cycloalkyl, $C_4$-$C_7$ cycloalkylalkyl, $C_2$-$C_5$ cyanoalkyl, $C_1$-$C_4$ nitroalkyl, $C_2$-$C_7$ haloalkoxyalkyl, $C_1$-$C_7$ haloalkyl, $C_2$-$C_7$ haloalkenyl, $C_2$-$C_7$ alkoxyalkyl, $C_3$-$C_7$ alkylthioalkyl or $C_1$-$C_7$ alkoxy;

$R^2$ is H, halogen, cyano, —CHO, $C_1$-$C_7$ alkyl, $C_3$-$C_8$ alkylcarbonylalkyl, $C_3$-$C_8$ alkoxycarbonylalkyl, $C_1$-$C_4$ alkylcarbonyl, $C_2$-$C_7$ alkylcarbonyloxy, $C_4$-$C_7$ alkylcycloalkyl, $C_2$-$C_7$ alkenyl, $C_3$-$C_7$ alkynyl, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_7$ cycloalkyl, $C_4$-$C_7$ cycloalkylalkyl, $C_2$-$C_5$ cyanoalkyl, $C_1$-$C_4$ nitroalkyl, $C_2$-$C_7$ haloalkoxyalkyl, $C_1$-$C_7$ haloalkyl, $C_2$-$C_7$ haloalkenyl, $C_2$-$C_7$ alkoxyalkyl, $C_1$-$C_7$ alkoxy, $C_1$-$C_5$ alkylthio or $C_2$-$C_3$ alkoxycarbonyl;

each $R^3$ is independently H, halogen, nitro, cyano, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_2$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_4$ haloalkylthio or $C_2$-$C_5$ alkoxycarbonyl;

n is 0 to 3;

each $R^4$ is independently H, halogen, nitro, cyano, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_2$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_4$ haloalkylthio or $C_2$-$C_5$ alkoxycarbonyl;

$R^5$ is H or $C_1$-$C_5$ alkyl;
$R^6$ is H or $C_1$-$C_5$ alkyl;
$R^7$ is H or $C_1$-$C_5$ alkyl;
$R^8$ is H or $C_1$-$C_5$ alkyl;

L is a direct bond, $C_1$-$C_4$ alkanediyl or $C_2$-$C_4$ alkenediyl;

G is H, $C(=O)R^9$, $C(=S)R^9$, $CO_2R^{10}$, $C(=O)SR^{10}$, $S(O)_2R^9$, $C(=O)N(R^{11})(R^{12})$, $S(=O)_2N(R^{11})(R^{12})$ or $P(=O)(R^{13})(R^{14})$, or $C_1$-$C_7$ alkyl, $C_2$-$C_5$ alkenyl, $C_2$-$C_4$ alkynyl, $C_1$-$C_7$ haloalkyl, $C_2$-$C_5$ haloalkenyl, $C_2$-$C_4$ haloalkynyl, $C_2$-$C_4$ alkoxyalkyl, $C_3$-$C_6$ cycloalkyl or $C_4$-$C_7$ cycloalkylalkyl; or a 5- or 6-membered heterocyclic ring optionally substituted by halogen, $C_1$-$C_4$ alkyl or $C_1$-$C_4$ haloalkyl;

$R^9$ and $R^{11}$ are independently H, $C_1$-$C_7$ alkyl, $C_3$-$C_7$ alkenyl, $C_3$-$C_7$ alkynyl, $C_3$-$C_7$ cycloalkyl, $C_1$-$C_7$ haloalkyl, $C_3$-$C_7$ haloalkenyl, $C_2$-$C_7$ alkoxyalkyl or $C_4$-$C_7$ cycloalkylalkyl; or phenyl, benzyl, or a 5- to 6-membered heterocyclic ring, each phenyl, benzyl or heterocyclic ring optionally substituted by halogen, $C_1$-$C_4$ alkyl or $C_1$-$C_4$ haloalkyl;

$R^{10}$ is $C_1$-$C_7$ alkyl, $C_3$-$C_7$ alkenyl, $C_3$-$C_7$ alkynyl, $C_3$-$C_7$ cycloalkyl, $C_2$-$C_7$ haloalkyl, $C_3$-$C_7$ haloalkenyl, $C_2$-$C_7$ alkoxyalkyl or $C_4$-$C_7$ cycloalkylalkyl; or phenyl, benzyl or a 5- to 6-membered heterocyclic ring, each phenyl, benzyl or heterocyclic ring optionally substituted by halogen, $C_1$-$C_4$ alkyl or $C_1$-$C_4$ haloalkyl;

$R^{12}$ is H, $C_1$-$C_7$ alkyl, $C_2$-$C_7$ alkenyl, $C_2$-$C_7$ alkynyl, $C_3$-$C_7$ cycloalkyl, $C_4$-$C_7$ cycloalkylalkyl, $C_1$-$C_7$ haloalkyl or $C_2$-$C_7$ alkoxyalkyl;

$R^{13}$ is $C_1$-$C_7$ alkyl or $C_1$-$C_7$ alkoxy; and
$R^{14}$ is $C_1$-$C_7$ alkyl or $C_1$-$C_7$ alkoxy.

2. The compound of claim 1 wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_1$-$C_7$ haloalkyl, $C_2$-$C_7$ haloalkenyl, $C_2$-$C_7$ alkoxyalkyl or $C_1$-$C_7$ alkoxy;

$R^2$ is H, halogen, cyano, —CHO, $C_1$-$C_7$ alkyl, $C_3$-$C_8$ alkylcarbonylalkyl, $C_3$-$C_8$ alkoxycarbonylalkyl, $C_1$-$C_4$ alkylcarbonyl, $C_2$-$C_7$ alkylcarbonyloxy, $C_4$-$C_7$ alkylcycloalkyl, $C_3$-$C_7$ cycloalkyl, $C_4$-$C_7$ cycloalkylalkyl, $C_2$-$C_7$ haloalkoxyalkyl, $C_1$-$C_7$ haloalkyl, $C_2$-$C_7$ alkoxyalkyl, $C_1$-$C_7$ alkoxy, $C_1$-$C_5$ alkylthio or $C_2$-$C_3$ alkoxycarbonyl;

each $R^3$ is independently H, halogen, $C_1$-$C_5$ alkyl, $C_3$-$C_5$ cycloalkyl, $C_1$-$C_5$ haloalkyl, $C_1$-$C_5$ alkoxy or $C_1$-$C_5$ haloalkoxy;

n is 0 to 2;

$R^4$ is H, halogen, $C_1$-$C_3$ alkyl, $C_3$-$C_4$ cycloalkyl, $C_1$-$C_3$ haloalkyl or $C_1$-$C_3$ alkoxy;

L is a direct bond or $C_1$-$C_2$ alkanediyl;

G is H, $C(=O)R^9$, $C(=S)R^9$, $CO_2R^{10}$, $C(=O)SR^{10}$, $CON(R^{11})(R^{12})$ or $P(=O)(R^{13})(R^{14})$; or $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_3$-$C_6$ cycloalkyl or $C_4$-$C_7$ cycloalkylalkyl;

$R^9$ and $R^{11}$ are independently H, $C_1$-$C_7$ alkyl, $C_3$-$C_7$ alkenyl, $C_3$-$C_7$ alkynyl, $C_3$-$C_7$ cycloalkyl or $C_1$-$C_7$ haloalkyl; or phenyl, benzyl, or a 6-membered heterocyclic ring, each phenyl, benzyl or heterocyclic ring optionally substituted by halogen, $C_1$-$C_4$ alkyl or $C_1$-$C_4$ haloalkyl;

$R^{10}$ is $C_1$-$C_7$ alkyl, $C_3$-$C_7$ alkenyl, $C_3$-$C_7$ cycloalkyl, $C_2$-$C_7$ haloalkyl or $C_3$-$C_7$ haloalkenyl; or phenyl, benzyl or a 6-membered heterocyclic ring, each phenyl, benzyl or heterocyclic ring optionally substituted by halogen, $C_1$-$C_4$ alkyl or $C_1$-$C_4$ haloalkyl;

$R^{12}$ is H, $C_1$-$C_7$ alkyl, $C_2$-$C_7$ alkenyl, $C_2$-$C_7$ alkynyl or $C_3$-$C_7$ cycloalkyl;

$R^{13}$ is $C_1$-$C_4$ alkyl or $C_1$-$C_4$ alkoxy; and
$R^{14}$ is $C_1$-$C_4$ alkyl or $C_1$-$C_4$ alkoxy.

3. The compound of claim 2 wherein $R^1$ is H, $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ cycloalkyl, $C_4$-$C_7$ cycloalkylalkyl, $C_2$-$C_7$ alkoxyalkyl or $C_1$-$C_7$ alkoxy;

$R^2$ is H, halogen, cyano, —CHO, $C_1$-$C_7$ alkyl, $C_4$-$C_7$ alkylcycloalkyl, $C_3$-$C_7$ cycloalkyl, $C_4$-$C_7$ cycloalkylalkyl, $C_2$-$C_7$ haloalkoxyalkyl, $C_1$-$C_7$ haloalkyl, $C_2$-$C_7$ alkoxyalkyl, $C_1$-$C_7$ alkoxy or $C_1$-$C_5$ alkylthio;

each $R^3$ is independently H, halogen, $C_1$-$C_5$ alkyl, $C_1$-$C_5$ haloalkyl, $C_1$-$C_5$ alkoxy or $C_1$-$C_5$ haloalkoxy;

n is 0 or 1;

$R^4$ is H, halogen, $C_1$-$C_2$ alkyl, cyclopropyl or $C_1$-$C_2$ haloalkyl;

L is a direct bond;

G is H, $C(=O)R^9$, $CO_2R^{10}$, $CON(R^{11})(R^{12})$ or $P(=O)(R^{13})(R^{14})$; or $C_1$-$C_4$ alkyl, $C_2$-$C_4$ alkenyl, $C_1$-$C_4$ haloalkyl, $C_2$-$C_4$ haloalkenyl, $C_2$-$C_4$ alkoxyalkyl, $C_3$-$C_6$ cycloalkyl or $C_4$-$C_7$ cycloalkylalkyl;

$R^9$ and $R^{11}$ are independently H, $C_1$-$C_7$ alkyl or $C_3$-$C_7$ alkenyl; or phenyl, benzyl, each phenyl or benzyl optionally substituted by halogen, $C_1$-$C_4$ alkyl or $C_1$-$C_4$ haloalkyl;

$R^{10}$ is $C_1$-$C_7$ alkyl or $C_3$-$C_7$ cycloalkyl; or phenyl or benzyl, each phenyl or benzyl optionally substituted by halogen, $C_1$-$C_4$ alkyl or $C_1$-$C_4$ haloalkyl;

$R^{12}$ is H, $C_1$-$C_7$ alkyl or $C_3$-$C_7$ cycloalkyl;
$R^{13}$ is $C_1$-$C_2$ alkyl or $C_1$-$C_2$ alkoxy; and
$R^{14}$ is $C_1$-$C_2$ alkyl or $C_1$-$C_2$ alkoxy.

4. The compound of claim 3 wherein $R^1$ is H, $C_1$-$C_7$ alkyl, $C_4$-$C_7$ alkylcycloalkyl, $C_3$-$C_7$ cycloalkyl, $C_4$-$C_7$ cycloalkylalkyl or $C_2$-$C_7$ alkoxyalkyl;

$R^2$ is H, halogen, cyano, $C_1$-$C_7$ alkyl, $C_2$-$C_7$ haloalkoxyalkyl, $C_1$-$C_7$ haloalkyl, $C_2$-$C_7$ alkoxyalkyl, $C_1$-$C_7$ alkoxy or $C_1$-$C_5$ alkylthio;

each $R^3$ is independently H, halogen, methyl, ethyl, $CF_3$ or $-OCHF_2$;

$R^4$ is H, halogen, methyl, ethyl or $CF_3$;

G is H, $C(=O)R^9$, $CO_2R^{10}$ or $P(=O)(R^{13})(R^{14})$; or $C_1$-$C_4$ alkyl, $C_1$-$C_4$ haloalkyl, $C_2$-$C_4$ alkoxyalkyl or $C_3$-$C_6$ cycloalkyl;

$R^9$ is H or $C_1$-$C_7$ alkyl; or benzyl optionally substituted by halogen, $C_1$-$C_4$ alkyl or $C_1$-$C_4$ haloalkyl; and $R^{10}$ is $C_1$-$C_7$ alkyl; or phenyl optionally substituted by halogen, $C_1$-$C_4$ alkyl or $C_1$-$C_4$ haloalkyl.

5. The compound of claim 4 wherein $R^1$ is H, $C_1$-$C_7$ alkyl, $C_3$-$C_7$ cycloalkyl, $C_4$-$C_7$ cycloalkylalkyl or $C_2$-$C_7$ alkoxyalkyl;

$R^2$ is H, halogen, cyano, $C_1$-$C_7$ alkyl, $C_1$-$C_7$ haloalkyl or $C_1$-$C_7$ alkoxy;

each $R^3$ is independently H, F, Cl, Br or methyl;

$R^4$ is H, F, Cl, Br or methyl;

$R^5$ is H or methyl;

$R^6$ is H or methyl;

$R^7$ is H or methyl;

$R^8$ is H or methyl;

G is H, $C(=O)R^9$ or $CO_2R^{10}$; or $C_2$-$C_4$ alkoxyalkyl or $C_3$-$C_6$ cycloalkyl;

$R^9$ is $C_1$-$C_7$ alkyl; or benzyl optionally substituted by halogen, $C_1$-$C_4$ alkyl or $C_1$-$C_4$ haloalkyl; and $R^{10}$ is $CH_3$, $CH_2CH_3$, $CH_2CH_2CH_3$, Ph, Ph(4-Cl), Ph(3-$CF_3$) or Ph(4-$CF_3$).

6. The compound of claim 5 wherein $R^1$ is H, $C_1$-$C_7$ alkyl, $C_3$-$C_7$ cycloalkyl or $C_2$-$C_7$ alkoxyalkyl;

$R^2$ is H, Cl, Br, I, cyano, methyl, $CF_3$ or methoxy;

n is 0;

$R^4$ is methyl;

$R^5$ is H;

$R^6$ is H;

$R^7$ is H;

$R^8$ is H; and

G is H.

7. A compound of claim 1 that is 4-(3,4-dihydro-2-methyl-1-naphthalenyl)-5-hydroxy-2,6-dimethyl-3-(2H)-pyridazinone.

8. A herbicidal composition comprising a compound of claim 1 and at least one component selected from the group consisting of surfactants, solid diluents and liquid diluents.

* * * * *